US011121327B2

(12) United States Patent
Parham et al.

(10) Patent No.: US 11,121,327 B2
(45) Date of Patent: Sep. 14, 2021

(54) SPIRO-CONDENSED LACTAM COMPOUNDS FOR ORGANIC ELECTROLUMINESCENT DEVICES

(71) Applicant: Merck Patent GmbH, Darmstadt (DE)

(72) Inventors: Amir Hossain Parham, Frankfurt Am Main (DE); Christof Pflumm, Darmstadt (DE); Thomas Eberle, Landau (DE); Anja Jatsch, Frankfurt Am Main (DE); Elvira Montenegro, Weinheim (DE); Jonas Valentin Kroeber, Frankfurt Am Main (DE); Rouven Linge, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 536 days.

(21) Appl. No.: 14/901,744

(22) PCT Filed: Jun. 3, 2014

(86) PCT No.: PCT/EP2014/001497
§ 371 (c)(1),
(2) Date: Dec. 29, 2015

(87) PCT Pub. No.: WO2015/000542
PCT Pub. Date: Jan. 8, 2015

(65) Prior Publication Data
US 2016/0372681 A1    Dec. 22, 2016

(30) Foreign Application Priority Data

Jul. 2, 2013  (EP) ..................................... 13003343

(51) Int. Cl.
| | | |
|---|---|---|
| *H01L 51/00* | (2006.01) | |
| *C07D 491/20* | (2006.01) | |
| *H01L 51/50* | (2006.01) | |
| *C07D 471/20* | (2006.01) | |
| *C07D 495/20* | (2006.01) | |
| *C07D 495/22* | (2006.01) | |
| *C07D 491/22* | (2006.01) | |
| *C07D 471/22* | (2006.01) | |
| *C07D 471/06* | (2006.01) | |
| *C07D 471/10* | (2006.01) | |
| *C09K 11/02* | (2006.01) | |
| *C09K 11/06* | (2006.01) | |

(52) U.S. Cl.
CPC ........ *H01L 51/0072* (2013.01); *C07D 471/06* (2013.01); *C07D 471/10* (2013.01); *C07D 471/20* (2013.01); *C07D 471/22* (2013.01); *C07D 491/20* (2013.01); *C07D 491/22* (2013.01); *C07D 495/20* (2013.01); *C07D 495/22* (2013.01); *C09K 11/025* (2013.01); *C09K 11/06* (2013.01); *H01L 51/0061* (2013.01); *H01L 51/0071* (2013.01); *C09K 2211/185* (2013.01); *H01L 51/0067* (2013.01); *H01L 51/5016* (2013.01)

(58) Field of Classification Search
CPC ............. H01L 51/0071; H01L 51/0072; H01L 51/0061; H01L 51/0067; H01L 51/5012; H01L 51/5016; H01L 51/5048; H01L 51/5052; H01L 51/5056; H01L 51/506; H01L 51/5064; H01L 51/5072; H01L 51/5076; H01L 51/508; H01L 51/5096; C07D 471/10; C07D 471/20; C07D 495/10; C07D 495/20; C07D 491/107; C07D 491/20; C07D 471/00; C07D 471/02; C07D 471/04; C07D 471/06; C07D 471/08; C07D 471/12; C07D 471/14; C07D 471/16; C07D 471/18; C07D 471/22; C07D 491/00; C07D 491/02; C07D 491/04; C07D 491/044; C07D 491/048; C07D 491/052; C07D 491/06; C07D 491/08; C07D 491/10; C07D 491/12; C07D 491/14; C07D 491/147; C07D 491/153; C07D 491/16; C07D 491/18; C07D 491/22; C07D 495/00; C07D 495/02; C07D 495/04; C07D 495/06; C07D 495/08; C07D 495/12; C07D 495/14; C07D 495/16; C07D 495/18; C07D 495/22; C09K 2211/185; C09K 11/025; C09K 11/06
See application file for complete search history.

(56) References Cited

U.S. PATENT DOCUMENTS

| 8,835,626 B2 | 9/2014 | Parham et al. |
| 9,356,243 B2 | 5/2016 | Parham et al. |
| (Continued) | | |

FOREIGN PATENT DOCUMENTS

| CN | 102822174 A | 12/2012 |
| DE | 10 2010 012738 A1 | 9/2011 |
| (Continued) | | |

OTHER PUBLICATIONS

Chi-Jen Lin, Heh-Lung Huang, Mei-Rurng Tseng, and Chien-Hong Cheng, High Energy Gap OLED Host Materials for Green and Blue Pholed Materials, Journal of Display Technology, vol. 5, No. 6, Jun. 2009, pp. 236-240.*

(Continued)

*Primary Examiner* — Dylan C Kershner
*Assistant Examiner* — Elizabeth M. Dahlburg
(74) *Attorney, Agent, or Firm* — Faegre Drinker Biddle & Reath LLP

(57) ABSTRACT

The invention relates to polycondensed lactam compounds as materials for use in electronic devices, and electronic devices, in particular organic electroluminescent devices, containing said materials.

4 Claims, No Drawings

(56) References Cited

U.S. PATENT DOCUMENTS

| | | | |
|---|---|---|---|
| 2004/0109951 A1* | 6/2004 | Irvin | C09K 11/02 |
| | | | 428/690 |
| 2006/0103298 A1* | 5/2006 | Lee | H01L 51/5016 |
| | | | 313/504 |
| 2013/0053555 A1* | 2/2013 | Parham | C07D 471/04 |
| | | | 544/31 |
| 2014/0249308 A1 | 9/2014 | Parham et al. | |

FOREIGN PATENT DOCUMENTS

| | | | | |
|---|---|---|---|---|
| DE | 102010019306 A1 * | 11/2011 | | C07D 471/04 |
| WO | WO-2011/116865 A1 | 9/2011 | | |
| WO | WO-2011137951 A1 * | 11/2011 | | C07D 471/04 |
| WO | WO-2013064206 A1 | 5/2013 | | |

OTHER PUBLICATIONS

Kim et al. Organic Electronics 13 (2012) 1245-1249. (Year: 2012).*
Japanese Office Action dated Apr. 3, 2018 for Japanese Patent Application No. 2016-522301.
International Search Report for PCT/EP2014/001497 dated Aug. 21, 2014.
Méhes, G., et a., "Enhanced Electroluminescence Efficiency in a Spiro-Acridine Derivative through Thermally Activated Delayed Fluorescene", Angewandte Chemie International Edition, vol. 51, No. 45, (2012), pp. 11311-11315.

\* cited by examiner

SPIRO-CONDENSED LACTAM COMPOUNDS FOR ORGANIC ELECTROLUMINESCENT DEVICES

CROSS-REFERENCE TO RELATED APPLICATIONS

This application is a national stage application (under 35 U.S.C. § 371) of PCT/EP2014/001497, filed Jun. 3, 2014, which claims benefit of European Application No. 13003343.4, filed Jul. 2, 2013, both of which are incorporated herein by reference in their entirety.

The present invention relates to materials for use in electronic devices, especially in organic electroluminescent devices, and to electronic devices, especially organic electroluminescent devices, comprising these materials.

Emitting materials used in organic electroluminescent devices (OLEDs) are increasingly organometallic complexes which exhibit phosphorescence rather than fluorescence. For quantum-mechanical reasons, up to four times the energy efficiency and power efficiency is possible using organometallic compounds as phosphorescent emitters. In general terms, however, there is still a need for improvement in OLEDs, especially also in OLEDs which exhibit triplet emission (phosphorescence), for example with regard to efficiency, operating voltage and lifetime. This is especially true of OLEDs which emit in the shorter-wave range, for example in the green.

The properties of phosphorescent OLEDs are not just determined by the triplet emitters used. Also of particular significance here are especially the other materials used, such as matrix materials, hole blocker materials, electron transport materials, hole transport materials and electron or exciton blocker materials. Improvements to these materials can thus also lead to distinct improvements in the OLED properties. For fluorescent OLEDs too, there is still a need for improvement in these materials.

According to the prior art, lactams (for example according to WO 2011/116865 or WO 2011/137951) are one kind of matrix materials used for phosphorescent emitters. However, there is still a need for improvement in the case of use of these matrix materials, and likewise of other matrix materials, especially in relation to the efficiency and lifetime of the device.

It is an object of the present invention to provide compounds suitable for use in a fluorescent or phosphorescent OLED, especially a phosphorescent OLED, for example as matrix material or as hole transport/electron blocker material or exciton blocker material or as electron transport or hole blocker material. It is a particular object of the present invention to provide matrix materials suitable for green-, yellow- and red-phosphorescing OLEDs and, according to the exact structure, also for blue-phosphorescing OLEDs.

It has been found that, surprisingly, particular compounds described in detail below achieve this object and lead to very good properties of the organic electroluminescent device, especially with regard to lifetime, efficiency and operating voltage. This is especially true of red-, yellow- and green-phosphorescing electroluminescent devices, particularly when the compounds of the invention are used as matrix material. The materials additionally feature high oxidation stability in solution and a high thermal stability. The present invention therefore provides these materials and electronic devices, especially organic electroluminescent devices, comprising such materials.

The present invention provides a compound of the following formula (1)

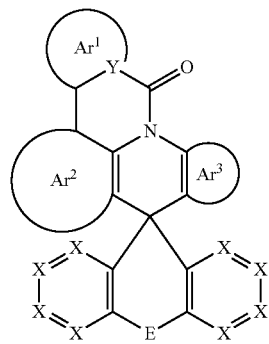

Formula (1)

where the symbols and indices used are as follows:

X is the same or different at each instance and is CR or N or exactly two adjacent X groups in a cycle together are a group selected from NR, O and S, forming a five-membered ring;

Y is C when $Ar^1$ is a 6-membered aryl or heteroaryl group, or is C or N when $Ar^1$ is a 5-membered heteroaryl group;

E is NR, $CR_2$, O, S, C=O, $SiR_2$, SO or $SO_2$;

$Ar^1$ together with the Y group and the carbon atom shown explicitly is an aromatic or heteroaromatic ring system which has 5 to 30 aromatic ring atoms and may be substituted by one or more R radicals;

$Ar^2$, $Ar^3$ is the same or different at each instance and, together with the carbon atoms shown explicitly, is an aromatic or heteroaromatic ring system which has 5 to 30 aromatic ring atoms and may be substituted by one or more R radicals;

R is the same or different at each instance and is selected from the group consisting of H, D, F, C, Br, I, CN, $NO_2$, $N(Ar^4)_2$, $N(R^1)_2$, $C(=O)Ar^4$, $C(=O)R^1$, $P(=O)(Ar^4)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^1$ radicals, where one or more nonadjacent $CH_2$ groups may be replaced by $R^1C=CR^1$, C=C, $Si(R^1)_2$, $Ge(R^1)_2$, $Sn(R^1)_2$, C=O, C=S, C=Se, $C=NR^1$, $P(=O)(R^1)$, SO, $SO_2$, $NR^1$, O, S or $CONR^1$ and where one or more hydrogen atoms may be replaced by D, F, Cl, Br, I, CN or $NO_2$, an aromatic or heteroaromatic ring system which has 5 to 80, preferably 5 to 60, aromatic ring atoms and may be substituted in each case by one or more $R^1$ radicals, an aryloxy or heteroaryloxy group which has 5 to 60 aromatic ring atoms and may be substituted by one or more $R^1$ radicals, or a combination of these systems, where it is optionally possible for two or more adjacent R substituents to form a monocyclic or polycyclic, aliphatic, aromatic or heteroaromatic ring system which may be substituted by one or more $R^1$ radicals;

$R^1$ is the same or different at each instance and is selected from the group consisting of H, D, F, C, Br, I, CN, $NO_2$, $N(Ar^4)_2$, $N(R^2)_2$, $C(=O)Ar^4$, $C(=O)R^2$, $P(=O)(Ar^4)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which may be substituted by one or more $R^2$ radicals, where one or more nonadjacent $CH_2$ groups may be replaced by $R^2C=CR^2$, C=C, $Si(R^2)_2$, $Ge(R^2)_2$, $Sn(R^2)_2$, C=O, C=S, C=Se, $C=NR^2$, $P(=O)(R^2)$, SO, $SO_2$, NR$^2$, O, S or CONR$^2$ and where one or more hydrogen atoms may be replaced by D, F, C, Br, I, CN or NO$_2$, an aromatic or heteroaromatic ring system which has 5 to 60 aromatic ring atoms and may be substituted in each case by one or more R$^2$ radicals, an aryloxy or heteroaryloxy group which has 5 to 60 aromatic ring atoms and may be substituted by one or more R$^2$ radicals, or a combination of these systems, where it is optionally possible for two or more adjacent R substituents to form a monocyclic or polycyclic, aliphatic, aromatic or heteroaromatic ring system which may be substituted by one or more R$^2$ radicals;

Ar$^4$ is the same or different at each instance and is an aromatic or heteroaromatic ring system which has 5-30 aromatic ring atoms and may be substituted by one or more nonaromatic R$^2$ radicals; at the same time, two Ar$^4$ radicals bonded to the same nitrogen atom or phosphorus atom may also be bridged to one another by a single bond or a bridge selected from N(R$^2$), C(R$^2$)$_2$ and O;

R$^2$ is selected from the group consisting of H, D, F, CN, an aliphatic hydrocarbyl radical having 1 to 20 carbon atoms, an aromatic or heteroaromatic ring system having 5 to 30 aromatic ring atoms in which one or more hydrogen atoms may be replaced by D, F, Cl, Br, I or CN, where two or more adjacent R$^2$ substituents together may form a mono- or polycyclic, aliphatic, aromatic or heteroaromatic ring system.

An aryl group in the context of this invention contains 6 to 60 carbon atoms; a heteroaryl group in the context of this invention contains 2 to 60 carbon atoms and at least one heteroatom, with the proviso that the sum total of carbon atoms and heteroatoms is at least 5. The heteroatoms are preferably selected from N, O and/or S. An aryl group or heteroaryl group is understood here to mean a simple aromatic cycle, i.e. benzene, or a simple heteroaromatic cycle, for example pyridine, pyrimidine, thiophene, etc., or a fused (annelated) aryl or heteroaryl group, for example naphthalene, anthracene, phenanthrene, quinoline, isoquinoline, etc. Aromatic systems joined to one another by a single bond, for example biphenyl, by contrast, are not referred to as an aryl or heteroaryl group but as an aromatic ring system.

An aromatic ring system in the context of this invention contains 6 to 80 carbon atoms in the ring system. A heteroaromatic ring system in the context of this invention contains 2 to 60 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be joined by a nonaromatic unit, for example a carbon, nitrogen or oxygen atom. For example, systems such as fluorene, 9,9'-spirobifluorene, 9,9-diarylfluorene, triarylamine, diaryl ethers, stilbene, etc. shall also be be regarded as aromatic ring systems in the context of this invention, and likewise systems in which two or more aryl groups are joined, for example, by a short alkyl group.

In the context of the present invention, an aliphatic hydrocarbyl radical or an alkyl group or an alkenyl or alkynyl group which may contain 1 to 40 carbon atoms and in which individual hydrogen atoms or CH$_2$ groups may also be replaced by the abovementioned groups are preferably understood to mean the methyl, ethyl, n-propyl, i-propyl, n-butyl, i-butyl, s-butyl, t-butyl, 2-methylbutyl, n-pentyl, s-pentyl, neopentyl, cyclopentyl, n-hexyl, neohexyl, cyclohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl, heptynyl or octynyl radicals. An alkoxy group having 1 to 40 carbon atoms is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy and 2,2,2-trifluoroethoxy. A thioalkyl group having 1 to 40 carbon atoms is understood to mean especially methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentenylthio, hexynylthio, heptynylthio or octynylthio. In general, alkyl, alkoxy or thioalkyl groups according to the present invention may be straight-chain, branched or cyclic, where one or more nonadjacent CH$_2$ groups may be replaced by the abovementioned groups; in addition, it is also possible for one or more hydrogen atoms to be replaced by D, F, Cl, Br, I, CN or NO$_2$, preferably F, Cl or CN, further preferably F or CN, especially preferably CN.

An aromatic or heteroaromatic ring system which has 5-80 aromatic ring atoms and may also be substituted in each case by the abovementioned R$^2$ radicals or a hydrocarbyl radical and which may be joined to the aromatic or heteroaromatic system via any desired positions is especially understood to mean groups derived from benzene, naphthalene, anthracene, benzanthracene, phenanthrene, pyrene, chrysene, perylene, fluoranthene, naphthacene, pentacene, benzopyrene, biphenyl, biphenylene, terphenyl, triphenylene, fluorene, spirobifluorene, dihydrophenanthrene, dihydropyrene, tetrahydropyrene, cis- or trans-indenofluorene, cis- or trans-indenocarbazole, cis- or trans-indolocarbazole, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, hexaazatriphenylene, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,5-tetrazine, 1,2,3,4-tetrazine, 1,2,3,5-tetrazine, purine, pteridine, indolizine and benzothiadiazole or groups derived from a combination of these systems.

In a preferred embodiment of the invention, X is CR or N, where not more than one X group per cycle is N. Most preferably, X is CR.

In a further preferred embodiment of the invention, E is NR where R is not H or D, or CR$_2$, O, S or C=O. More preferably, E is NR where R is not H or D, or CR$_2$ or O.

In a further preferred embodiment of the invention, the Ar$^1$ group is a group of the following formula (2), (3), (4), (5) or (6)

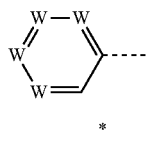

Formula (2)

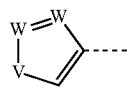

Formula (3)

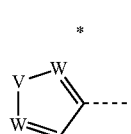

Formula (4)

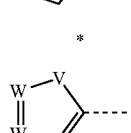

Formula (5)

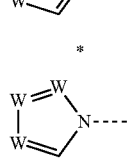

Formula (6)

where the dotted bond indicates the linkage to the carbonyl group of the lactam, * indicates the position of the linkage to Ar$^2$ and in addition:

W is the same or different at each instance and is CR or N, or two adjacent W groups are a group of the following formula (7) or (8)

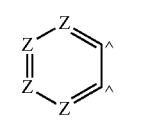

Formula (7)

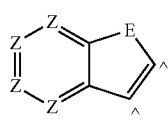

Formula (8)

where E is as defined above, Z is the same or different at each instance and is CR or N and ^ indicate the corresponding adjacent W groups in the formula (2) to (6);

V is NR, O or S.

In a further preferred embodiment of the invention, the Ar$^3$ group is a group of one of the following formulae (9), (10) and (11)

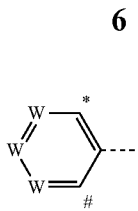

Formula (9)

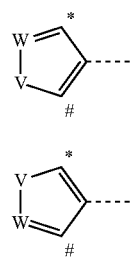

Formula (10)

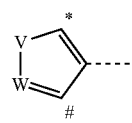

Formula (11)

where the dotted bond indicates the linkage to N, # indicates the position of the linkage to the spiro carbon atom, * indicates the linkage to Ar$^1$ and W and V are each as defined above.

In a further preferred embodiment of the invention, the Ar$^3$ group is a group of one of the following formulae (12), (13), (14) and (15)

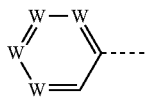

Formula (12)

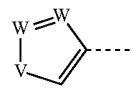

Formula (13)

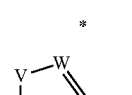

Formula (14)

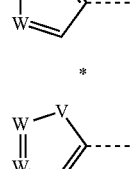

Formula (15)

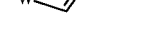

where the dotted bond indicates the linkage to N, * indicates the linkage to the spiro carbon atom and W and V are each as defined above.

In a particularly preferred embodiment of the invention, the abovementioned preferences occur simultaneously. Particular preference is therefore given to compounds of formula (1) for which:

X is the same or different at each instance and is CR or N, where not more than one X group per cycle is N;

E is the same or different at each instance and is NR where R is not H or D, or CR$_2$, O, S or C=O;

Ar$^1$ is selected from the groups of the abovementioned formulae (2), (3), (4), (5) and (6);

Ar$^2$ is selected from the groups of the abovementioned formulae (9), (10) and (11);

Ar$^3$ is selected from the groups of the abovementioned formulae (12), (13), (14) and (15).

In a very particularly preferred embodiment of the invention, for compounds of the formula (1):

X is the same or different at each instance and is CR;
E is the same or different at each instance and is NR where R is not H or D, or $CR_2$ or O;
$Ar^1$ is selected from the groups of the abovementioned formulae (2), (3), (4), (5) and (6);
$Ar^2$ is selected from the groups of the abovementioned formulae (9), (10) and (11);
$Ar^3$ is selected from the groups of the abovementioned formulae (12), (13), (14) and (15).

At the same time, the abovementioned preferred $Ar^1$, $Ar^2$ and $Ar^3$ groups may be combined with one another as desired. Suitable combinations are thus as follows:

| $Ar^1$ | $Ar^2$ | $Ar^3$ |
|---|---|---|
| Formula (2) | Formula (9) | Formula (12) |
| Formula (2) | Formula (9) | Formula (13) |
| Formula (2) | Formula (9) | Formula (14) |
| Formula (2) | Formula (9) | Formula (15) |
| Formula (2) | Formula (10) | Formula (12) |
| Formula (2) | Formula (10) | Formula (13) |
| Formula (2) | Formula (10) | Formula (14) |
| Formula (2) | Formula (10) | Formula (15) |
| Formula (2) | Formula (11) | Formula (12) |
| Formula (2) | Formula (11) | Formula (13) |
| Formula (2) | Formula (11) | Formula (14) |
| Formula (2) | Formula (11) | Formula (15) |
| Formula (2) | Formula (12) | Formula (12) |
| Formula (2) | Formula (12) | Formula (13) |
| Formula (2) | Formula (12) | Formula (14) |
| Formula (2) | Formula (12) | Formula (15) |
| Formula (3) | Formula (9) | Formula (12) |
| Formula (3) | Formula (9) | Formula (13) |
| Formula (3) | Formula (9) | Formula (14) |
| Formula (3) | Formula (9) | Formula (15) |
| Formula (3) | Formula (10) | Formula (12) |
| Formula (3) | Formula (10) | Formula (13) |
| Formula (3) | Formula (10) | Formula (14) |
| Formula (3) | Formula (10) | Formula (15) |
| Formula (3) | Formula (11) | Formula (12) |
| Formula (3) | Formula (11) | Formula (13) |
| Formula (3) | Formula (11) | Formula (14) |
| Formula (3) | Formula (11) | Formula (15) |
| Formula (3) | Formula (12) | Formula (12) |
| Formula (3) | Formula (12) | Formula (13) |
| Formula (3) | Formula (12) | Formula (14) |
| Formula (3) | Formula (12) | Formula (15) |
| Formula (4) | Formula (9) | Formula (12) |
| Formula (4) | Formula (9) | Formula (13) |
| Formula (4) | Formula (9) | Formula (14) |
| Formula (4) | Formula (9) | Formula (15) |
| Formula (4) | Formula (10) | Formula (12) |
| Formula (4) | Formula (10) | Formula (13) |
| Formula (4) | Formula (10) | Formula (14) |
| Formula (4) | Formula (10) | Formula (15) |
| Formula (4) | Formula (11) | Formula (12) |
| Formula (4) | Formula (11) | Formula (13) |
| Formula (4) | Formula (11) | Formula (14) |
| Formula (4) | Formula (11) | Formula (15) |
| Formula (4) | Formula (12) | Formula (12) |
| Formula (4) | Formula (12) | Formula (13) |
| Formula (4) | Formula (12) | Formula (14) |
| Formula (4) | Formula (12) | Formula (15) |
| Formula (5) | Formula (9) | Formula (12) |
| Formula (5) | Formula (9) | Formula (13) |
| Formula (5) | Formula (9) | Formula (14) |
| Formula (5) | Formula (9) | Formula (15) |
| Formula (5) | Formula (10) | Formula (12) |
| Formula (5) | Formula (10) | Formula (13) |
| Formula (5) | Formula (10) | Formula (14) |
| Formula (5) | Formula (10) | Formula (15) |
| Formula (5) | Formula (11) | Formula (12) |
| Formula (5) | Formula (11) | Formula (13) |
| Formula (5) | Formula (11) | Formula (14) |
| Formula (5) | Formula (11) | Formula (15) |
| Formula (5) | Formula (12) | Formula (12) |
| Formula (5) | Formula (12) | Formula (13) |
| Formula (5) | Formula (12) | Formula (14) |
| Formula (5) | Formula (12) | Formula (15) |
| Formula (6) | Formula (9) | Formula (12) |
| Formula (6) | Formula (9) | Formula (13) |
| Formula (6) | Formula (9) | Formula (14) |
| Formula (6) | Formula (9) | Formula (15) |
| Formula (6) | Formula (10) | Formula (12) |
| Formula (6) | Formula (10) | Formula (13) |
| Formula (6) | Formula (10) | Formula (14) |
| Formula (6) | Formula (10) | Formula (15) |
| Formula (6) | Formula (11) | Formula (12) |
| Formula (6) | Formula (11) | Formula (13) |
| Formula (6) | Formula (11) | Formula (14) |
| Formula (6) | Formula (11) | Formula (15) |
| Formula (6) | Formula (12) | Formula (12) |
| Formula (6) | Formula (12) | Formula (13) |
| Formula (6) | Formula (12) | Formula (14) |
| Formula (6) | Formula (12) | Formula (15) |

More preferably, at least two of the $Ar^1$, $Ar^2$ and $Ar^3$ groups are a 6-membered aryl or a 6-membered heteroaryl group. Thus, more preferably, $Ar^1$ is a group of the formula (2) and at the same time $Ar^2$ is a group of the formula (9), or $Ar^1$ is a group of the formula (2) and at the same time $Ar^3$ is a group of the formula (12), or $Ar^2$ is a group of the formula (9) and at the same time $Ar^3$ is a group of the formula (12).

Particularly preferred embodiments of the invention are therefore the compounds of the following formulae (16) to (25)

Formula (16)

Formula (17)

Formula (18)

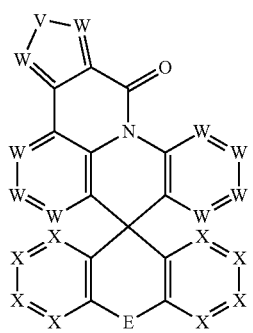

Formula (19)

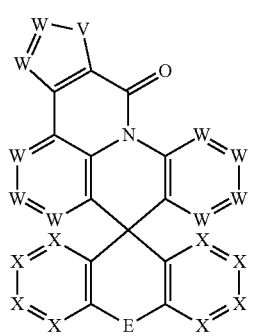

Formula (20)

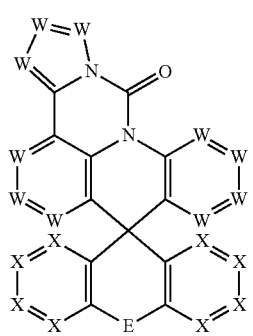

Formula (21)

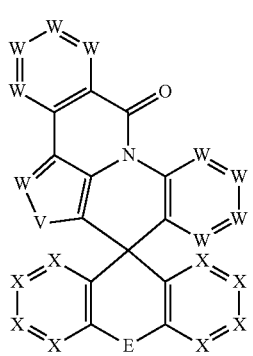

Formula (22)

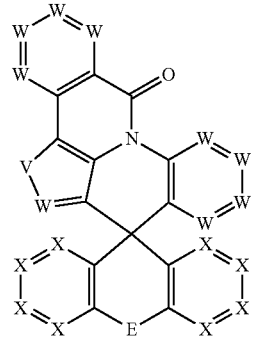

Formula (23)

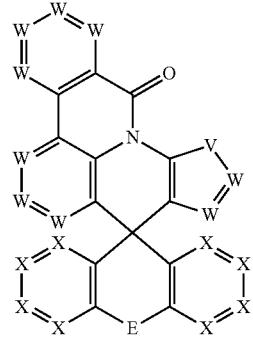

Formula (24)

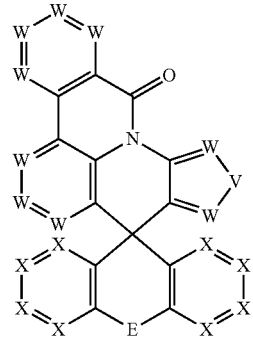

Formula (25)

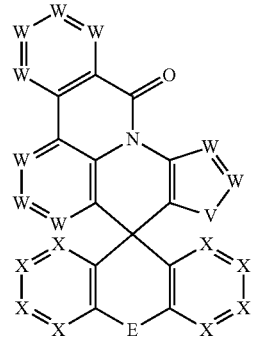

where the symbols used have the definitions given above.

As already stated above, in the compounds of the formulae (16) to (25), it is also possible for two adjacent W groups to be a group of the abovementioned formula (7) or (8).

In a further preferred embodiment of the compounds of formulae (16) to (25), not more than one W symbol in total per cycle is N, and the remaining W symbols that are not a group of the formula (7) or (8) are CR. In a particularly preferred embodiment of the invention, all W symbols that are not a group of the formula (7) or (8) are CR. In addition, more preferably, all X symbols are CR. Particular preference is therefore given to the compounds of the following formulae (16a) to (25a):
Formula (16a)
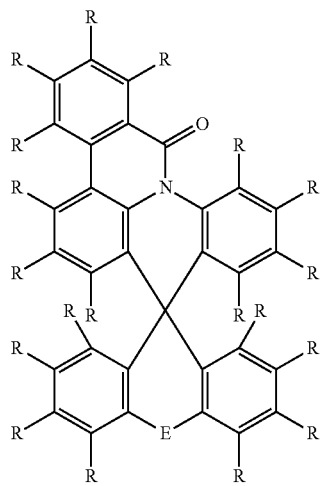
Formula (17a)
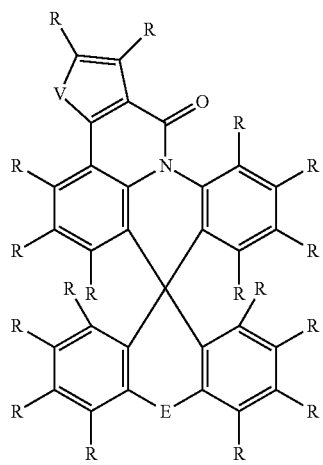
Formula (18a)
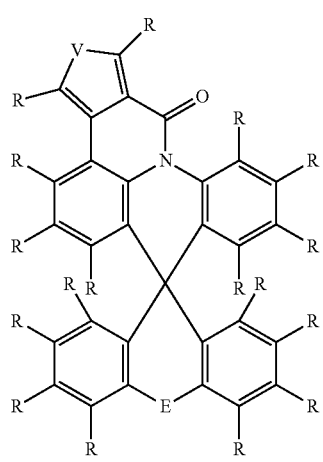
Formula (19a)
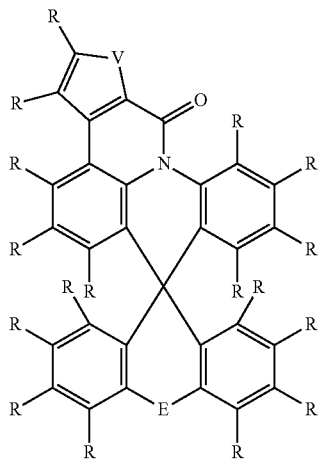
Formula (20a)
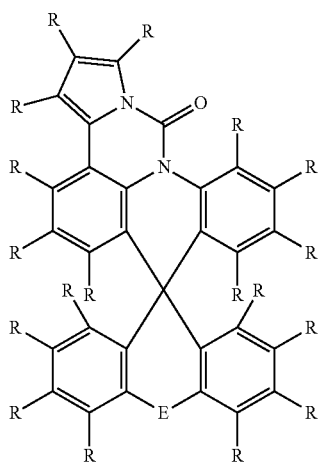
Formula (21a)
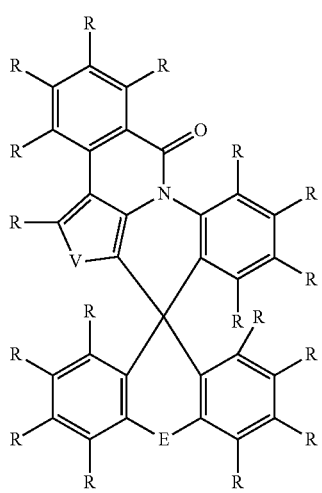

Formula (22a)
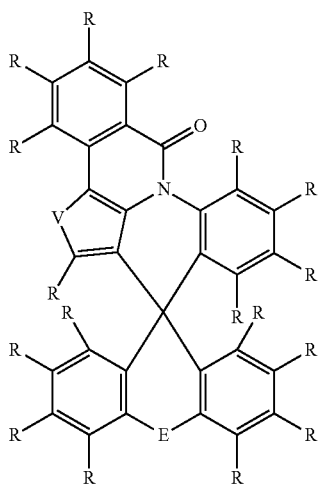
Formula (23a)
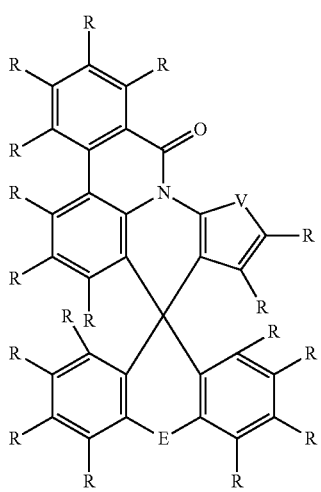
Formula (24a)
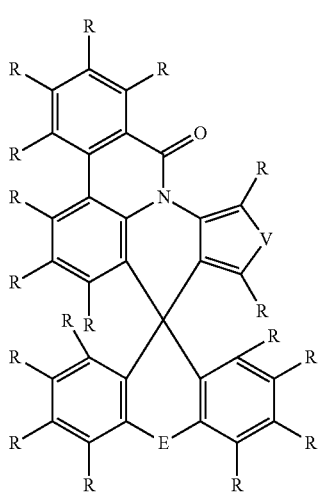
Formula (25a)
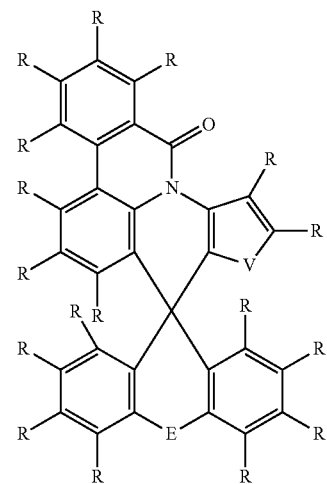
where the symbols used have the definitions given above.
Very particular preference is therefore given to the compounds of the following formulae (16b) to (25b):
Formula (16b)
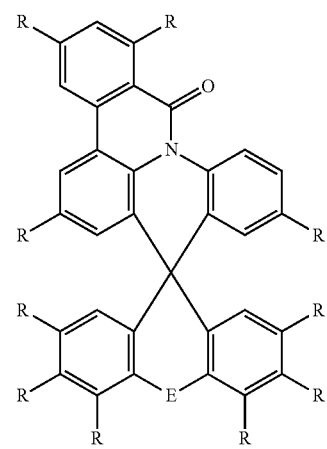
Formula (17b)
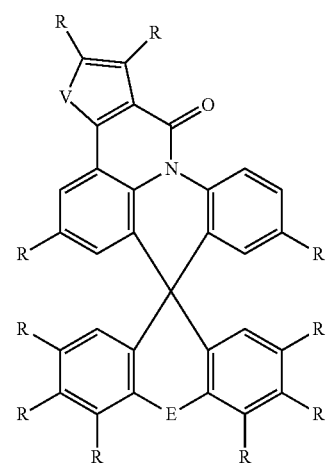

Formula (18b)
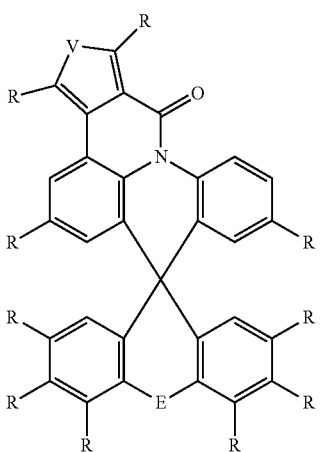
Formula (19b)
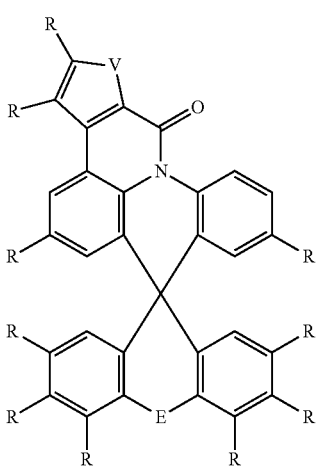
Formula (20b)
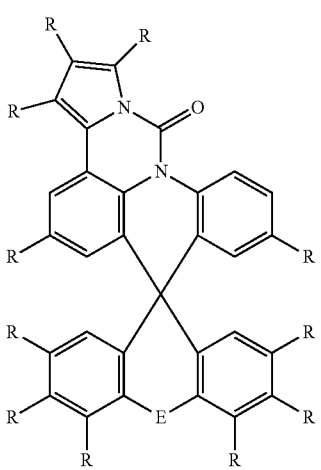
Formula (21b)
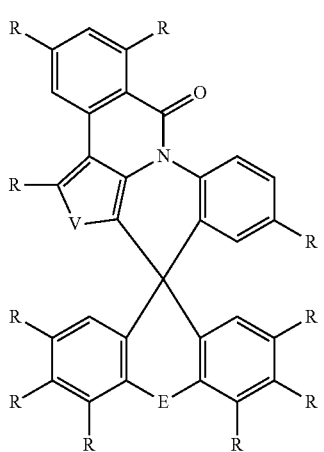
Formula (22b)
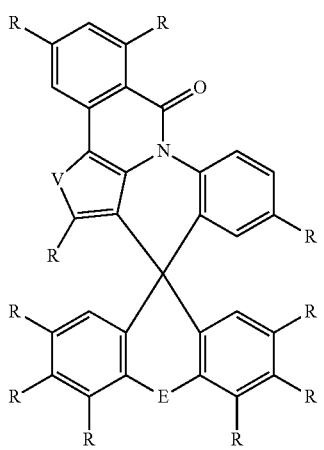
Formula (23b)
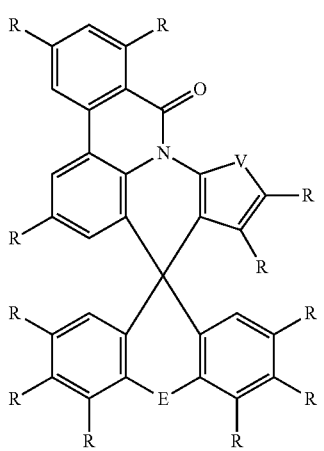

Formula (24b)
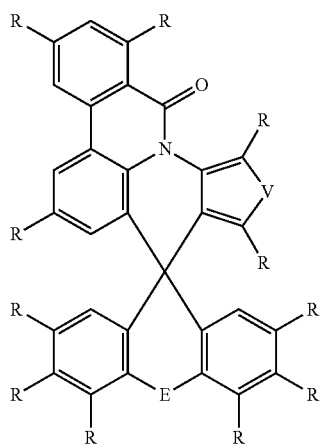
Formula (25b)
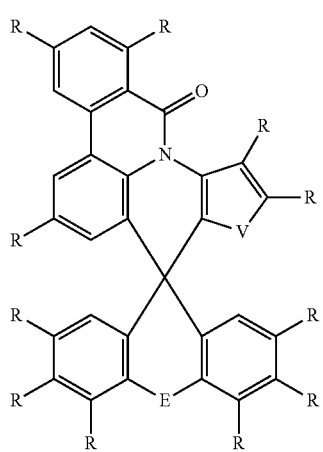
where the symbols used have the definitions given above.
Especially preferred structures are those of the formulae (16c) to (25c):
Formula (16c)
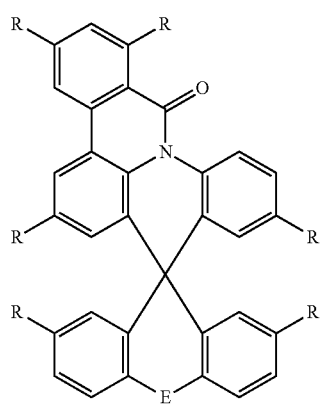
Formula (17c)
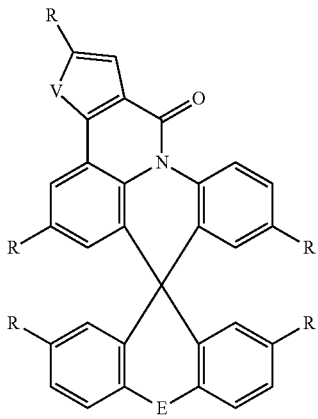
Formula (18c)
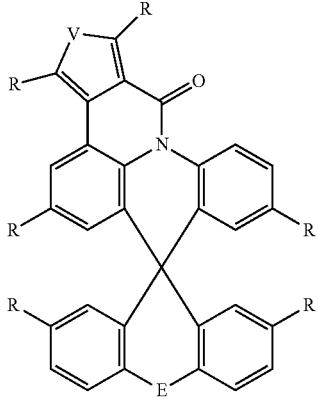
Formula (19c)
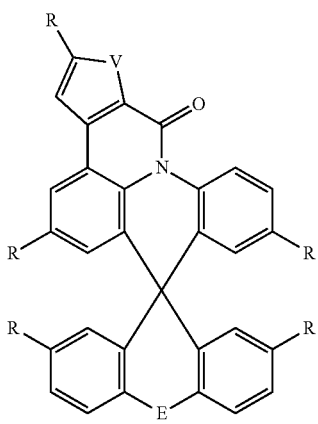
Formula (20c)
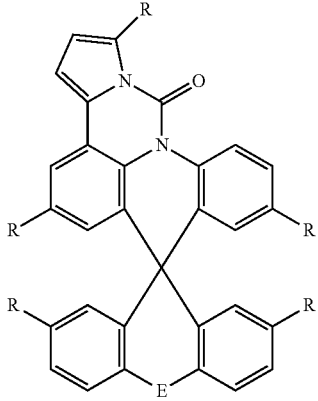

-continued

Formula (21c)

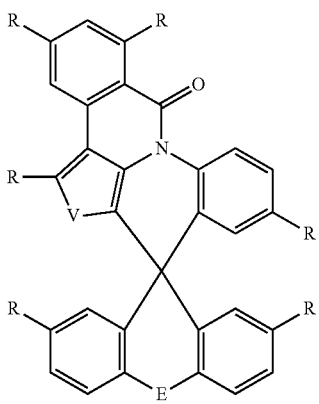

Formula (22c)

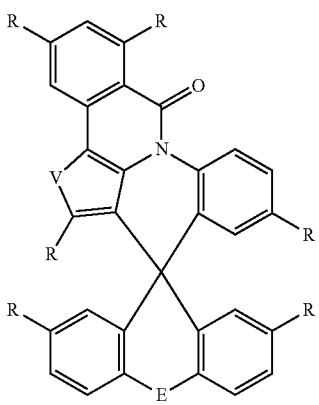

Formula (23c)

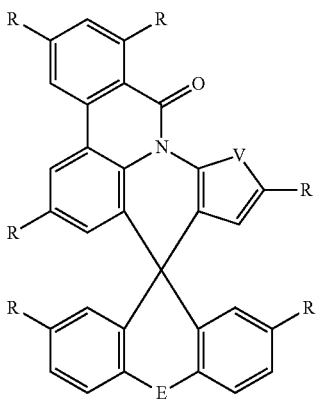

Formula (24c)

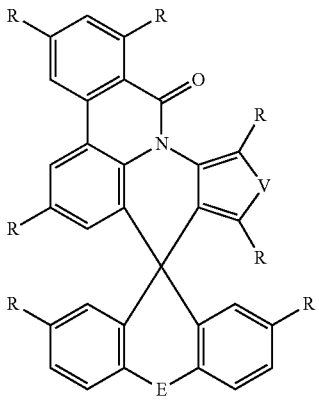

-continued

Formula (25c)

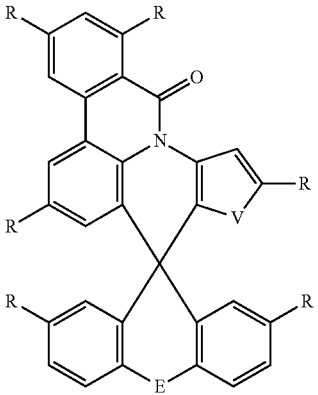

where E is NR where R is not H, or $CR_2$, O or S and the further symbols used have the definitions given above.

In these formulae (16) to (25), (16a) to (25a), (16b) to (25b) and (16c) to (25c), E is preferably $CR_2$, NR where R is not H, or O or S.

It is additionally preferable, if two adjacent W groups are a group of the formula (7) or (8), that not more than one Z group is N. More preferably, all Z groups are CR. It is additionally preferable, when two adjacent W groups are a group of the formula (8), that E in the group of the formula (8) is $CR_2$, C=O or NR.

When E is NR, R is preferably selected from aromatic and heteroaromatic ring systems which have 5 to 40 aromatic ring atoms and may be substituted by one or more $R^1$ radicals. Preferred R radicals bonded to the nitrogen atom are phenyl, ortho-, meta- or para-biphenyl, ortho-, meta-, para- or branched terphenyl, ortho-, meta-, para- or branched quaterphenyl, 1-, 2-, 3- or 4-fluorenyl, 1-, 2-, 3- or 4-spiro-bifluorenyl, triazine, 1-, 2-, 3- or 4-dibenzofuranyl, 1-, 2-, 3- or 4-dibenzothienyl or 1-, 2-, 3- or 4-carbazolyl, each of which may be substituted by one or more $R^1$ radicals.

In a further preferred embodiment of the invention, the R radical in the abovementioned formulae, if it is not bonded to the nitrogen of an E group, is the same or different at each instance and is selected from the group consisting of H, D, F, Cl, Br, CN, $N(Ar^1)_2$, $C(=O)Ar^1$, a straight-chain alkyl or alkoxy group having 1 to 10 carbon atoms or a branched or cyclic alkyl or alkoxy group having 3 to 10 carbon atoms or an alkenyl group having 2 to 10 carbon atoms, each of which may be substituted by one or more $R^1$ radicals, where one or more nonadjacent $CH_2$ groups may be replaced by O and where one or more hydrogen atoms may be replaced by D or F, an aromatic or heteroaromatic ring system which has 5 to 30 aromatic ring atoms and may be substituted in each case by one or more $R^1$ radicals, an aryloxy or heteroaryloxy group which has 5 to 30 aromatic ring atoms and may be substituted by one or more $R^1$ radicals, or a combination of these systems.

In a particularly preferred embodiment of the invention, R in the abovementioned formulae is the same or different at each instance and is selected from the group consisting of H, F, CN, a straight-chain alkyl group having 1 to 8 carbon atoms or a branched or cyclic alkyl group having 3 to 8 carbon atoms, each of which may be substituted by one or more $R^1$ radicals, where one or more hydrogen atoms may be replaced by D or F, an aromatic or heteroaromatic ring system which has 5 to 18 aromatic ring atoms and may be substituted in each case by one or more R¹ radicals, or a combination of these systems.

Suitable aromatic or heteroaromatic ring systems here are phenyl, ortho-, meta- or para-biphenyl, ortho-, meta-, para- or branched terphenyl, ortho-, meta-, para- or branched quaterphenyl, carbazole, indenocarbazole, indolocarbazole, triazine, pyrimidine, 1-, 2-, 3- or 4-fluorenyl, 1-, 2-, 3- or 4-spirobifluorenyl, 1-, 2-, 3- or 4-dibenzofuranyl, 1-, 2-, 3- or 4-dibenzothienyl or 1-, 2-, 3- or 4-carbazolyl, each of which may be substituted by one or more R¹ radicals.

When the compounds of the formula (1) or the preferred embodiments are used as electron transport material, it may be preferable for at least one of the R radicals to be an aromatic ring system or an electron-deficient heteroaromatic ring system. According to the invention, electron-deficient heteroaromatics are five-membered heteroaromatic rings having at least two heteroatoms or six-membered heteroaromatic rings, to each of which may be fused one or more aromatic or heteroaromatic groups.

When the compounds of the formula (1) or the preferred embodiments are used as matrix material for a phosphorescent emitter, it may be preferable for at least one of the R radicals to be a substituted or unsubstituted carbazole, indenocarbazole or indolocarbazole, each of which may be bonded via a carbon atom or a nitrogen atom. In that case, it is further preferable for the R, R¹ and R² radicals not to contain any fused aryl or heteroaryl groups in which more than two aromatic six-membered rings are fused directly to one another. More preferably, the R, R¹ and R² radicals also do not contain any fused aryl or heteroaryl groups in which two aromatic six-membered rings are fused directly to one another.

At the same time, for compounds which are processed by vacuum evaporation, the alkyl groups preferably have not more than five carbon atoms, more preferably not more than 4 carbon atoms, most preferably not more than 1 carbon atom.

The inventive compounds may also be rendered soluble by suitable substitution, for example by comparatively long alkyl groups (about 4 to 20 carbon atoms), especially branched alkyl groups, or optionally substituted aryl groups, for example xylyl or mesityl groups, or oligoarylene groups, for example ortho-, meta-, para- or branched terphenyl or quaterphenyl groups. Such compounds are then soluble in sufficient concentration at room temperature in standard organic solvents, for example toluene or xylene, to be able to process the compounds from solution. These soluble compounds are of particularly good suitability for processing from solution, for example by printing methods.

For the processing of the inventive compounds from the liquid phase, for example by spin-coating or by printing methods, formulations of the inventive compounds are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (-)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore further provides a formulation, especially a solution or dispersion, comprising at least one compound of formula (1) or the preferred embodiments detailed above and at least one further compound, especially a solvent. In this case, the formulation composed of the compound of formula (1) and the solvent(s) may also comprise further compounds, for example emitters.

Examples of preferred compounds according to the above-detailed embodiments are the compounds of the following structures:

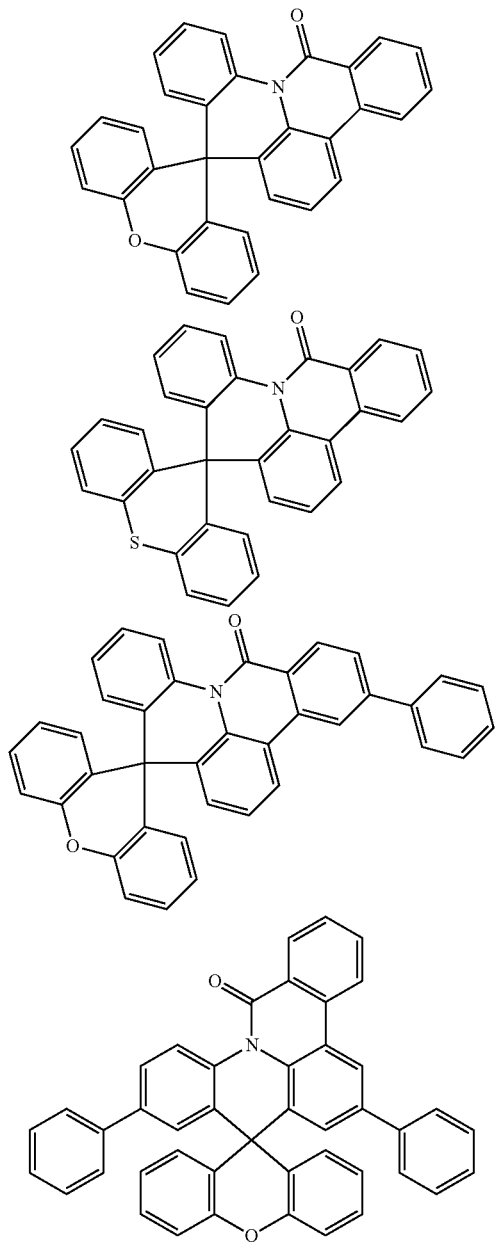

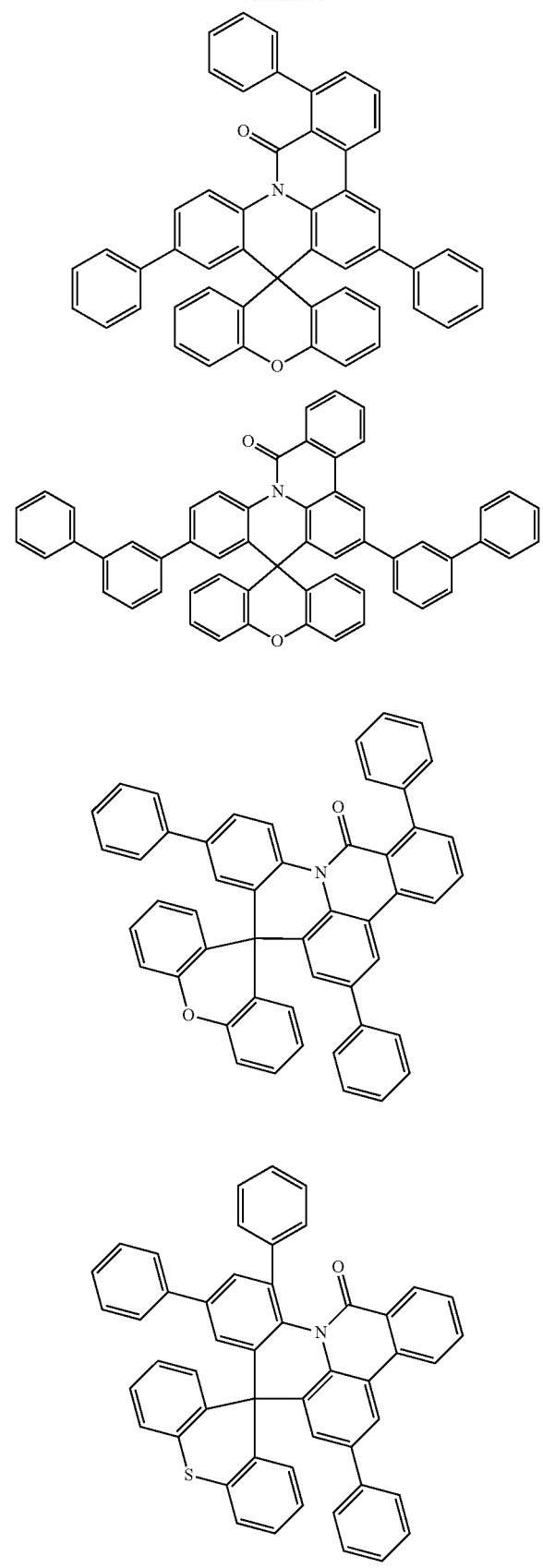
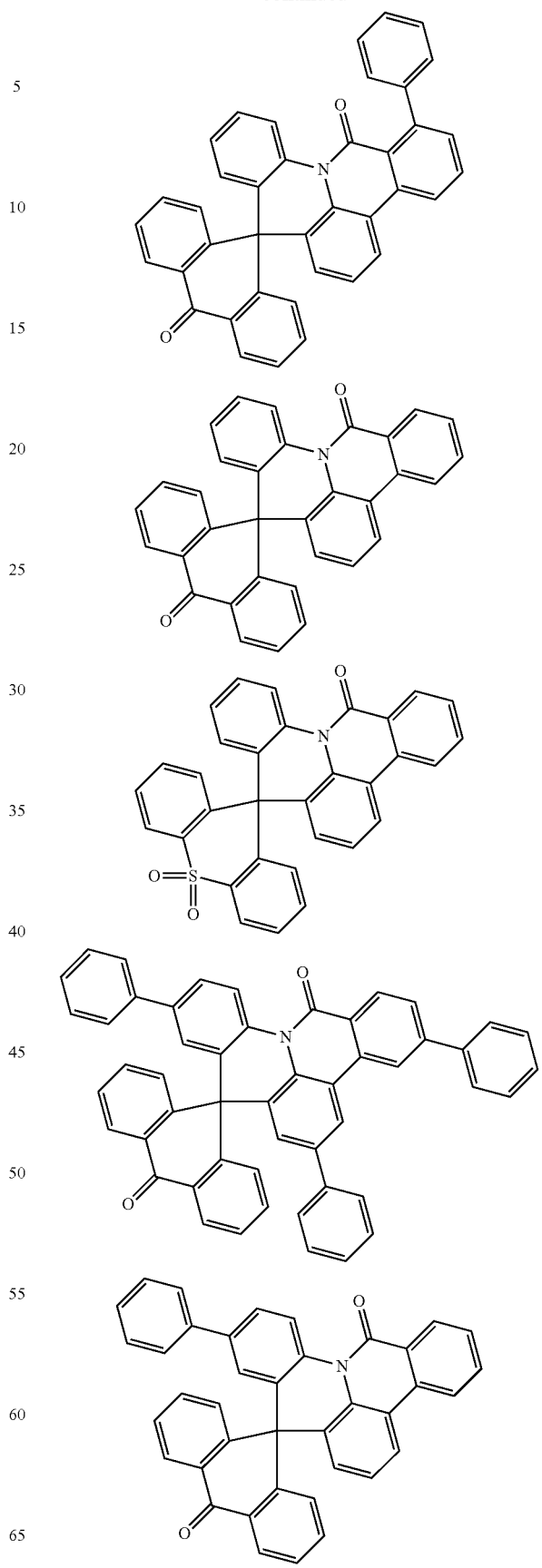

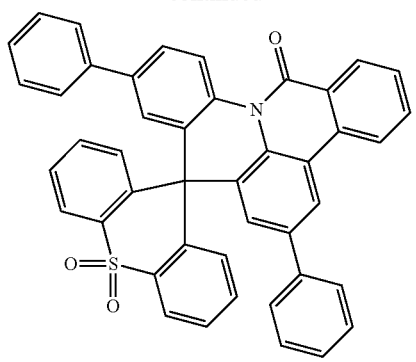
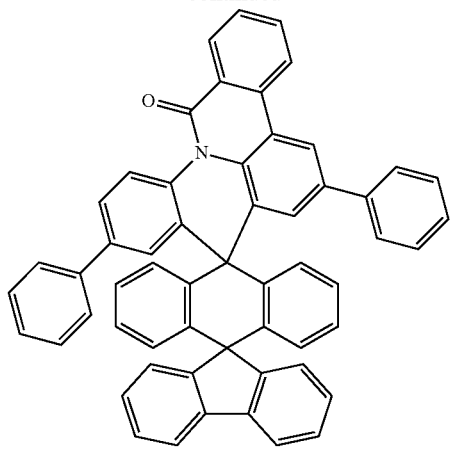
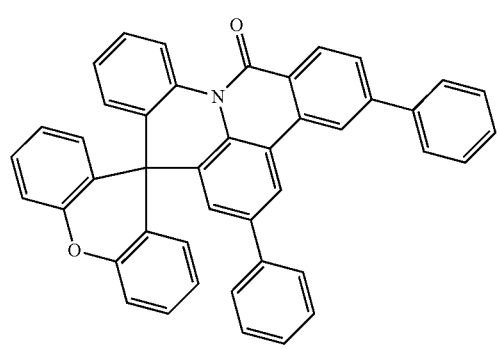
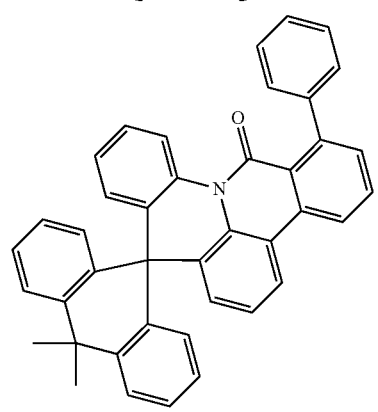
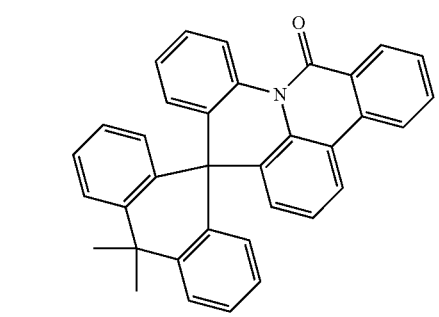
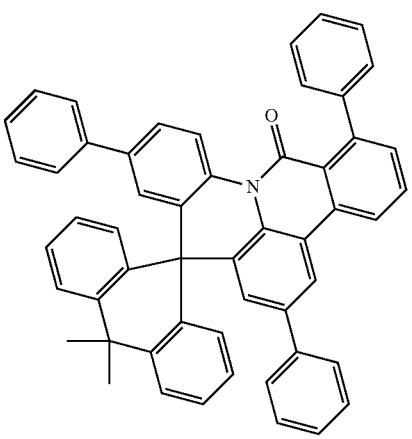
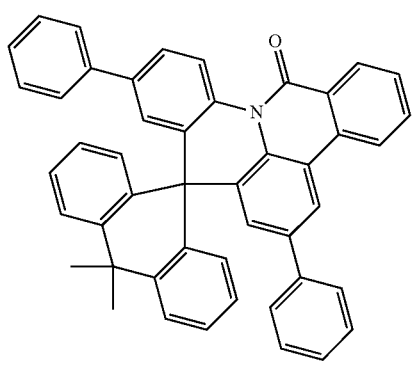
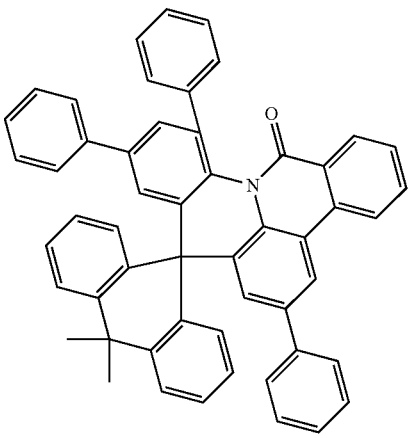

-continued
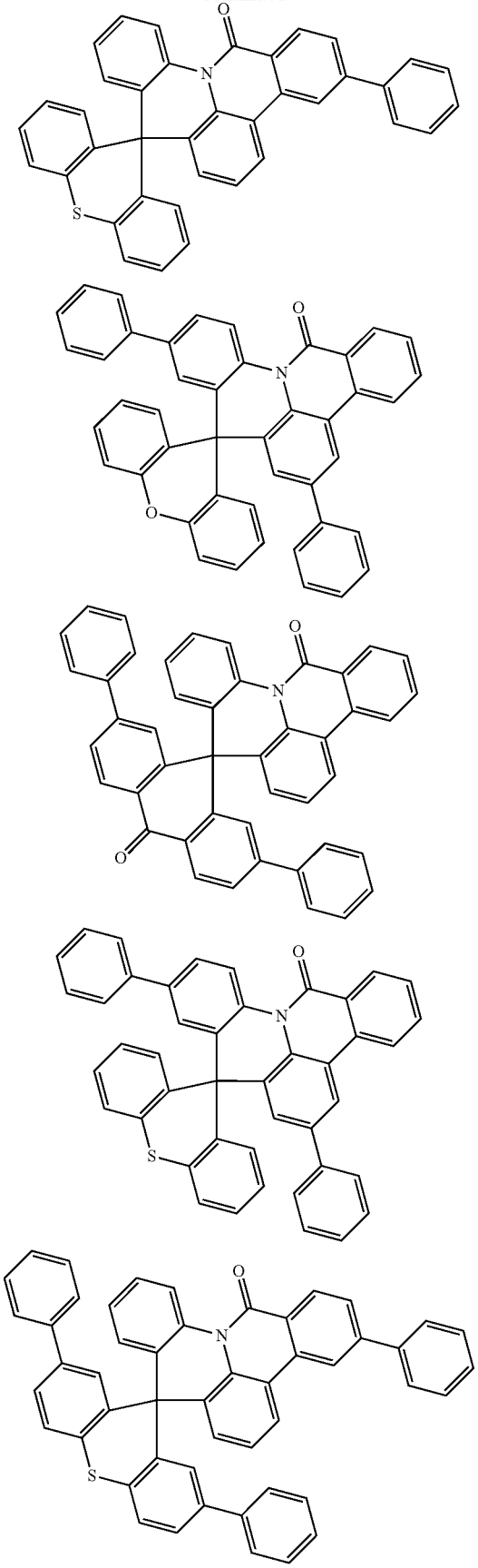
-continued
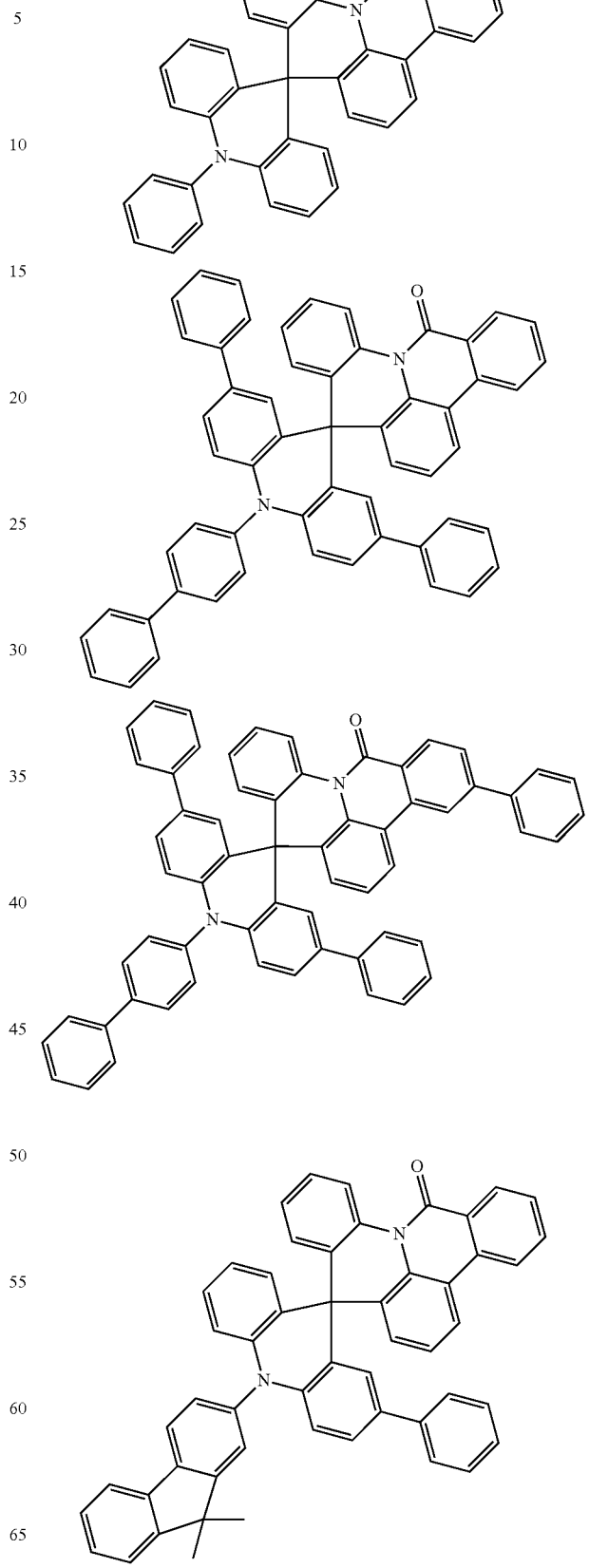

-continued
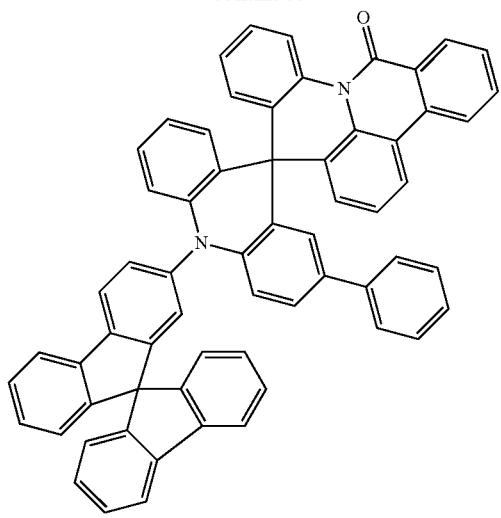
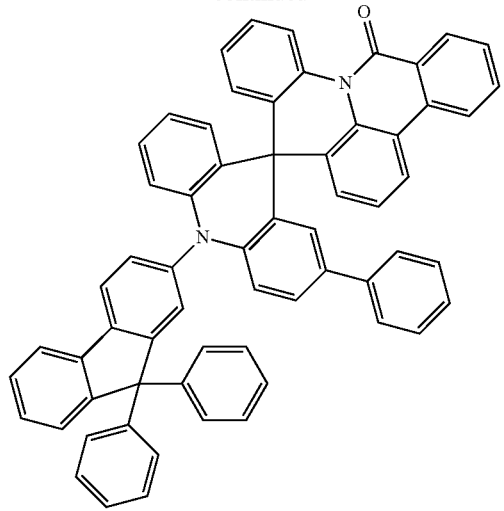
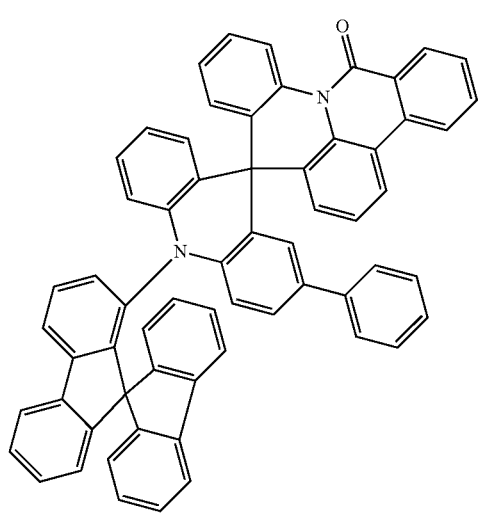
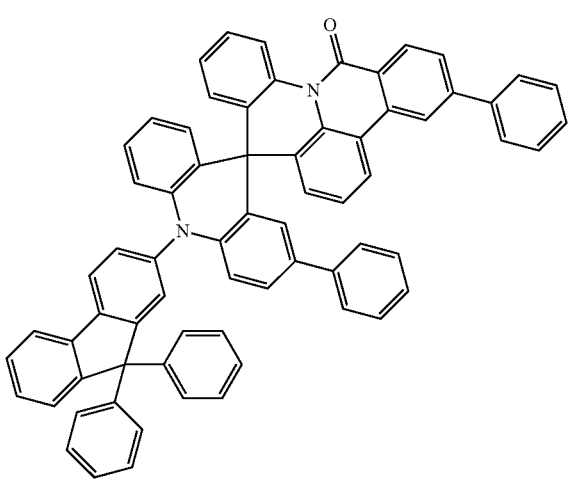
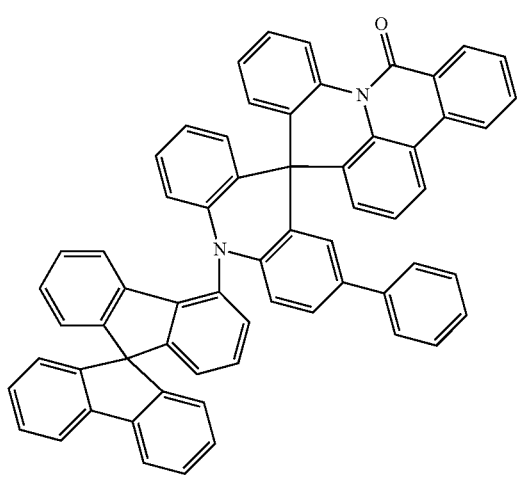
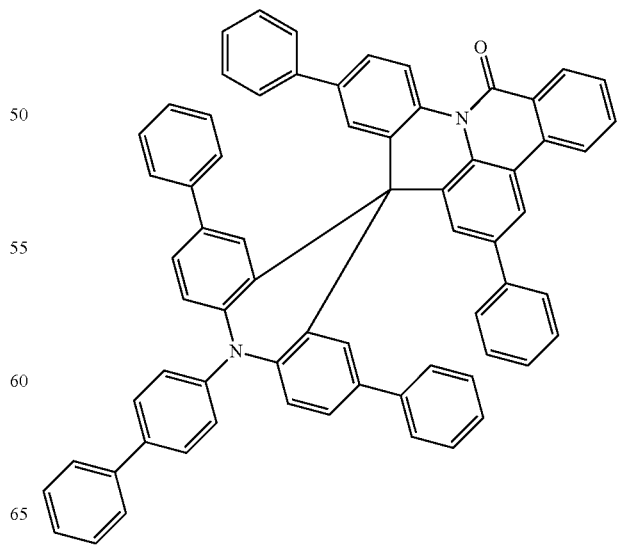

31
-continued
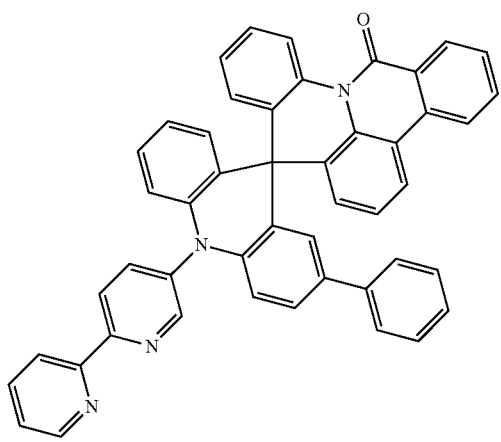
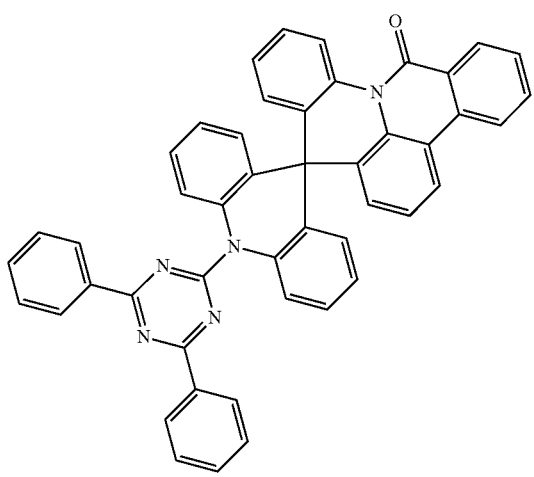
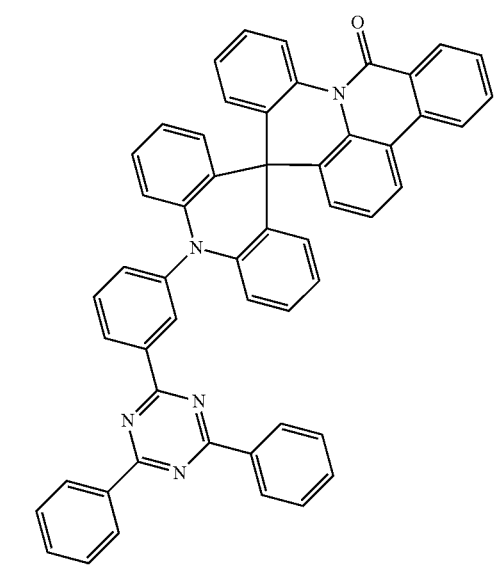
32
-continued
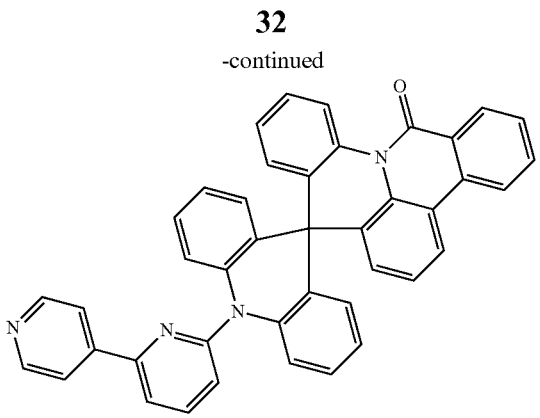
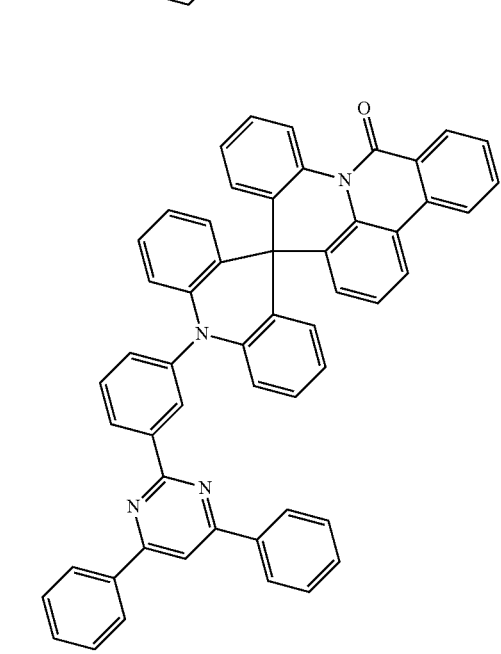
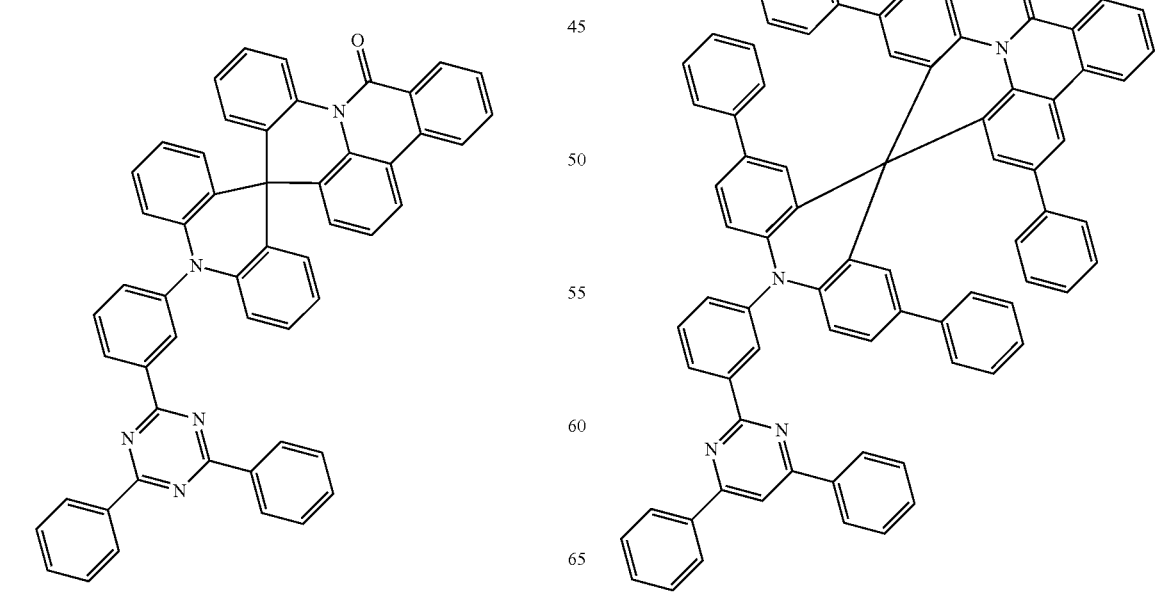

33
-continued
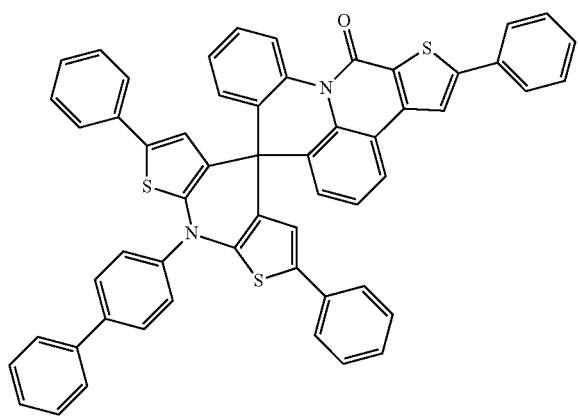
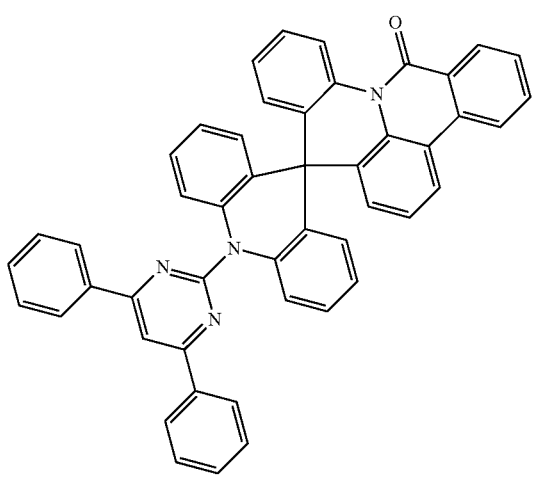
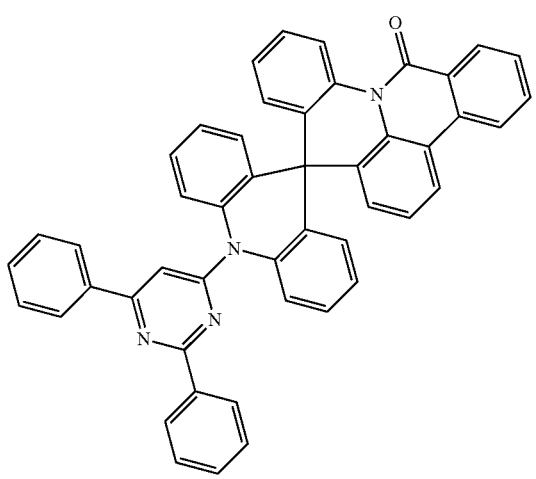
34
-continued
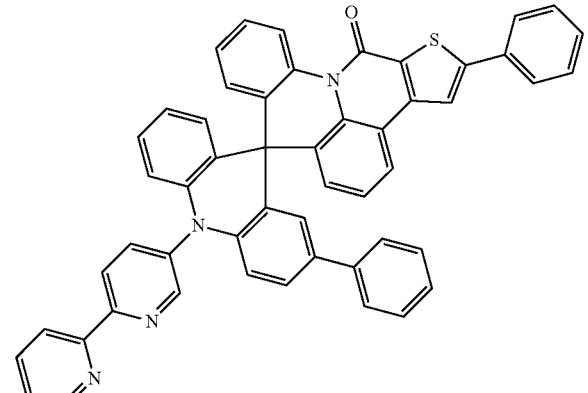
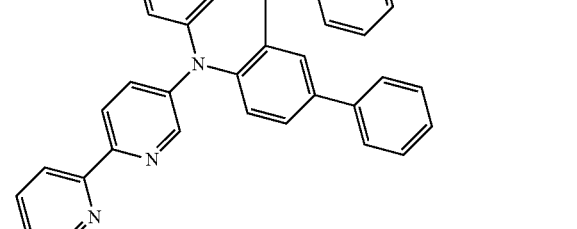
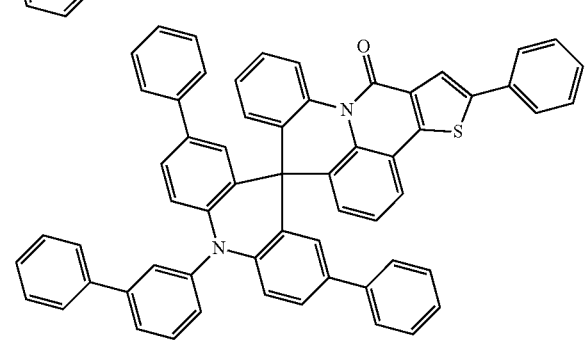
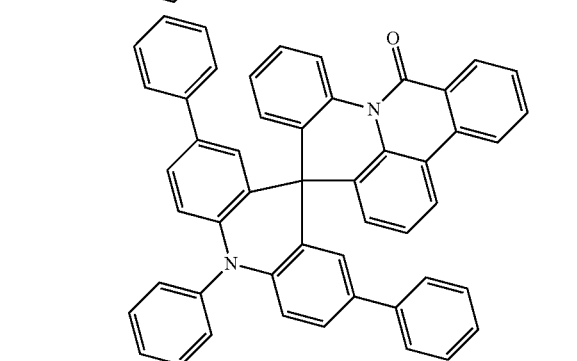
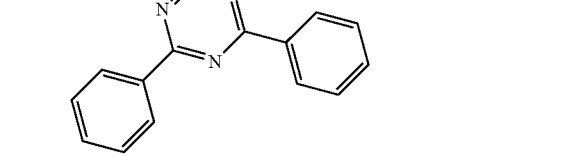

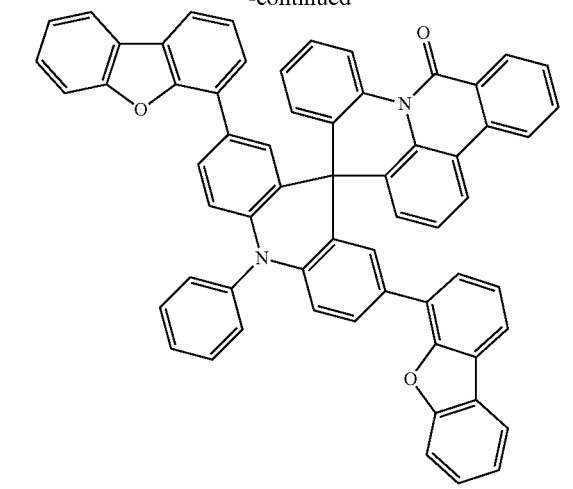
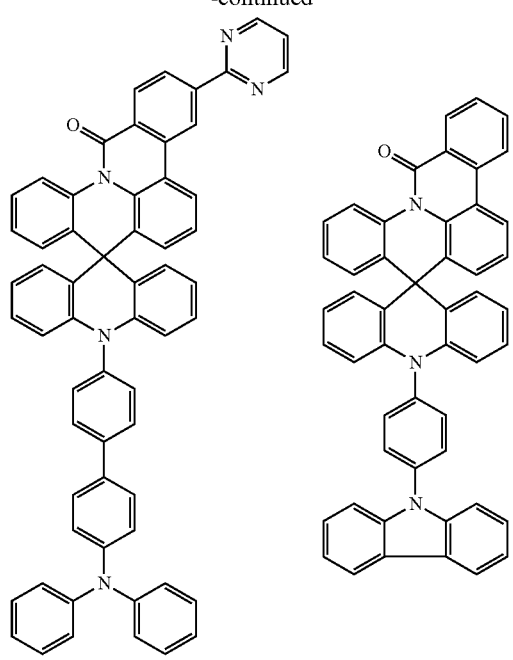
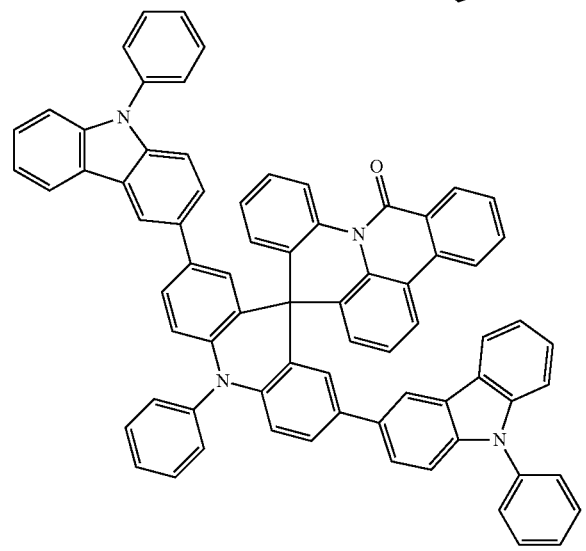
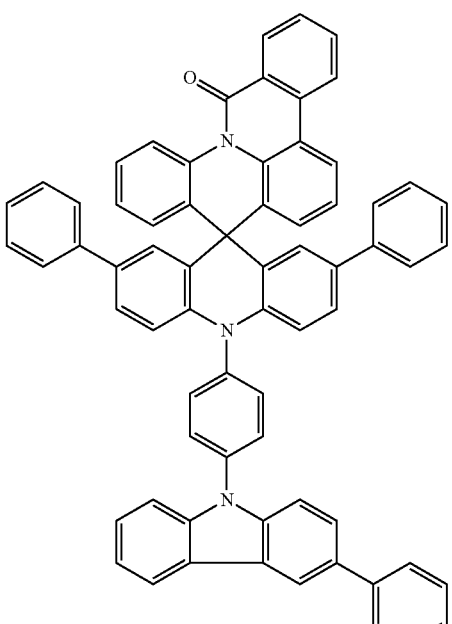

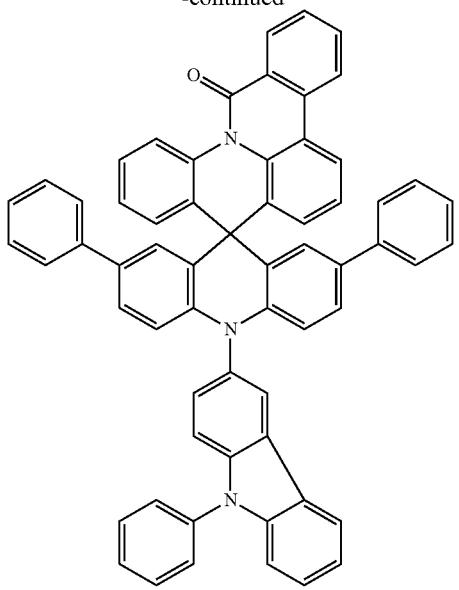
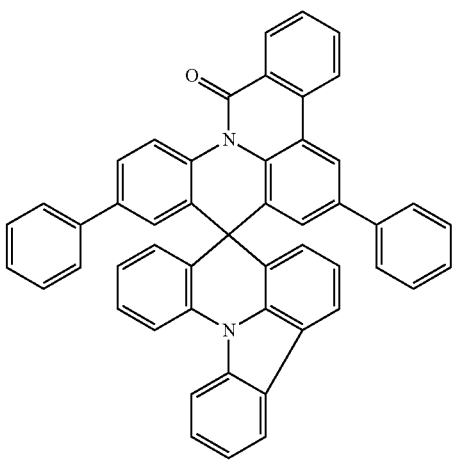
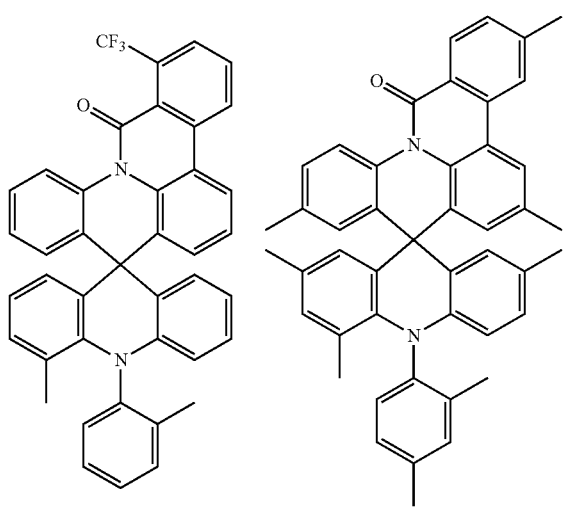
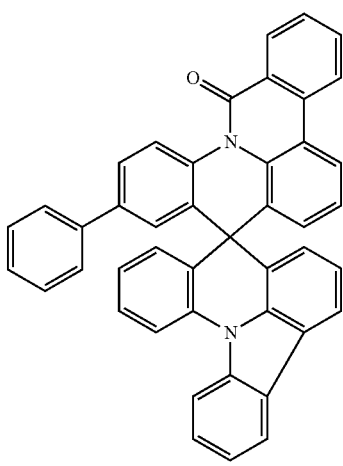
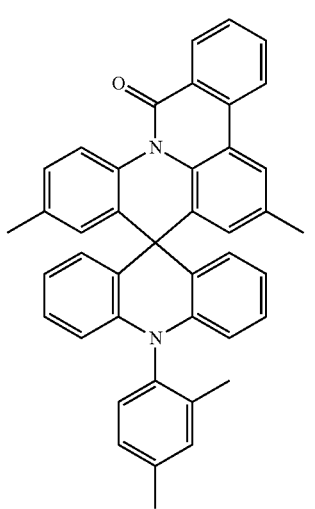
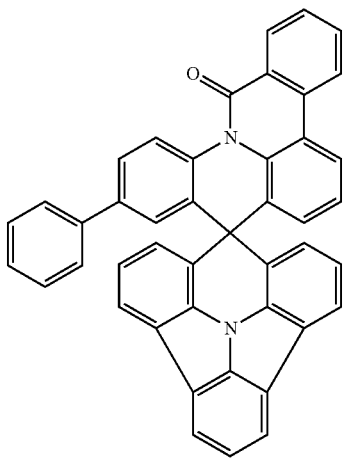

-continued
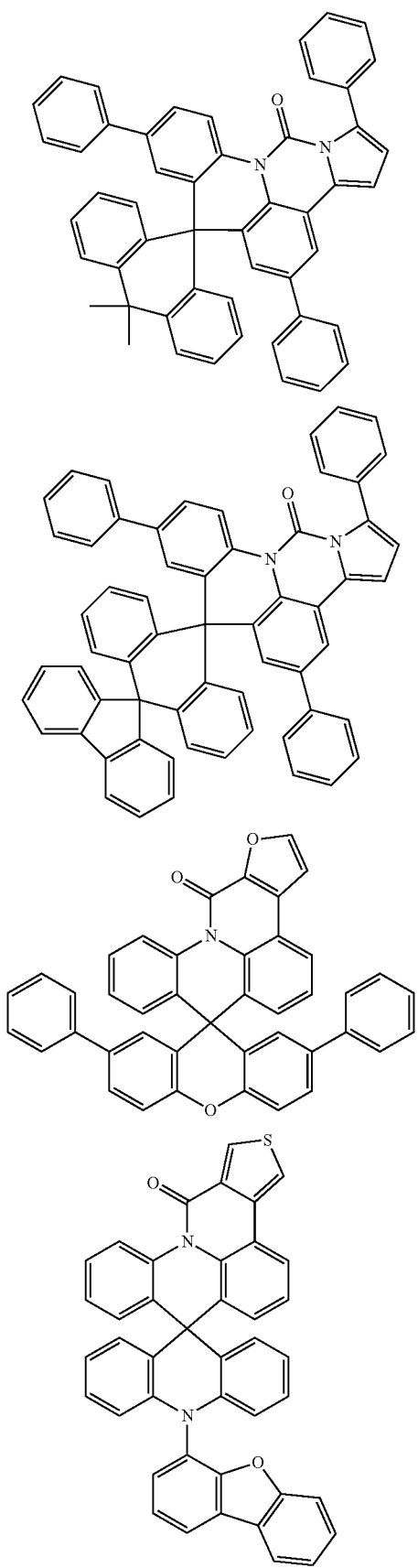
-continued
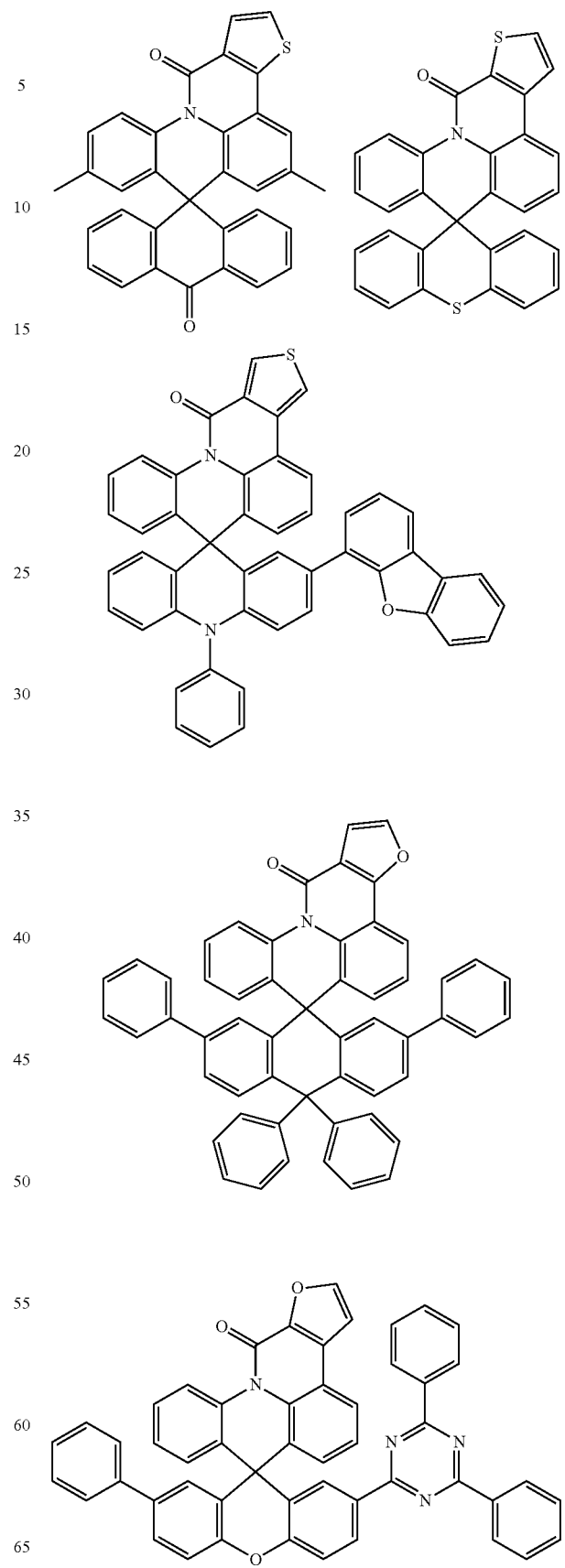

41
-continued
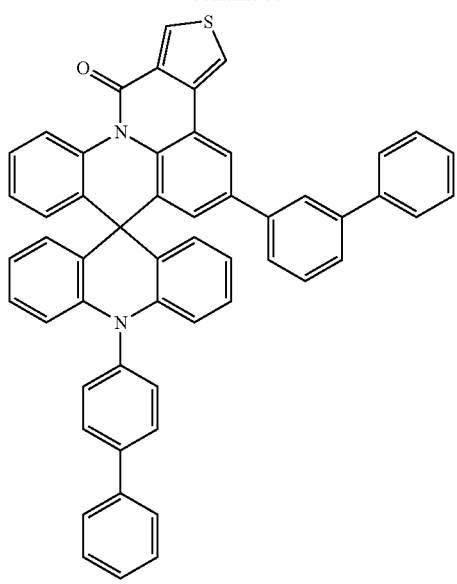
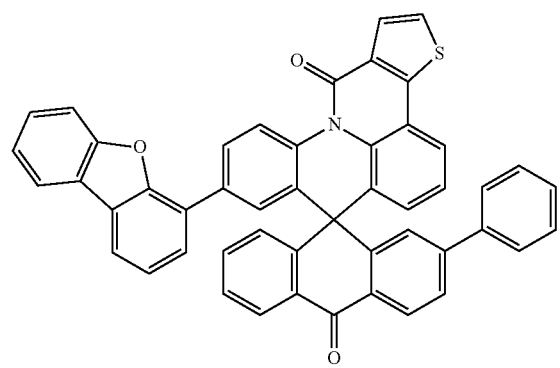
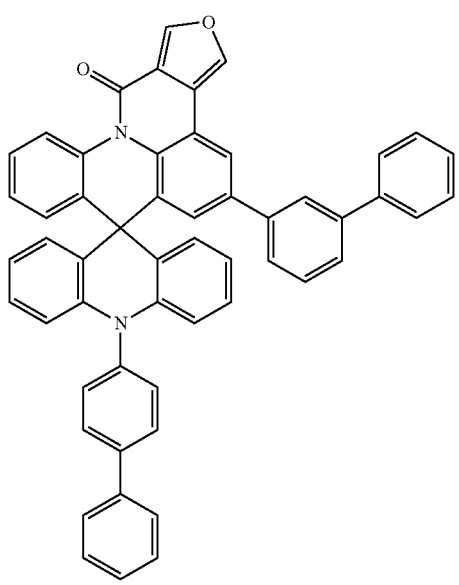
42
-continued
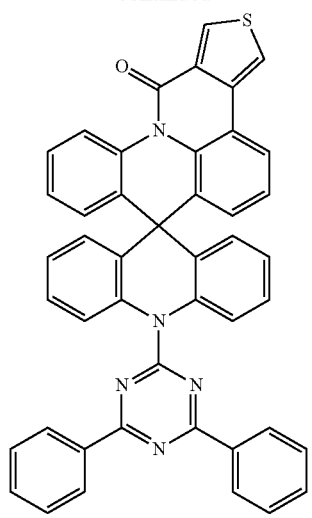
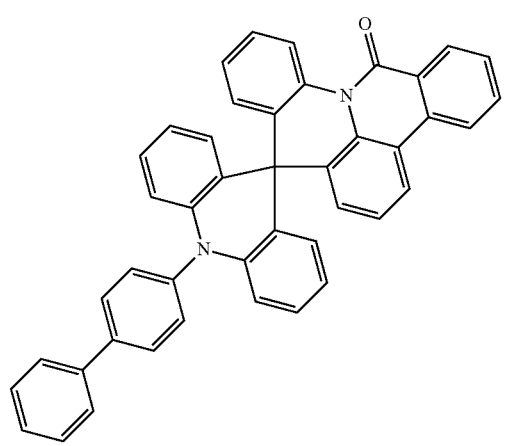
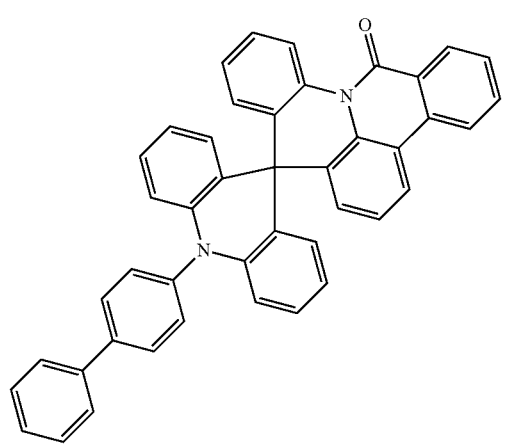

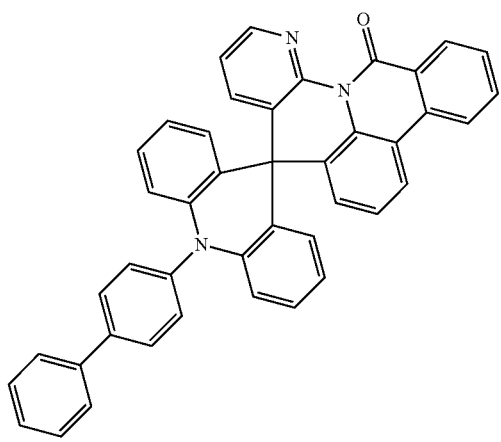
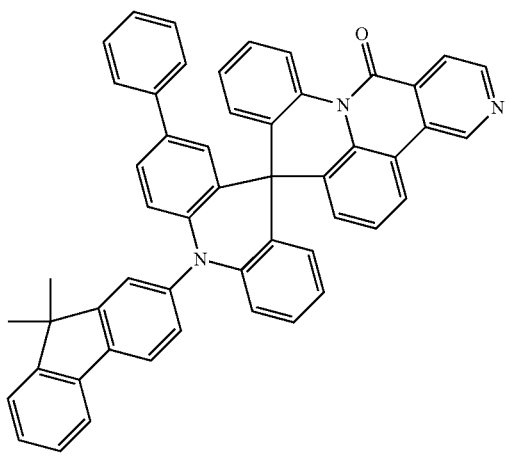
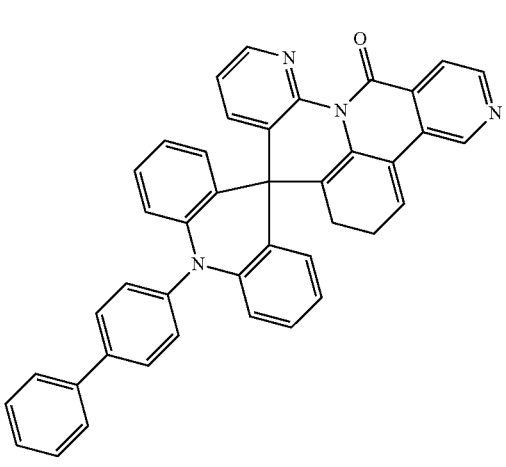
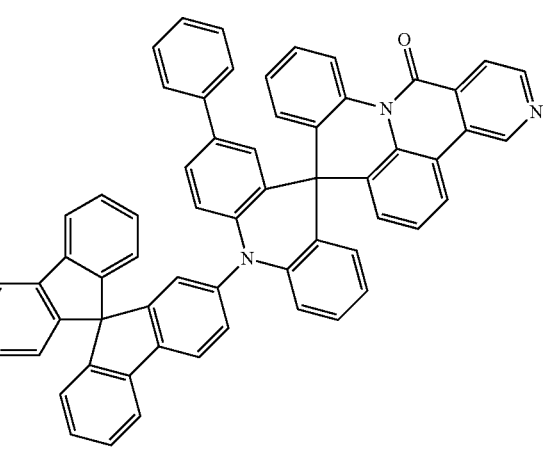
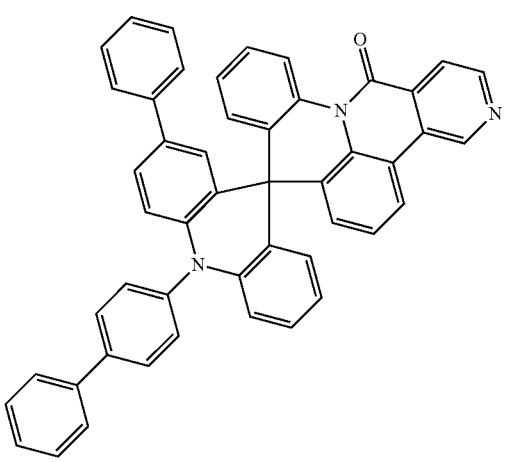
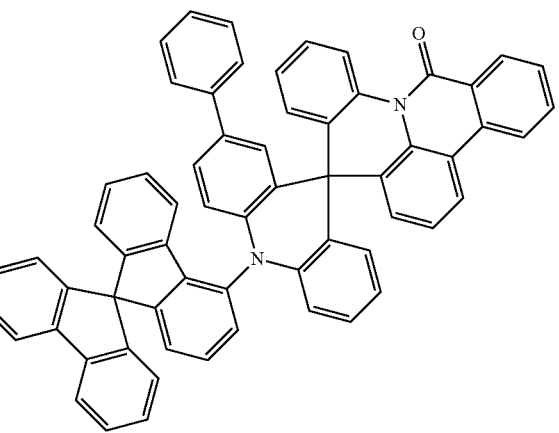

-continued
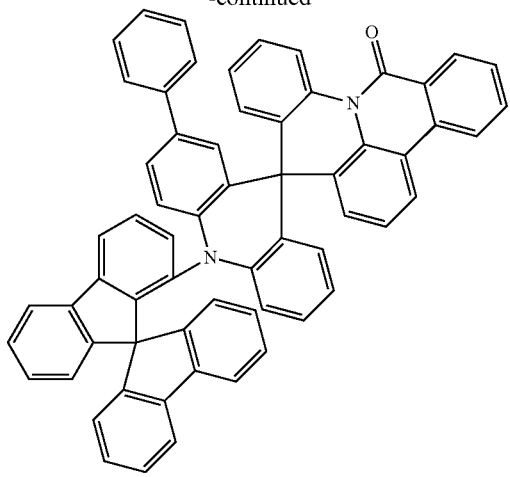
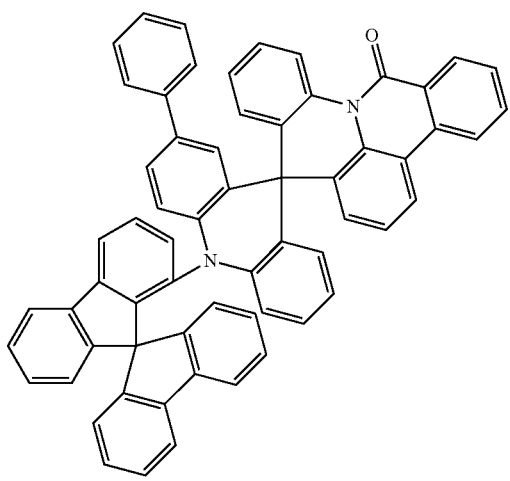
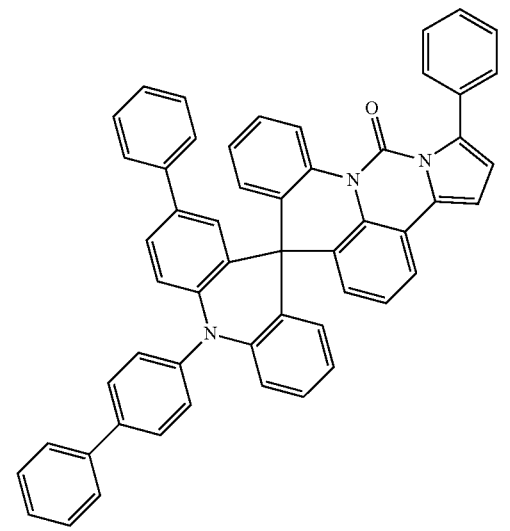
-continued
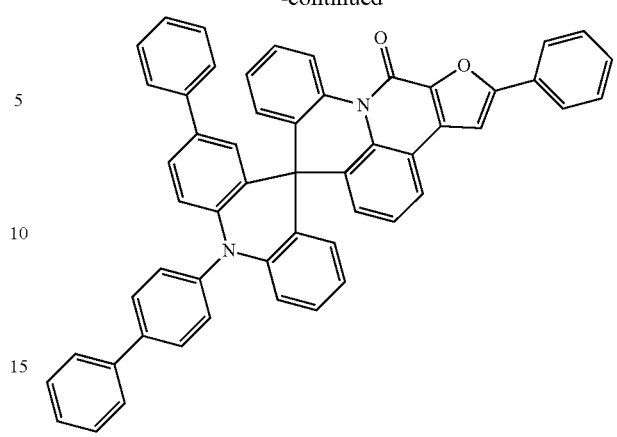
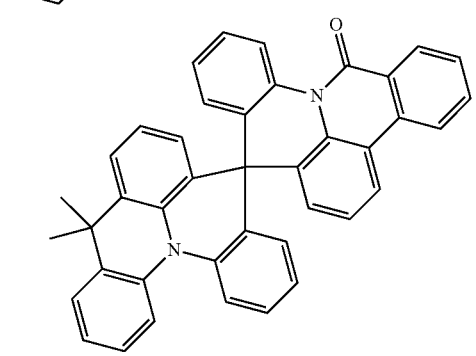
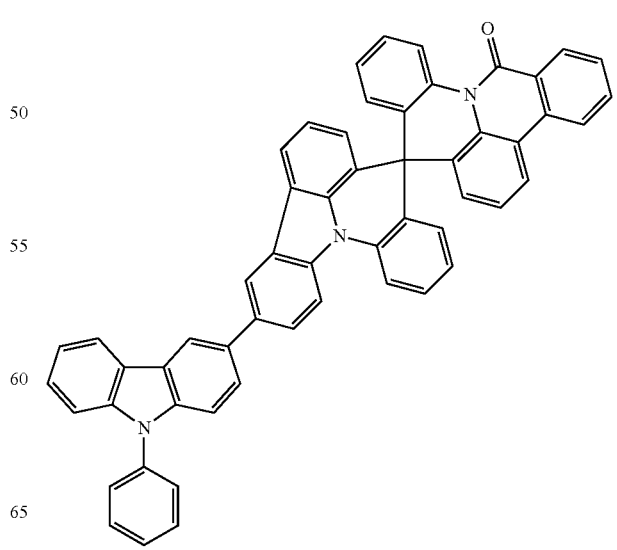

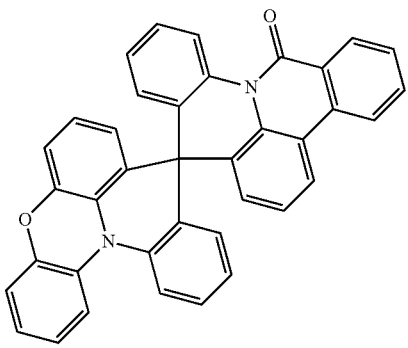
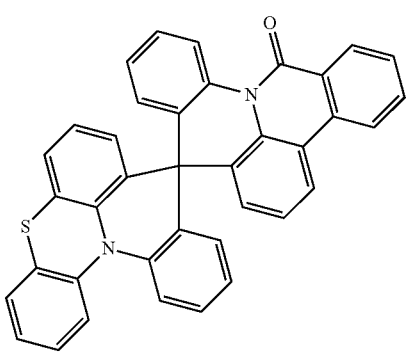
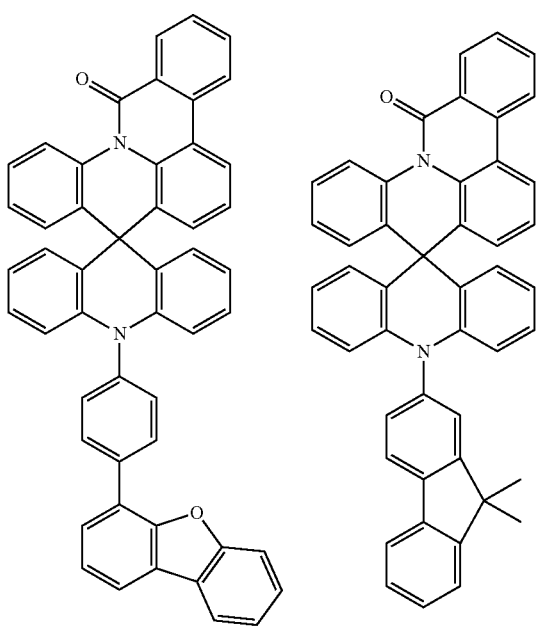
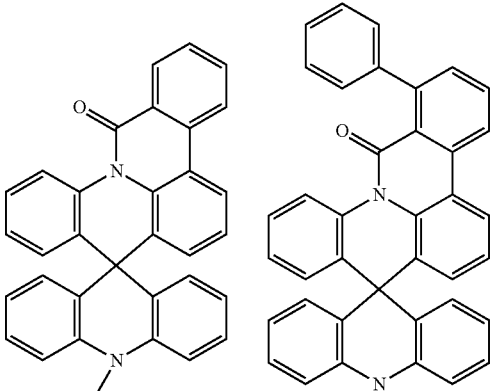
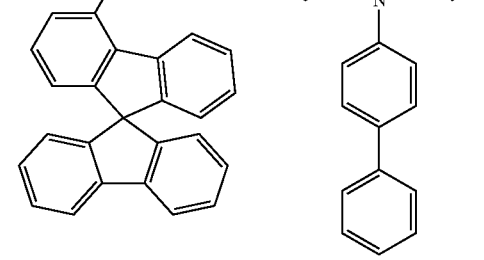
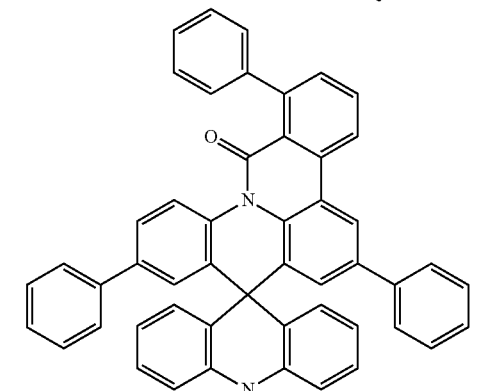
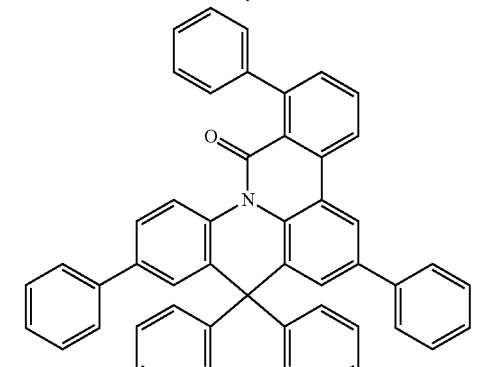

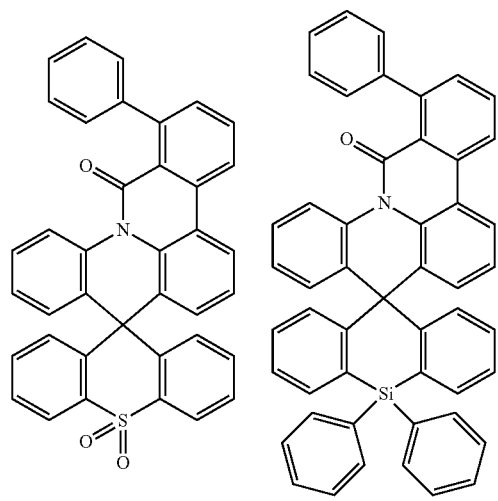
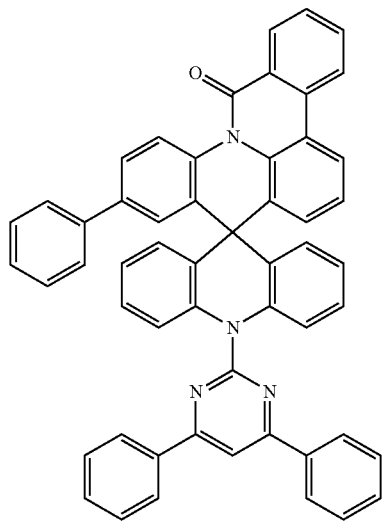
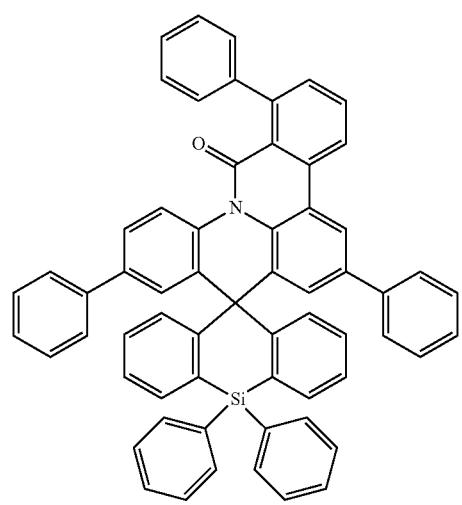
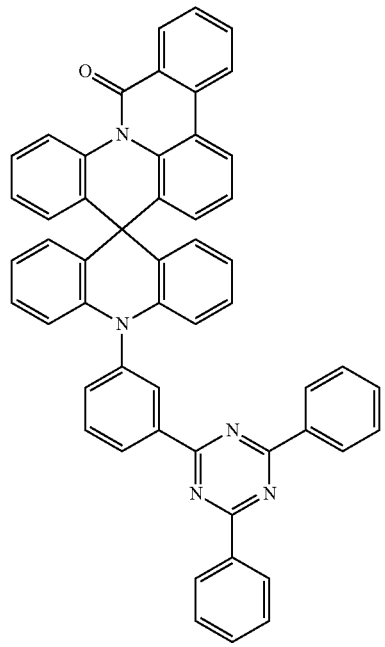
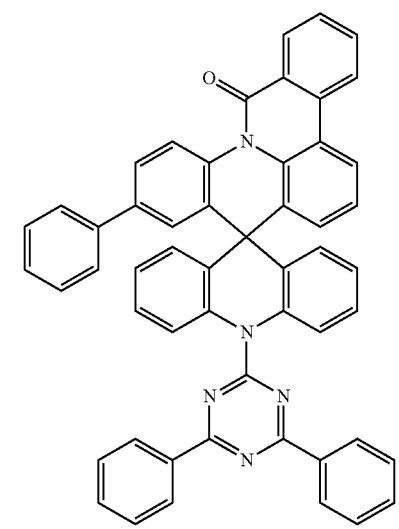
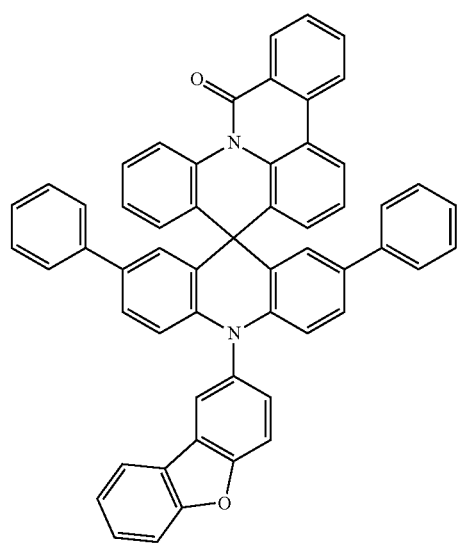

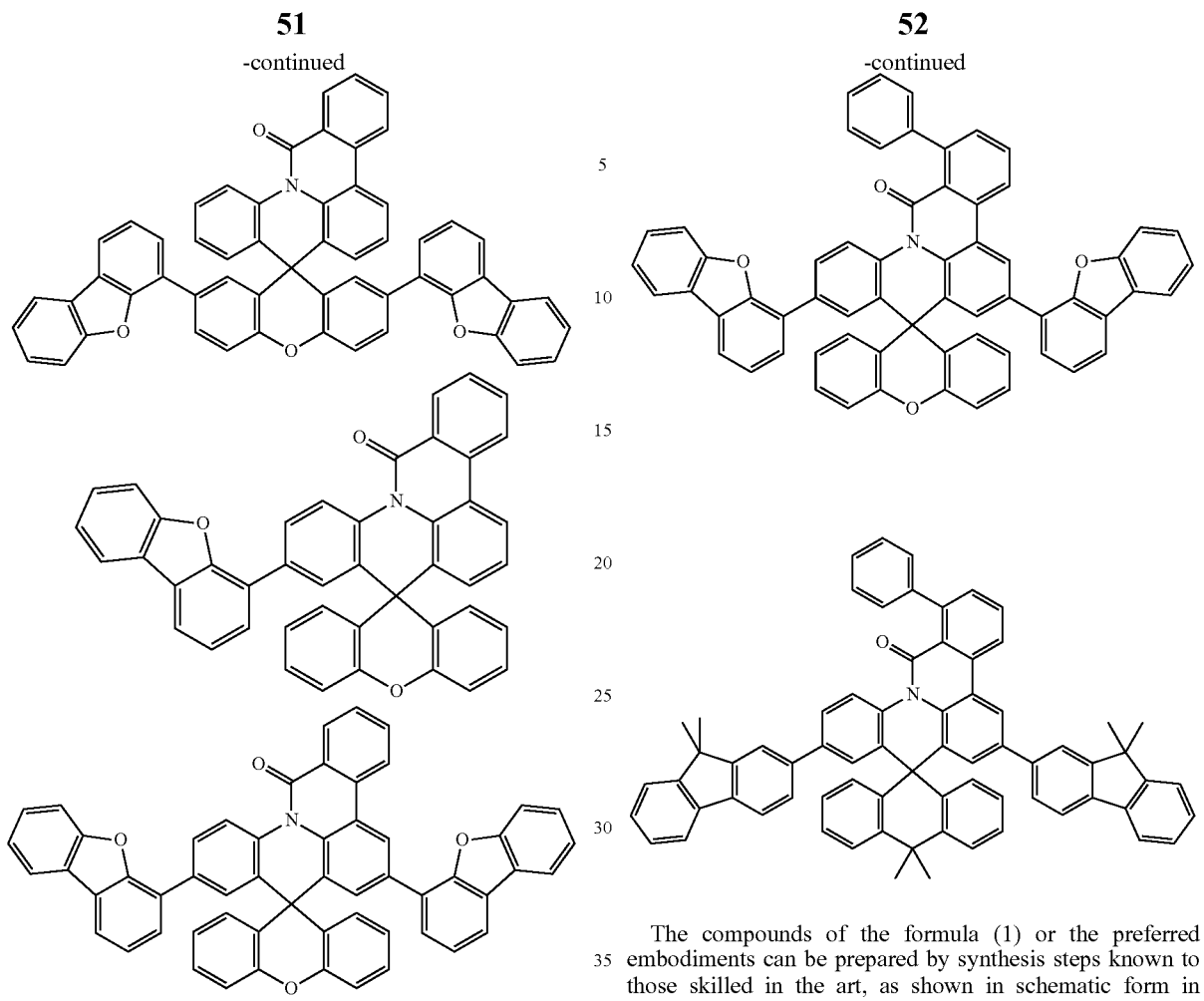
The compounds of the formula (1) or the preferred embodiments can be prepared by synthesis steps known to those skilled in the art, as shown in schematic form in schemes 1 and 2.
Scheme 1
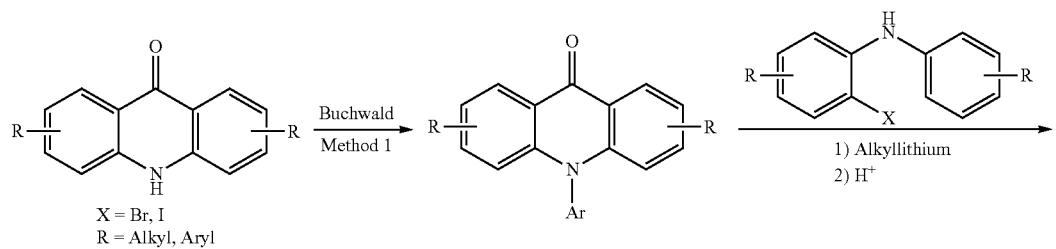
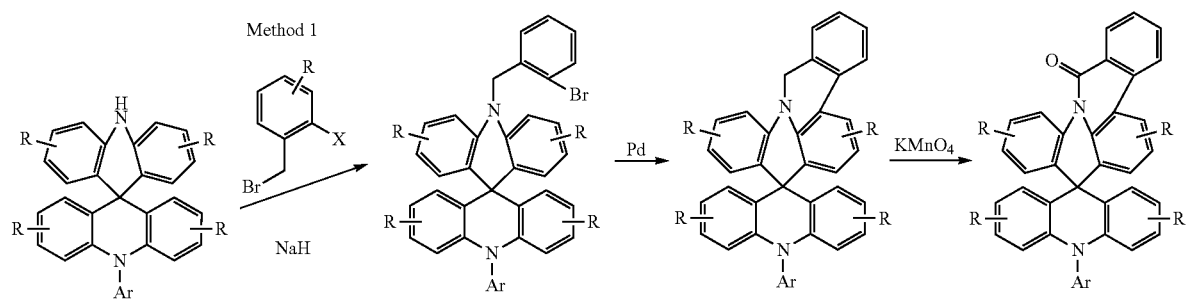

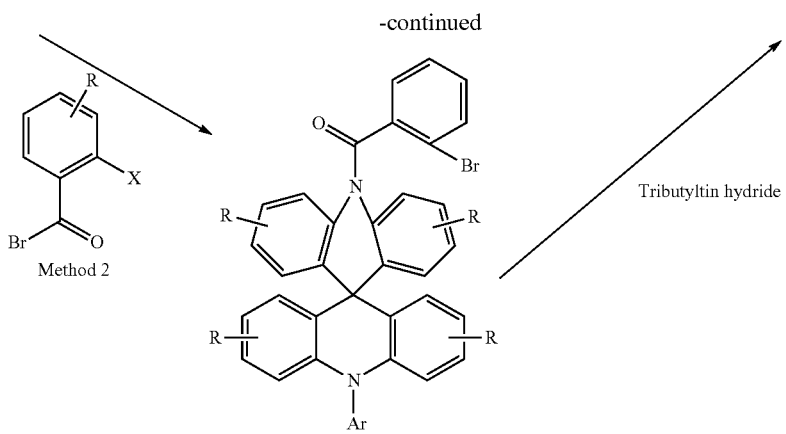

The functionalized spiroacridine compounds are the central unit for the further functionalization, as shown in scheme 1. It is thus possible to prepare these functionalized compounds easily by reaction of the corresponding acridines with ortho-brominated arylamines by lithiation and acid-catalyzed cyclization.

The spiroacridine compounds may be deprotonated with a base, for example NaH, and nucleophilically substituted by reaction with a benzyl halide. Subsequent palladium-catalyzed cyclization followed by oxidation leads to the inventive compounds. A further option is reaction with an ortho-halogenated aromatic acid halide and subsequent cyclization, which likewise leads to the inventive compounds.

In entirely analogous manner, it is also possible to use xanthones, thioxanthenone or an anthracen-9-one derivative in place of acridine (scheme 2).

Scheme 2

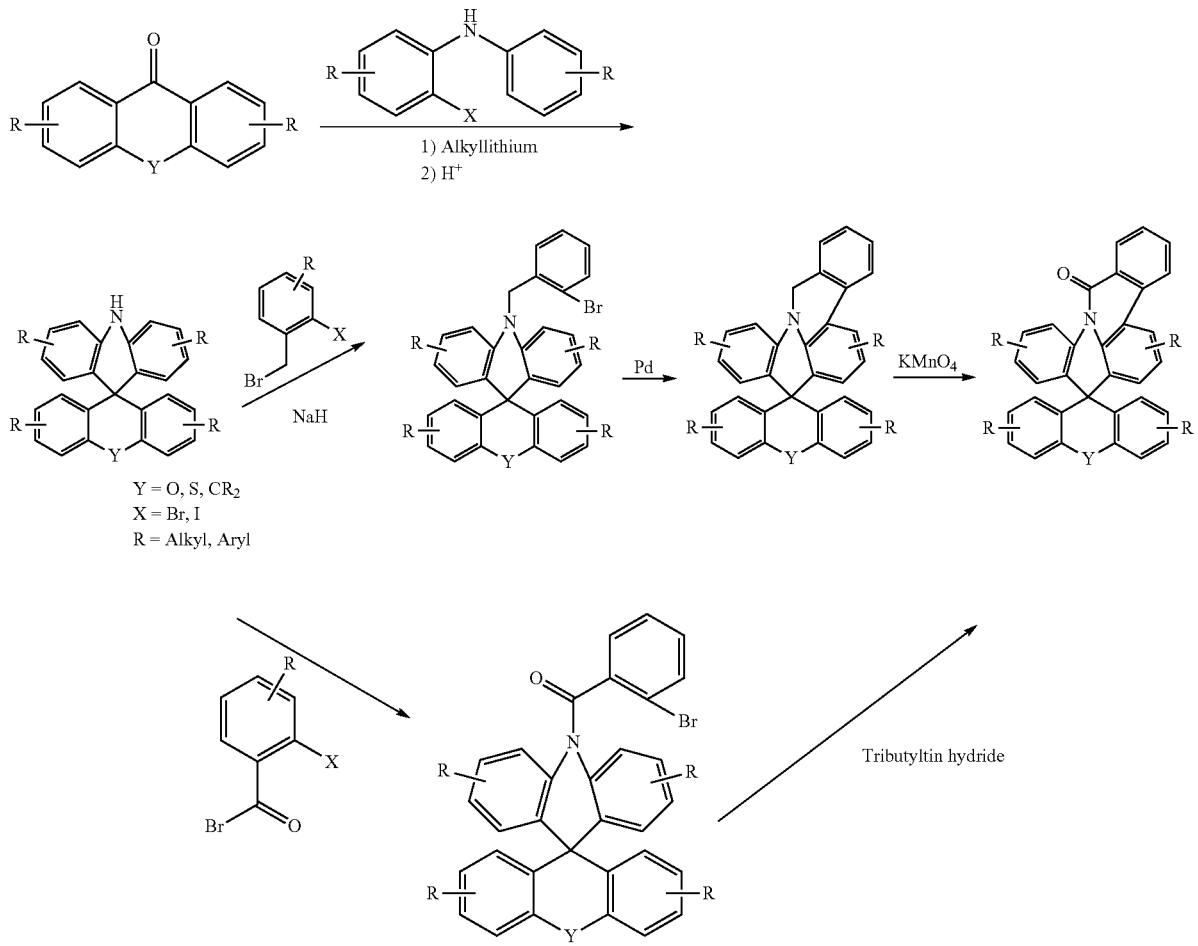

The present invention therefore further provides a process for preparing a compound of formula (1), comprising the reaction steps of:

a) preparing a spiro compound proceeding from an acridine, xanthone, thioxanthenone or anthracen-9-one derivative; and
b) substituting the nitrogen, followed by cyclizing to give the lactam.

The above-described inventive compounds, especially compounds substituted by reactive leaving groups, such as bromine, iodine, chlorine, boronic acid or boronic ester, or by reactive polymerizable groups such as olefins or oxetanes, may find use as monomers for production of corresponding oligomers, dendrimers or polymers. The oligomerization or polymerization is preferably effected via the halogen functionality or the boronic acid functionality or via the polymerizable group. It is additionally possible to crosslink the polymers via groups of this kind. The inventive compounds and polymers may be used in the form of a crosslinked or uncrosslinked layer.

The invention therefore further provides oligomers, polymers or dendrimers containing one or more of the above-detailed inventive compounds, wherein one or more bonds of the inventive compound to the polymer, oligomer or dendrimer are present. According to the linkage of the inventive compound, it therefore forms a side chain of the oligomer or polymer or is incorporated in the main chain. The polymers, oligomers or dendrimers may be conjugated, partly conjugated or nonconjugated. The oligomers or polymers may be linear, branched or dendritic. For the repeat units of the inventive compounds in oligomers, dendrimers and polymers, the same preferences apply as described above.

For preparation of the oligomers or polymers, the monomers of the invention are homopolymerized or copolymerized with further monomers. Preference is given to homopolymers or copolymers wherein the units of formula (1) or the above-recited preferred embodiments are present to an extent of 0.01 to 99.9 mol %, preferably 5 to 90 mol %, more preferably 20 to 80 mol %. Suitable and preferred comonomers which form the polymer base skeleton are chosen from fluorenes (for example according to EP 842208 or WO 2000/22026), spirobifluorenes (for example according to EP 707020, EP 894107 or WO 2006/061181), paraphenylenes (for example according to WO 92/18552), carbazoles (for example according to WO 2004/070772 or WO 2004/113468), thiophenes (for example according to EP 1028136), dihydrophenanthrenes (for example according to WO 2005/014689), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers may contain still further units, for example hole transport units, especially those based on triarylamines, and/or electron transport units. In addition, the polymers may contain triplet emitters either in copolymerized form or mixed into a blend. Specifically the combination of units of formula (1) or the above-recited preferred embodiments with triplet emitters leads to particularly good results.

In addition, the compounds of formula (1) or the above-recited preferred embodiments may also be further functionalized and thus be converted to extended structures. Examples here include the Suzuki reaction with arylboronic acids or the Hartwig-Buchwald reaction with primary or secondary amines. Thus, the compounds of formula (1) or the above-recited preferred embodiments may also be bonded directly to phosphorescent metal complexes or else to other metal complexes.

The inventive compound can be used in an electronic device. The present invention therefore further provides for the use of a compound of formula (1) or the above-detailed preferred embodiments in an electronic device, especially in an organic electroluminescent device.

An electronic device in the context of present invention is a device comprising at least one layer comprising at least one organic compound. This component may also comprise inorganic materials or else layers formed entirely from inorganic materials.

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells (O-DSSCs), organic optical detectors, organic photoreceptors, organic field-quench devices (O-FQDs), light-emitting electrochemical cells (LECs), organic laser diodes (O-lasers) and organic plasmon emitting devices (D. M. Koller et al., *Nature Photonics* 2008, 1-4), but preferably organic electroluminescent devices (OLEDs), more preferably phosphorescent OLEDs.

The organic electroluminescent device comprises cathode, anode and at least one emitting layer. Apart from these layers, it may comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily each of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers show blue, green and orange or red emission (for the basic construction see, for example, WO 2005/011013).

The inventive compound according to the above-detailed embodiments may be used in different layers, according to the exact structure. Preference is given to an organic electroluminescent device comprising a compound of formula (1) or the above-recited preferred embodiments as matrix material for fluorescent or phosphorescent emitters, especially for phosphorescent emitters, and/or in a hole blocker layer and/or in an electron transport layer and/or in an electron-blocking or exciton-blocking layer and/or in a hole transport layer, according to the exact substitution.

In a preferred embodiment of the invention, the compound of formula (1) or the above-recited preferred embodiments is used as matrix material for a fluorescent or phosphorescent compound, especially for a phosphorescent compound, in an emitting layer. In this case, the organic electroluminescent device may contain an emitting layer, or it may contain a plurality of emitting layers, where at least one emitting layer contains at least one inventive compound as matrix material.

When the compound of formula (1) or the above-recited preferred embodiments is used as matrix material for an emitting compound in an emitting layer, it is preferably used in combination with one or more phosphorescent materials (triplet emitters). Phosphorescence in the context of this invention is understood to mean luminescence from an excited state having higher spin multiplicity, i.e. a spin state >1, especially from an excited triplet state. In the context of this application, all luminescent complexes with transition metals or lanthanides, especially all iridium, platinum and copper complexes, shall be regarded as phosphorescent compounds.

The mixture of the compound of formula (1) or the above-recited preferred embodiments and the emitting compound contains between 99% and 1% by volume, preferably between 98% and 10% by volume, more preferably between 97% and 60% by volume and especially between 95% and 80% by volume of the compound of formula (1) or the above-recited preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material.

A further preferred embodiment of the present invention is the use of the compound of formula (1) or the above-recited preferred embodiments as matrix material for a phosphorescent emitter in combination with a further matrix material. In this case, the further matrix material may be hole-transporting or electron-transporting, or it may be a matrix material which has a large band gap and is thus involved neither in hole transport nor in electron transport. Particularly suitable matrix materials which can be used in combination with the inventive compounds are aromatic ketones, aromatic phosphine oxides or aromatic sulfoxides or sulfones, for example according to WO 2004/013080, WO 2004/093207, WO 2006/005627 or WO 2010/006680, triarylamines, carbazole derivatives, e.g. CBP (N,N-biscarbazolylbiphenyl) or the carbazole derivatives disclosed in WO 2005/039246, US 2005/0069729, JP 2004/288381, EP 1205527, WO 2008/086851 or the unpublished application EP 11007693.2, indolocarbazole derivatives, for example according to WO 2007/063754 or WO 2008/056746, indenocarbazole derivatives, for example according to WO 2010/136109 or WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2007/063754, WO 2008/056746, WO 2010/015306, WO 2011/057706, WO 2011/060859 or WO 2011/060877, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to WO 2011/042107, WO 2011/060867, WO 2011/088877 and WO 2012/143080, or triphenylene derivatives, for example according to WO 2012/048781. It is likewise possible for a further phosphorescent emitter having shorter-wavelength emission than the actual emitter to be present as co-host in the mixture, or a compound not involved in charge transport to a significant extent, if at all, as described, for example, in WO 2010/108579.

Suitable phosphorescent compounds (=triplet emitters) are especially compounds which, when suitably excited, emit light, preferably in the visible region, and also contain at least one atom of atomic number greater than 20, preferably greater than 38, and less than 84, more preferably greater than 56 and less than 80, especially a metal having this atomic number. Preferred phosphorescence emitters used are compounds containing copper, molybdenum, tungsten, rhenium, ruthenium, osmium, rhodium, iridium, palladium, platinum, silver, gold or europium, especially compounds containing iridium, platinum or copper. When the compounds contain Ir or Pt, they preferably contain at least one ligand which coordinates to the metal via a carbon atom and a nitrogen or oxygen atom.

Examples of the above-described emitters can be found in applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

Examples of suitable phosphorescent emitters are the compounds detailed in the following table:

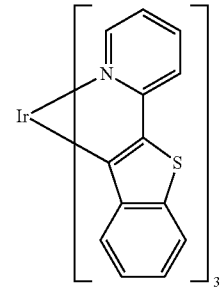

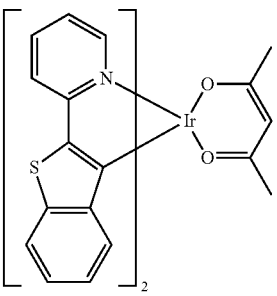

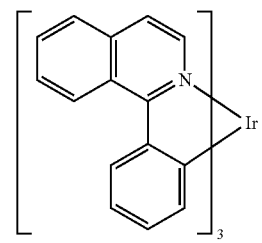

-continued
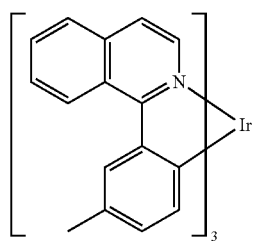
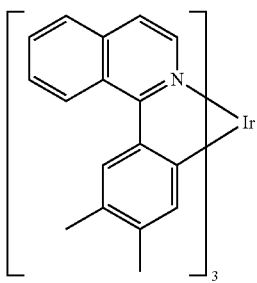
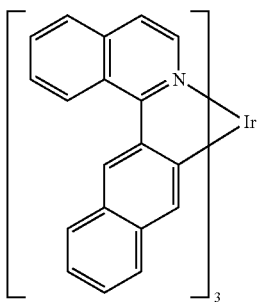
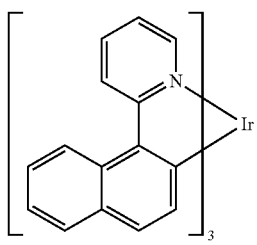
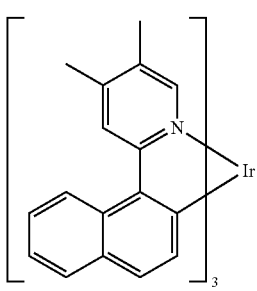
-continued
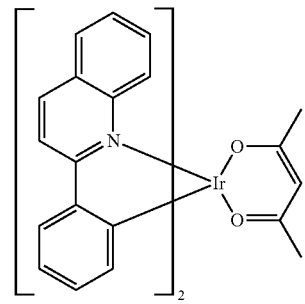
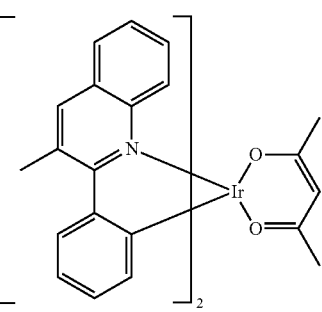
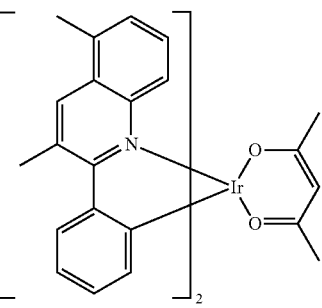
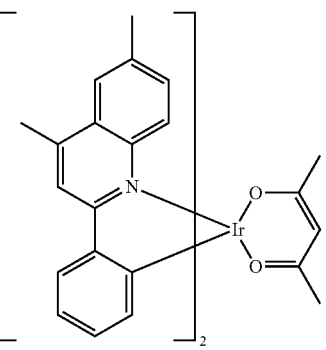
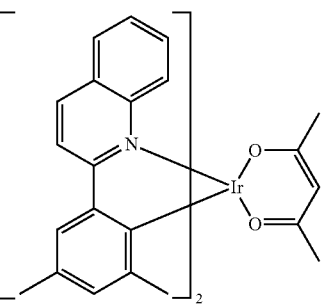

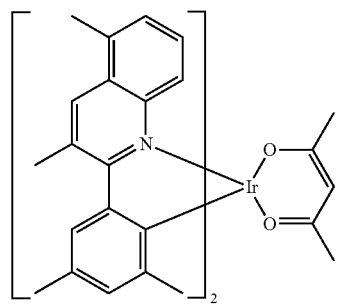
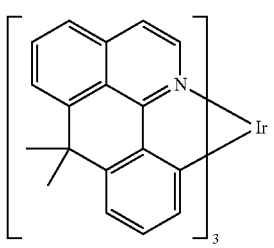
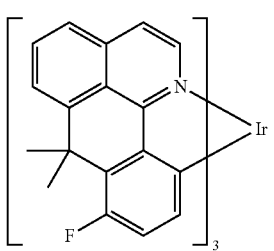
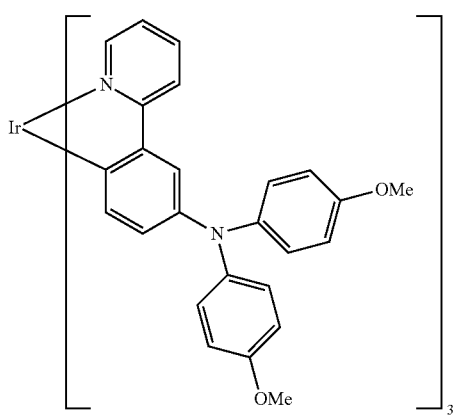
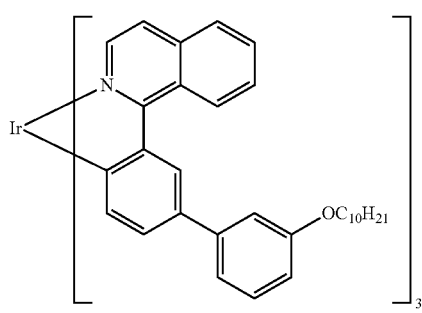
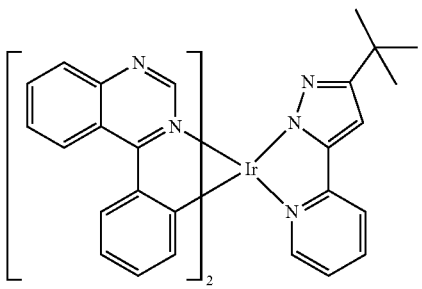
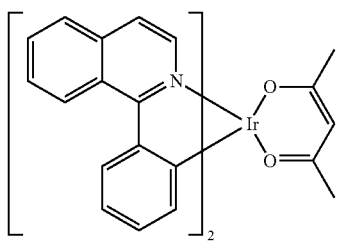
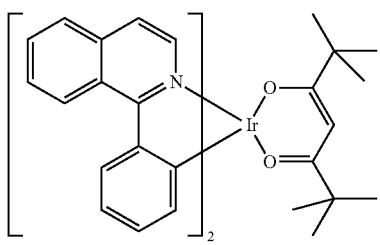
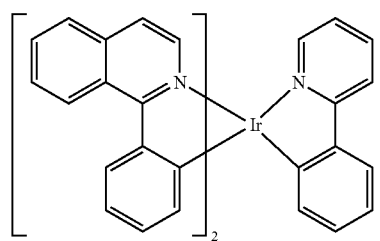
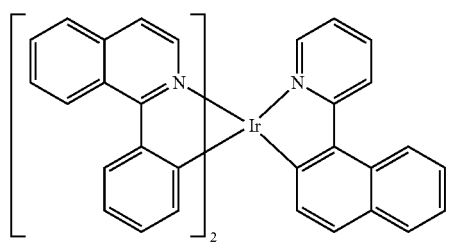
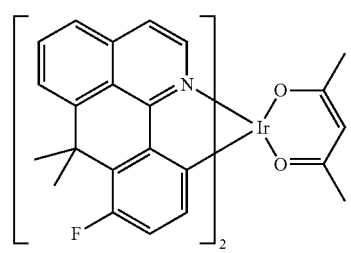

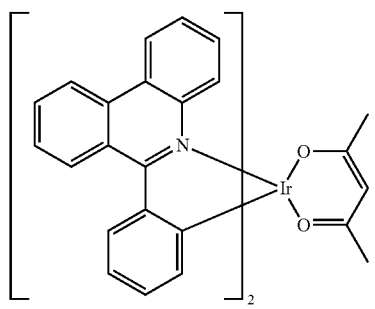
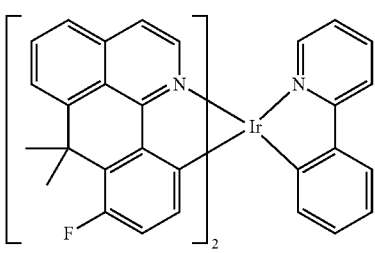
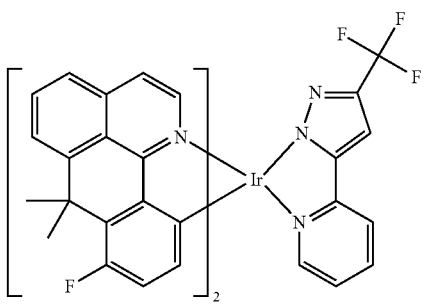
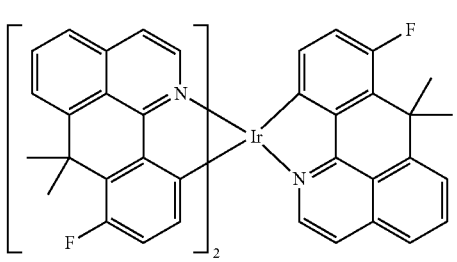
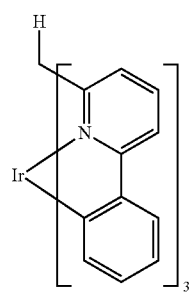
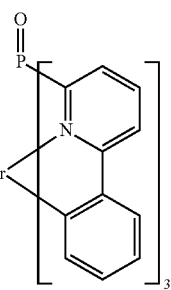
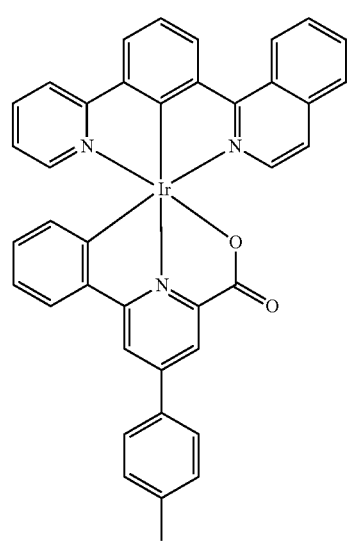
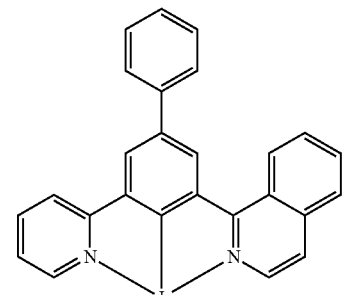
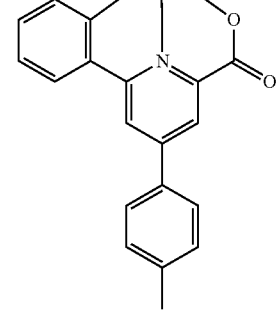

| 65 -continued | 66 -continued |
|---|---|
| 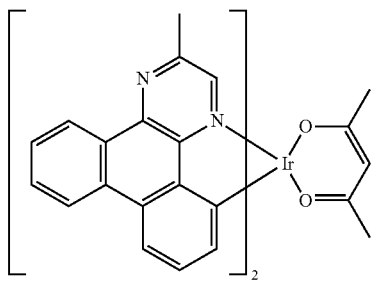 | 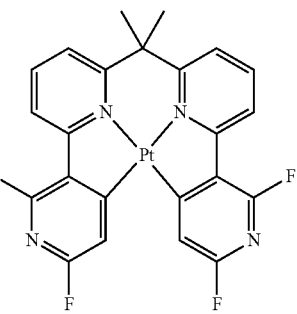 |
| 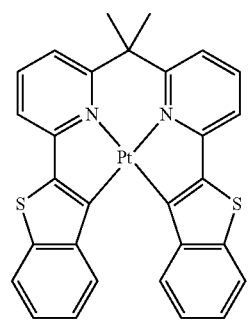 | 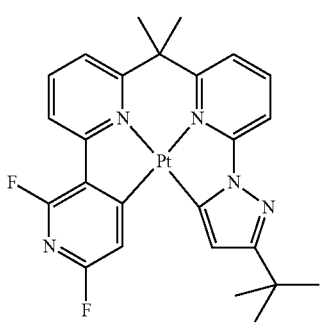 |
| 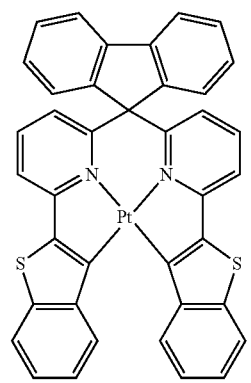 | 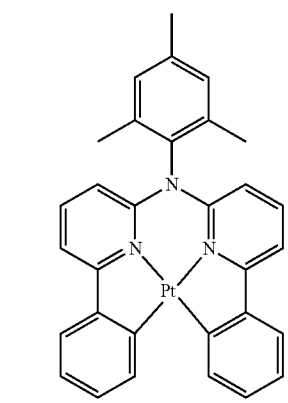 |
| 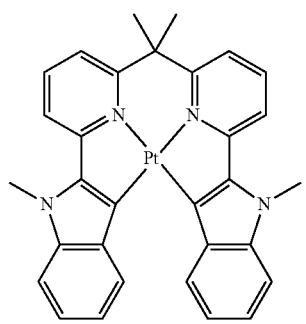 | 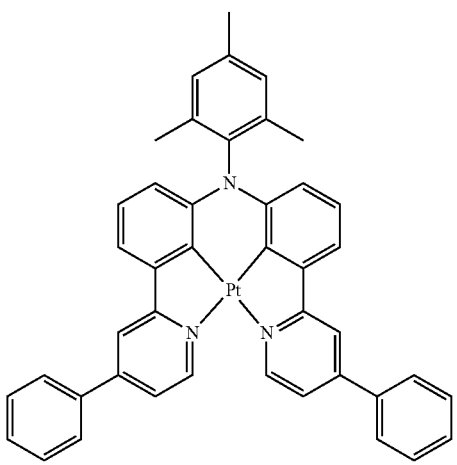 |
| 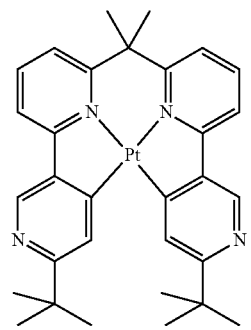 | |

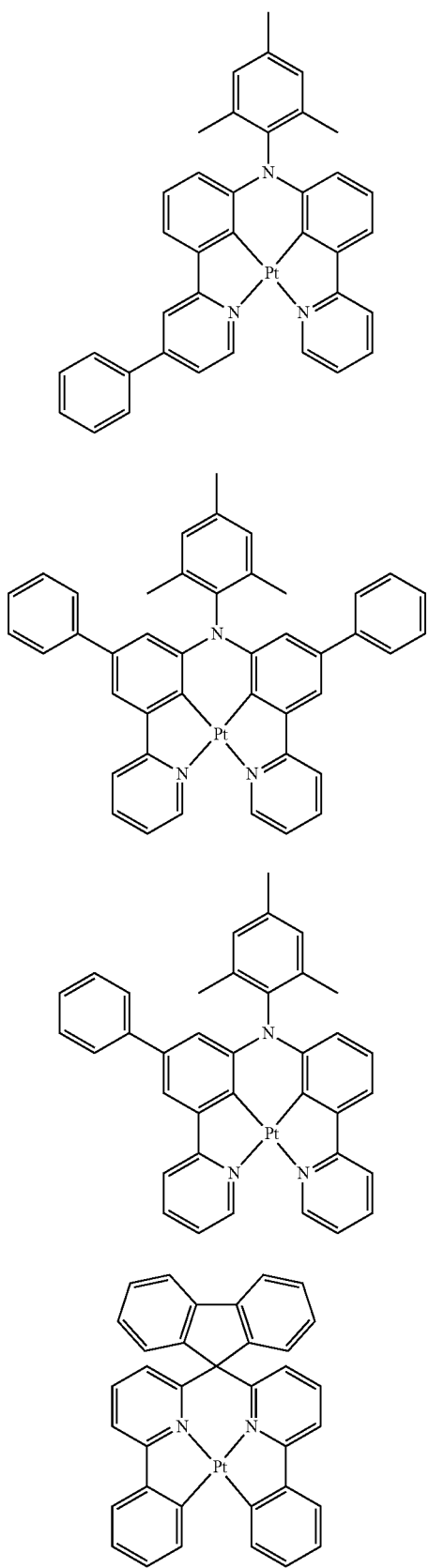
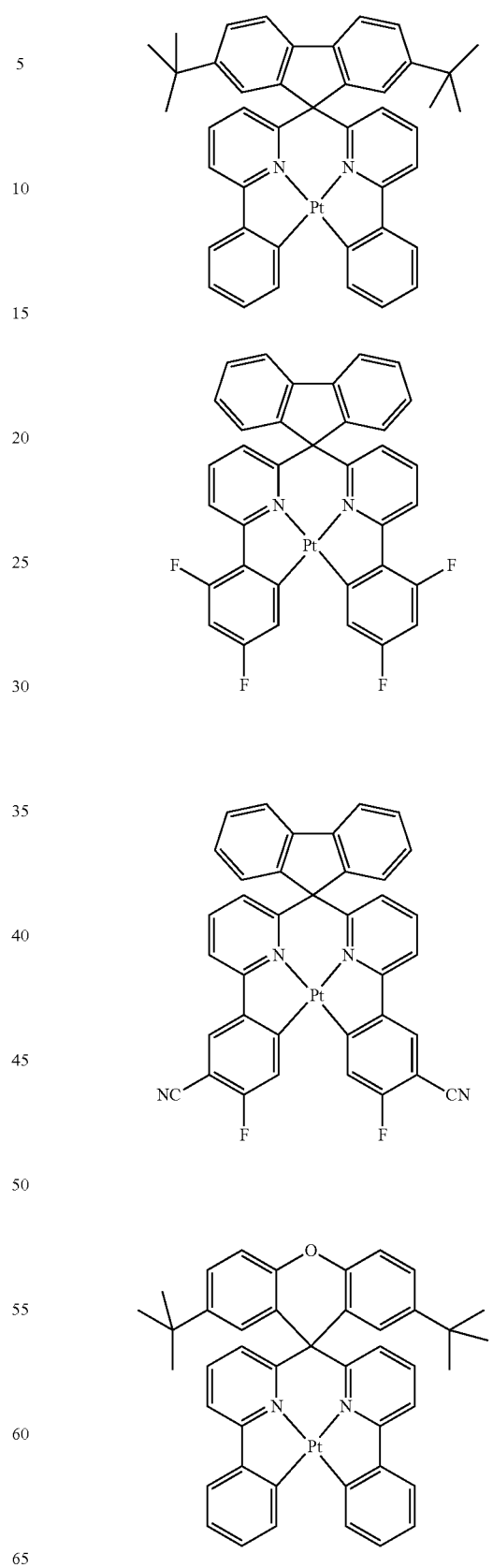

69
-continued
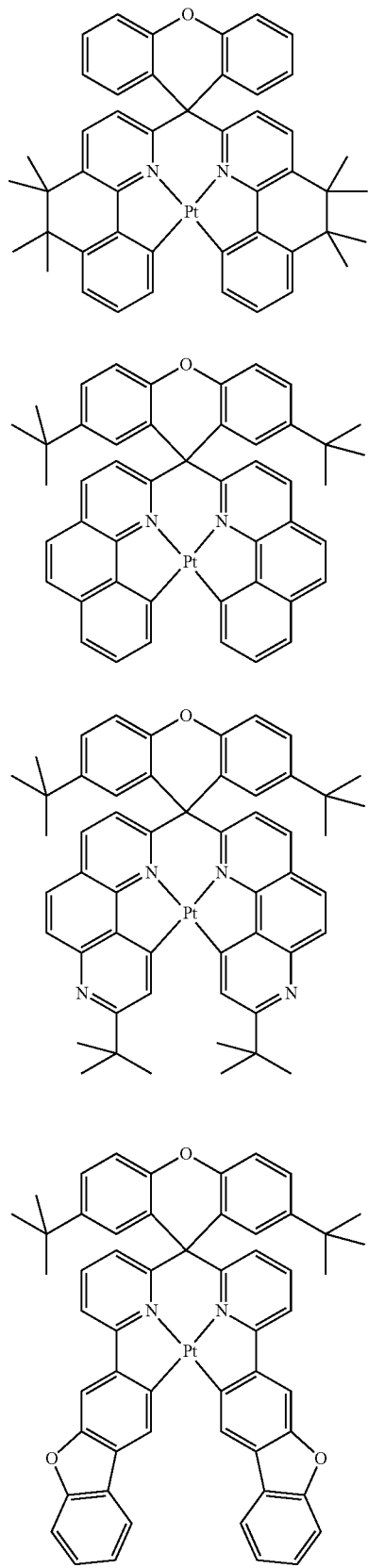
70
-continued
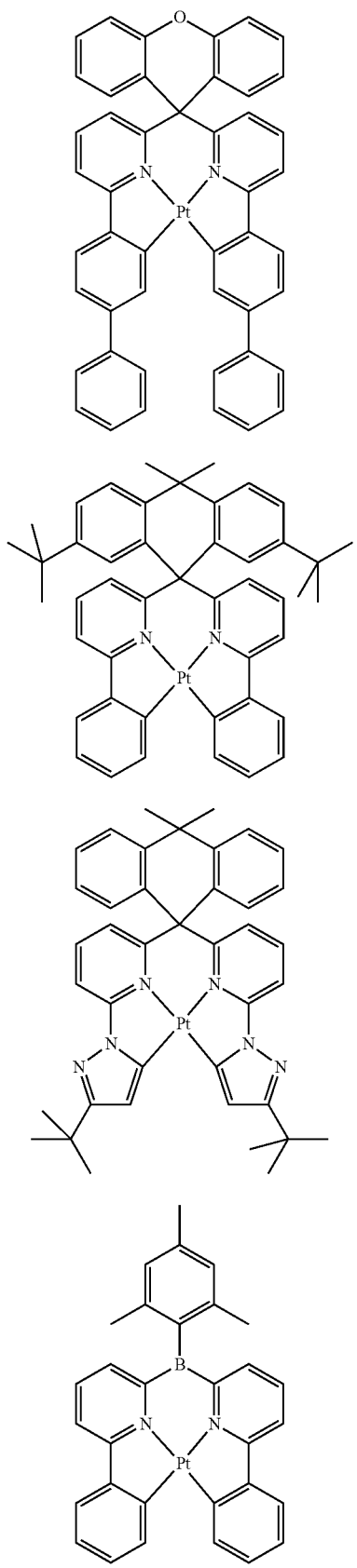

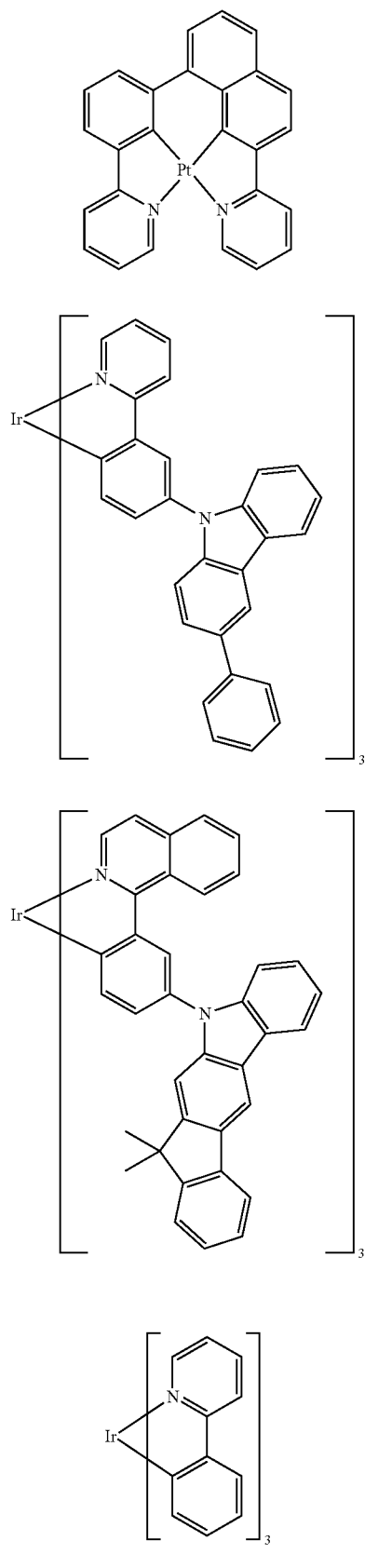
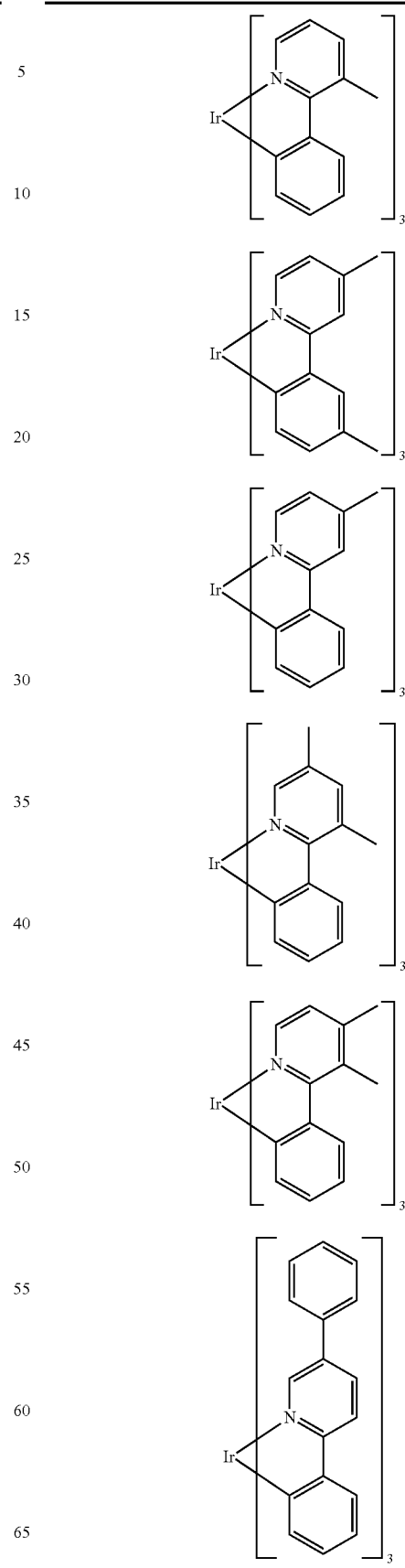

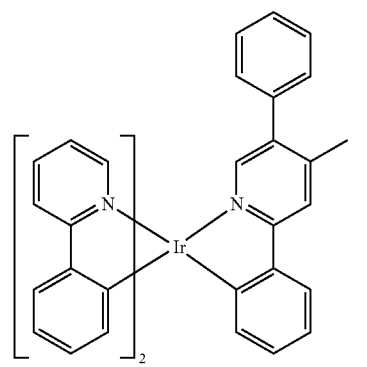
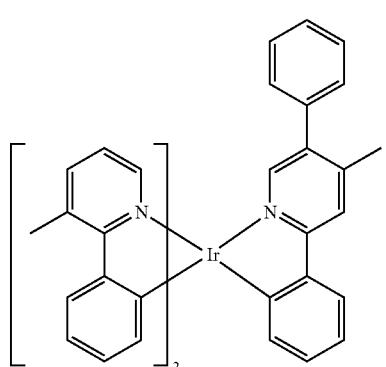
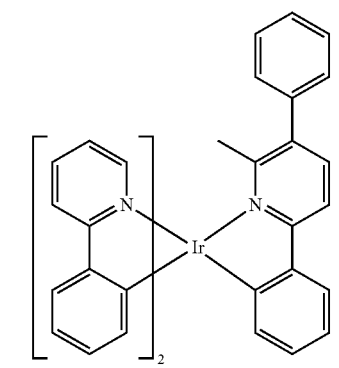
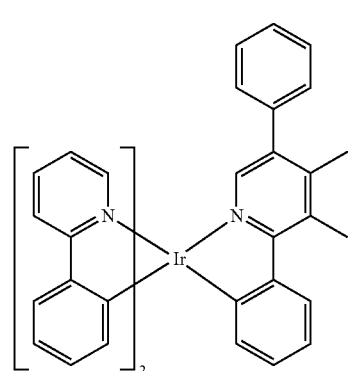
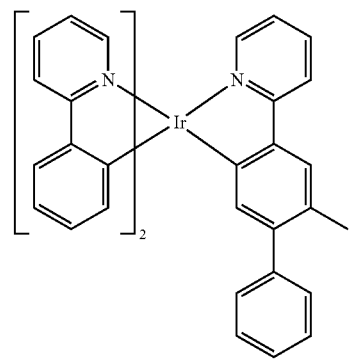
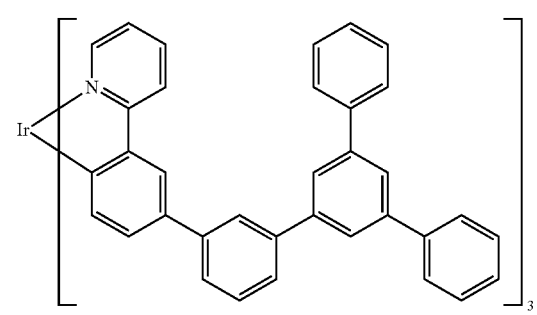
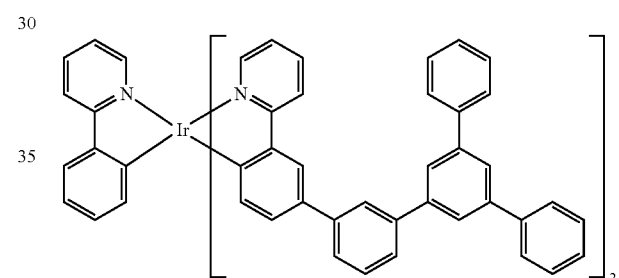
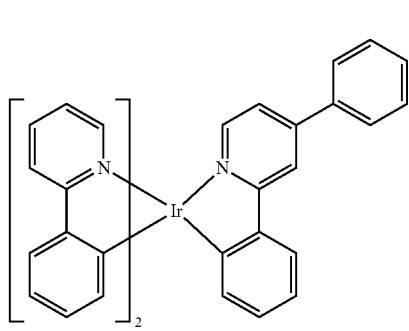
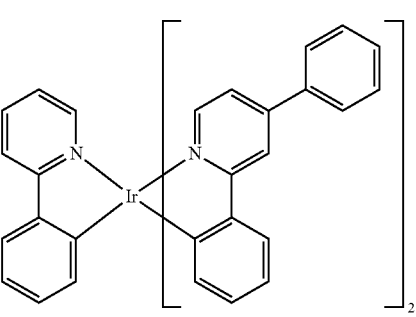

-continued
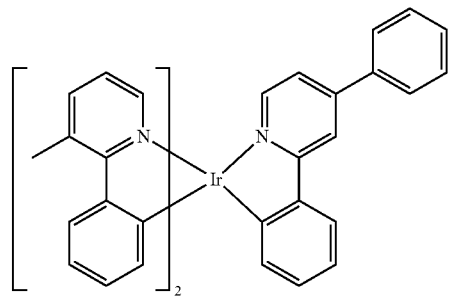
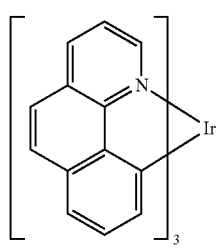
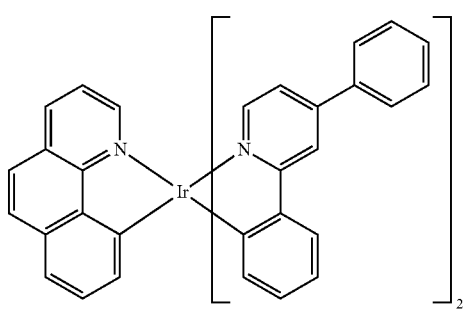
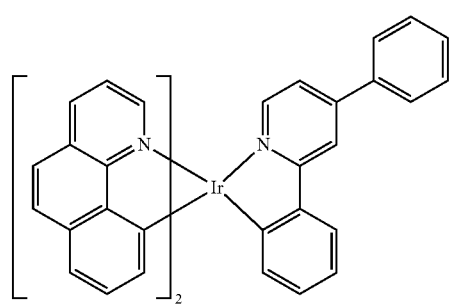
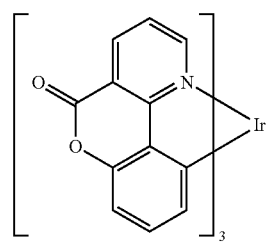
-continued
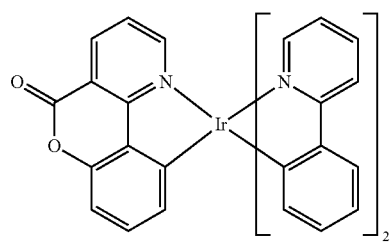
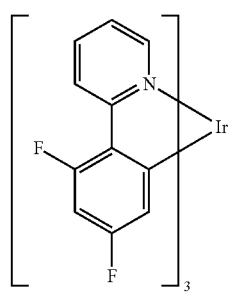
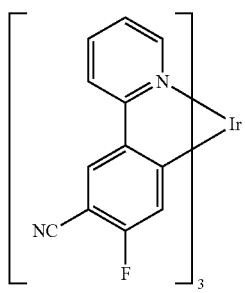
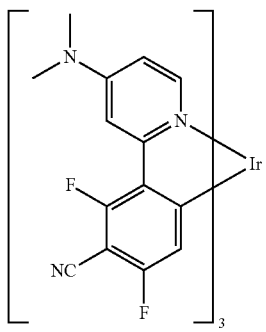

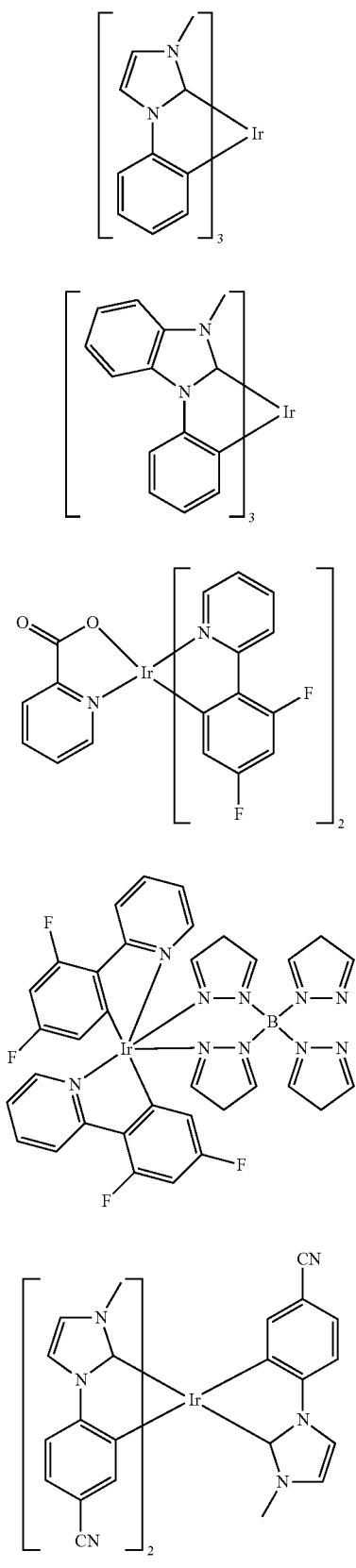
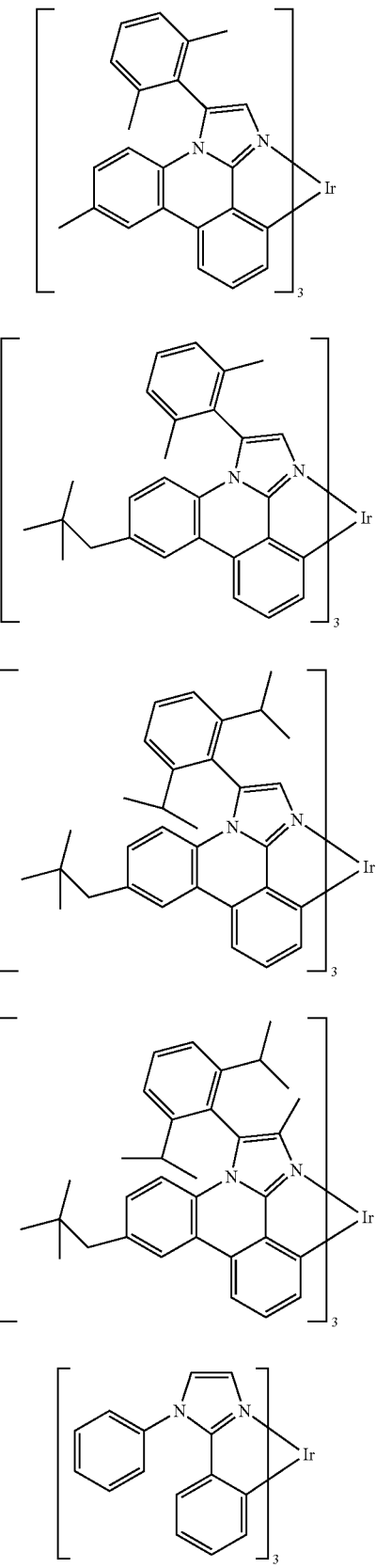

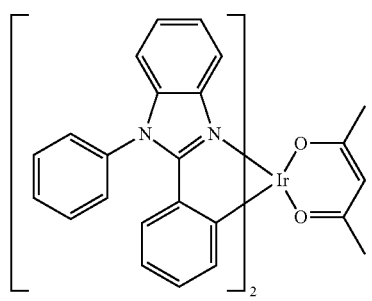

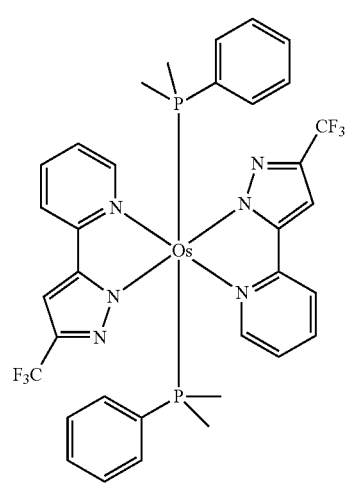

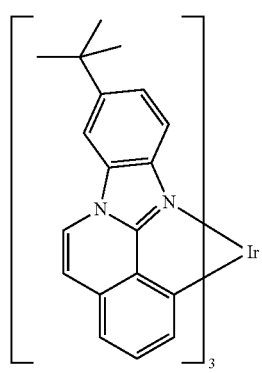

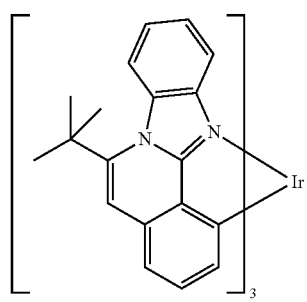

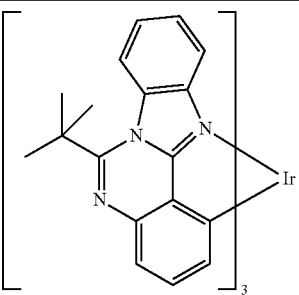

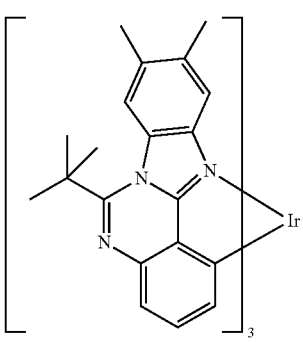

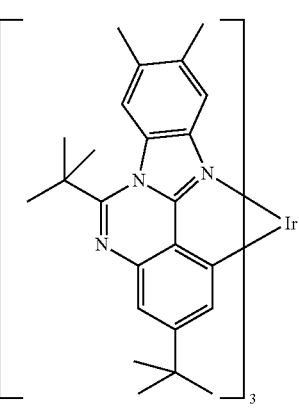

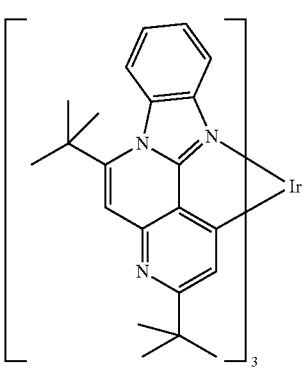

In a further embodiment of the invention, the inventive organic electroluminescent device does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In a further preferred embodiment of the invention, the compound of formula (1) or the above-recited preferred embodiments is used as electron transport material in an electron transport or electron injection layer. In this case, the emitting layer may be fluorescent or phosphorescent. When the compound is used as electron transport material, it may be preferable for it to be doped, for example with alkali metal complexes, for example LiQ (lithium hydroxyquinolinate).

In yet a further preferred embodiment of the invention, the compound of formula (1) or the above-recited preferred embodiments is used in a hole blocker layer. A hole blocker layer is understood to be a layer which directly adjoins an emitting layer on the cathode side.

It is additionally possible to use the compound of formula (1) or the above-recited preferred embodiments both in a hole blocker layer or electron transport layer and as matrix in an emitting layer.

In yet a further embodiment of the invention, the compound of formula (1) or the above-recited preferred embodiments is used in a hole transport layer or in an electron blocker layer or exciton blocker layer.

In the further layers of the inventive organic electroluminescent device, it is possible to use any materials as typically used according to the prior art. The person skilled in the art will therefore be able, without exercising inventive skill, to use any materials known for organic electroluminescent devices in combination with the inventive compounds of formula (1) or the above-recited preferred embodiments.

Additionally preferred is an organic electroluminescent device, characterized in that one or more layers are coated by a sublimation process. In this case, the materials are applied by vapor deposition in vacuum sublimation systems at an initial pressure of less than $10^{-5}$ mbar, preferably less than $10^{-6}$ mbar. It is also possible that the initial pressure is even lower, for example less than $10^{-7}$ mbar.

Preference is likewise given to an organic electroluminescent device, characterized in that one or more layers are coated by the OVPD (organic vapor phase deposition) method or with the aid of a carrier gas sublimation. In this case, the materials are applied at a pressure between $10^{-5}$ mbar and 1 bar. A special case of this method is the OVJP (organic vapor jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, offset printing, LITI (light-induced thermal imaging, thermal transfer printing), inkjet printing or nozzle printing. For this purpose, soluble compounds are needed, which are obtained, for example, through suitable substitution. These methods are especially also suitable for oligomers, dendrimers and polymers.

In addition, hybrid methods are possible, in which, for example, one or more layers are applied from solution and one or more further layers are applied by vapor deposition.

These methods are known in general terms to those skilled in the art and can be applied without exercising inventive skill to organic electroluminescent devices comprising the inventive compounds.

The inventive compounds and the inventive organic electroluminescent devices are notable for the following surprising advantages over the prior art:

1. The inventive compounds used as matrix material for fluorescent or phosphorescent emitters lead to high efficiencies and to long lifetimes. This is especially true when the compounds are used as matrix material for a red- or green-phosphorescing emitter.
2. The inventive compounds have high thermal stability.
3. The inventive compounds used in organic electroluminescent devices lead to high efficiencies and to steep current-voltage curves with low use voltages.
4. When used as electron transport material, the inventive compounds also lead to very good properties in relation to efficiency, lifetime and operating voltage of organic electroluminescent devices.

These abovementioned advantages are not accompanied by a deterioration in the further electronic properties.

The invention is illustrated in detail by the examples which follow, without any intention of restricting it thereby. The person skilled in the art will be able to use the information given to execute the invention over the entire scope disclosed and to prepare further inventive compounds without exercising inventive skill and to use them in electronic devices or to employ the process of the invention.

EXAMPLES

The syntheses which follow, unless stated otherwise, are conducted under a protective gas atmosphere. The reactants can be sourced from ALDRICH or ABCR (palladium(II) acetate, tri-o-tolylphosphine, inorganic materials, solvents). The synthesis of phenylacridone and 10-[1,1'-diphenyl]-4-ylacridinone and further derivatives can be effected according to the literature (Chemical Communications, 48(86), 10678-10680; 2012) and is known from the literature. The figures in square brackets are the CAS numbers of the compounds known from the literature.

Synthesis of Reactants a) Synthesis of tert-butyl (2-bromophenyl)phenylcarbamate

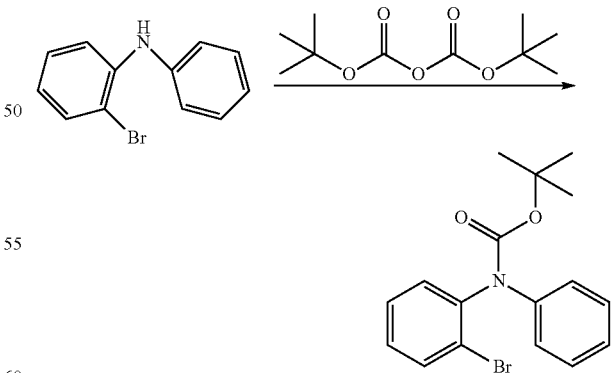

33 g (145 mmol) of di-tert-butyl dicarbonate are initially charged in 600 mL of toluene. To this solution are added 27 g (110 mmol) of (2-bromophenyl)phenylamine and 1.3 g (11 mmol) of 4-dimethylaminopyridine, and the mixture is boiled under reflux for 40 h. Subsequently, 200 mL of water are added to the reaction, the organic phase is separated off and the solvent is removed under reduced pressure. The residue is subjected to hot recrystallization from hexane. Yield: 36 g (103 mmol), 95%.

b) Synthesis of (2-bromothiophen-3-yl)phenylamine

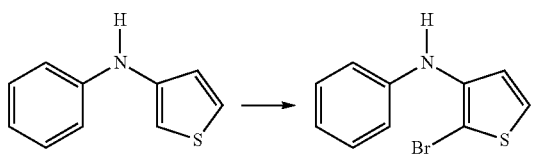 [SMILES: c1ccc(Nc2ccsc2)cc1 ; Brc1sccc1Nc1ccccc1]

10 g (57 mmol) of phenylthiophen-3-ylamine (CAS: 227805-72-3) are initially charged in 200 mL of CH$_2$Cl$_2$. Subsequently, a solution of 10.1 g (57 mmol) of NBS in 200 mL of acetonitrile is added dropwise in the dark at −15° C., the mixture is allowed to come to room temperature and stirring is continued at this temperature for 4 h. Subsequently, 150 mL of water are added to the mixture and extraction is effected with CH$_2$Cl$_2$. The organic phase is dried over MgSO$_4$ and the solvents are removed under reduced pressure. The product is subjected to extractive stirring with hot hexane and filtered off with suction. Yield: 11.6 g (45.6 mmol), 80% of theory, purity by $^1$H NMR about 97%.

Example 1: Spiro Synthesis

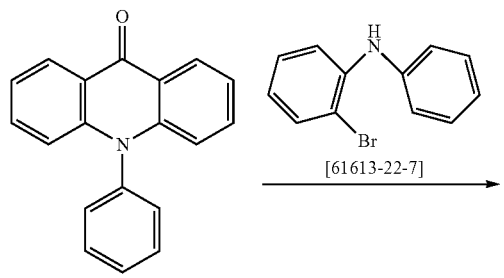

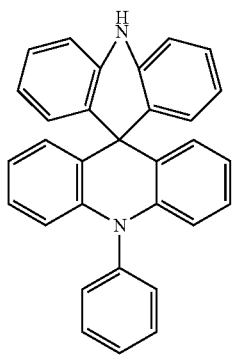

42.8 g (172 mmol) of 2-bromodiphenylamine are initially charged in 200 mL of absolute THF and cooled to −70° C., and 150 mL (345 mmol) of n-butyllithium are added. Subsequently, the mixture is allowed to come to −10° C. and stirred at this temperature for a further hour. Then 30 g (86 mmol) of 10-phenyl-1 OH-acridin-9-one dissolved in 500 mL of THF are added gradually and the mixture is stirred at room temperature for 24 h. 100 mL of ammonium chloride solution are added, the mixture is stirred briefly, the organic phase is separated off and the solvent is removed under reduced pressure. The residue is suspended in 800 mL of glacial acetic acid heated to 40° C., 75 mL of conc. hydrochloric acid are added to the suspension and the mixture is then stirred at room temperature for 8 h. After cooling, the precipitated solid is filtered off with suction and washed once with 100 mL of glacial acetic acid and three times with 100 mL each time of ethanol, and finally recrystallized from hexane. Yield: 29 g (68 mmol), 63%; purity about 98% by $^1$H NMR.

In an analogous manner, it is possible to obtain the following compounds:

| Ex. | Reactant 1 | Reactant 2 |
|---|---|---|
| 1a | (structure: 10-phenyl-acridin-9(10H)-one) | (structure with [861572-31-8]) |

| | | |
|---|---|---|
| 1b | 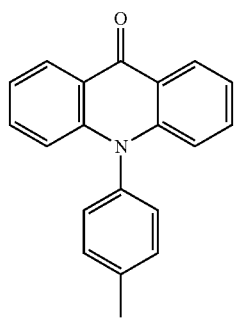 [102023-92-7] | 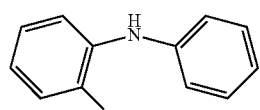 [61613-22-7] |
| 1c | 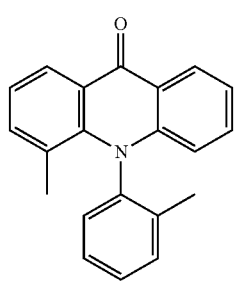 [SMILES: O=c1c2ccccc2n(-c2ccccc2)c2ccccc12] [1195562-29-8] | 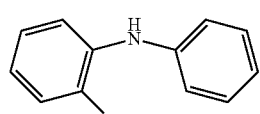 [61613-22-7] |
| 1d | 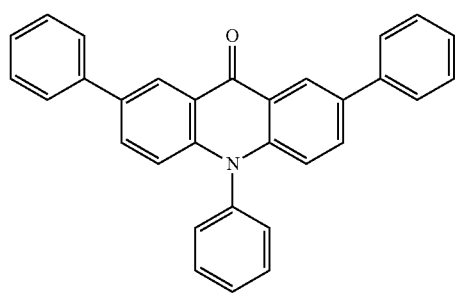 [1416006-28-4] | 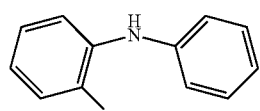 [61613-22-7] |
| 1e | 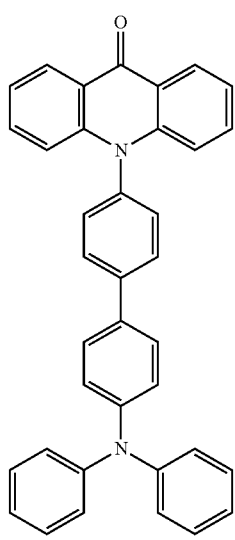 [1188546-10-2] | 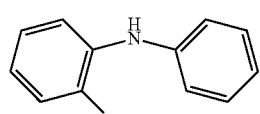 [61613-22-7] |

1f 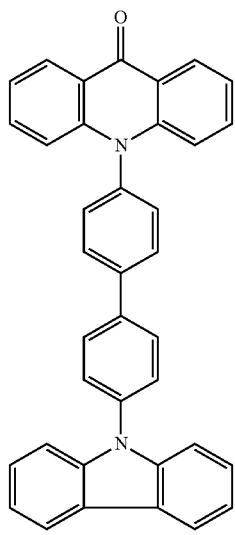
[1188546-11-3]
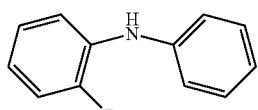
[61613-22-7]
1g 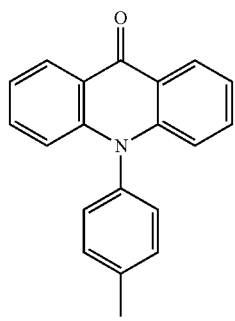
[102023-92-7]
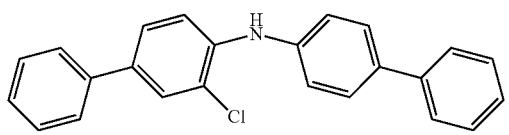
[861572-31-8]
1h 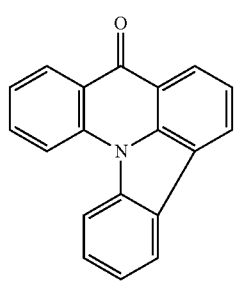
[32081-26-8]
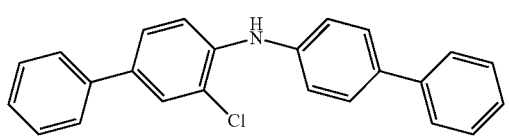
[861572-31-8]
1j 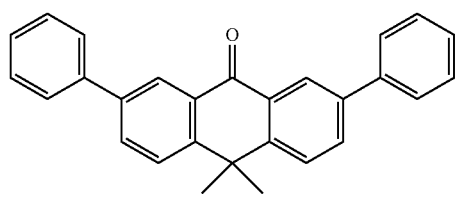
[1346009-95-7]
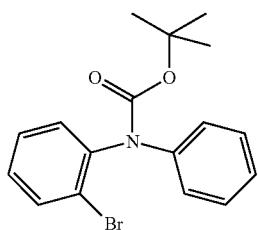 [SMILES: CC(C)(C)OC(=O)N(c1ccccc1)c1ccccc1Br]

-continued
1i 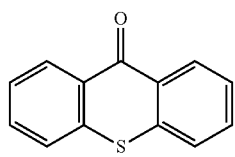
[1380298-27-0]
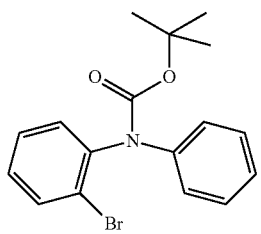 [SMILES: CC(C)(C)OC(=O)N(c1ccccc1)c1ccccc1Br]
1k 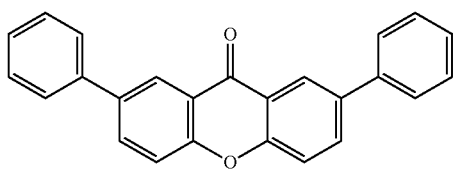
[854661-66-8]
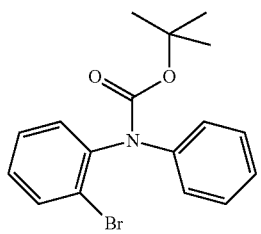 [SMILES: CC(C)(C)OC(=O)N(c1ccccc1)c1ccccc1Br]
1l 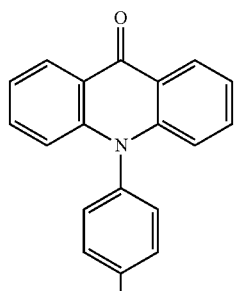
[102023-92-7]
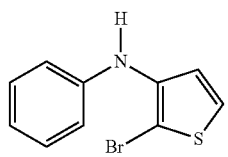 [SMILES: Brc1sccc1Nc1ccccc1]
1m 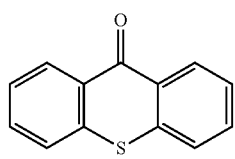
[1380298-27-0]
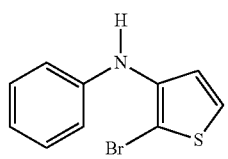 [SMILES: Brc1sccc1Nc1ccccc1]
1n 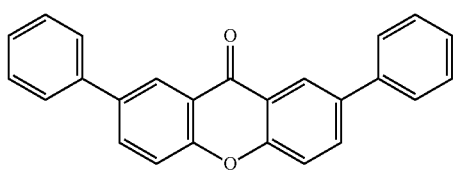
[854661-66-8]
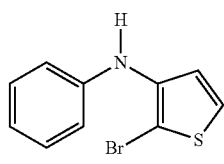 [SMILES: Brc1sccc1Nc1ccccc1]
1o 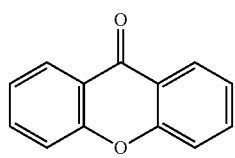
[90-47-1]
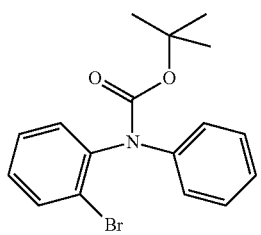 [SMILES: CC(C)(C)OC(=O)N(c1ccccc1)c1ccccc1Br]

-continued
1p 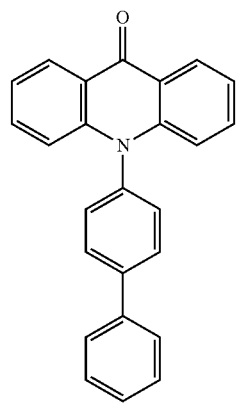 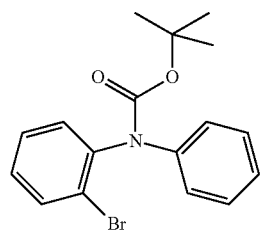 [SMILES: CC(C)(C)OC(=O)N(c1ccccc1)c1ccccc1Br]
[1408293-66-2]
1q 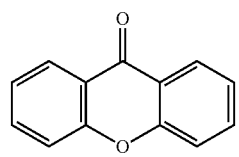 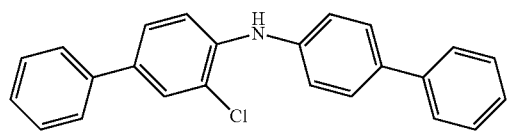
[90-47-1]　　　　　　　　　　　　[861572-31-8]
| Ex. | Product | Yield |
|---|---|---|
| 1a | 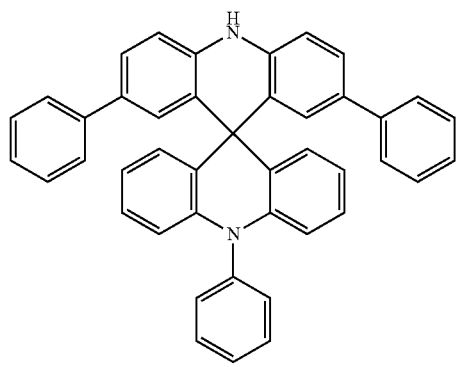 [SMILES: c1ccc(-c2ccc3c(c2)C2(c4cc(-c5ccccc5)ccc4N3)c3ccccc3N(c3ccccc3)c3ccccc32)cc1] | 65% |
| 1b | 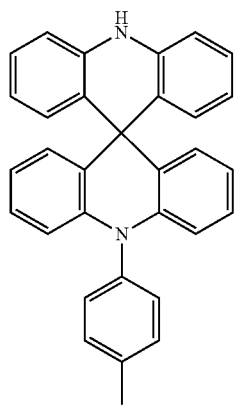 [SMILES: Cc1ccc(N2c3ccccc3C3(c4ccccc4Nc4ccccc43)c3ccccc32)cc1] | 69% |

| | | |
|---|---|---|
| 1c | 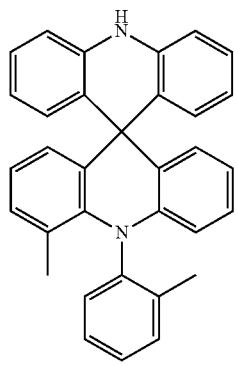 [SMILES: Cc1ccccc1N1c2ccccc2C2(c3ccccc3Nc3ccccc32)c2cccc(C)c21] | 71% |
| 1d | 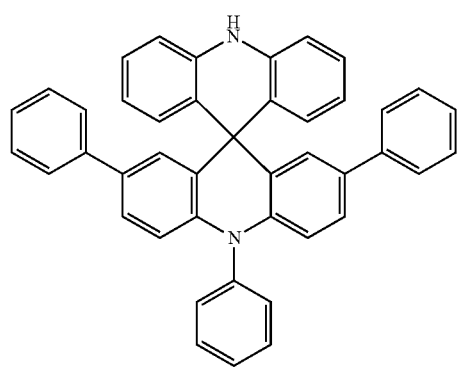 [SMILES: c1ccc(-c2ccc3c(c2)C2(c4ccccc4Nc4ccccc42)c2cc(-c4ccccc4)ccc2N3c2ccccc2)cc1] | 67% |
| 1e | 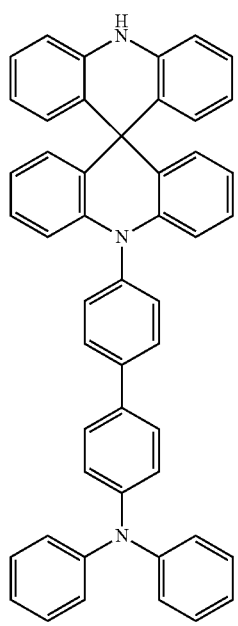 [SMILES: c1ccc(N(c2ccccc2)c2ccc(-c3ccc(N4c5ccccc5C5(c6ccccc6Nc6ccccc65)c5ccccc54)cc3)cc2)cc1] | 59% |

-continued
| | | |
|---|---|---|
| 1f | 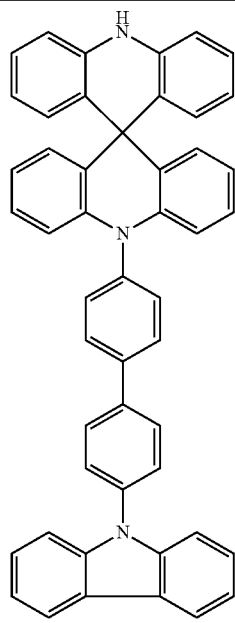 | 62% |
| 1g | 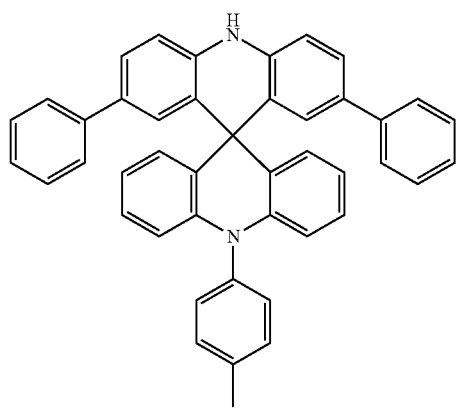 [SMILES: Cc1ccc(N2c3ccccc3C3(c4cc(-c5ccccc5)ccc4Nc4ccc(-c5ccccc5)cc43)c3ccccc32)cc1] | 65% |
| 1h | 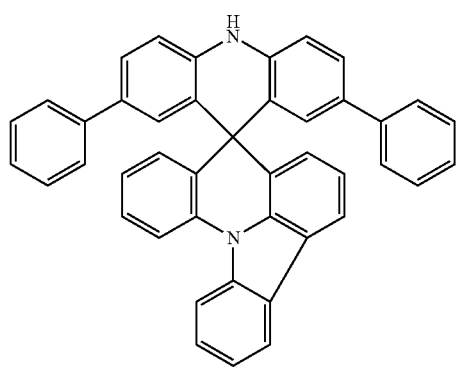 [SMILES: c1ccc(-c2ccc3c(c2)C2(c4cc(-c5ccccc5)ccc4N3)c3ccccc3-n3c4ccccc4c4cccc2c43)cc1] | 69% |
| 1j | 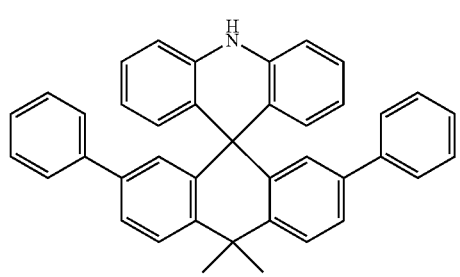 [SMILES: CC1(C)c2ccc(-c3ccccc3)cc2C2(c3ccccc3Nc3ccccc32)c2cc(-c3ccccc3)ccc21] | 73% |

-continued
1i 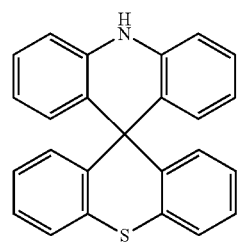 [SMILES: c1ccc2c(c1)Nc1ccccc1C21c2ccccc2Sc2ccccc21] 79%
1k 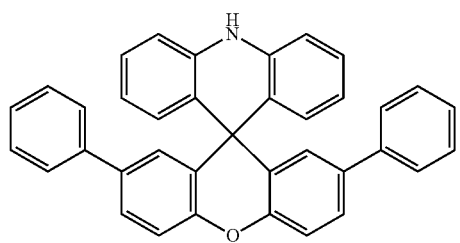 [SMILES: c1ccc(-c2ccc3c(c2)C2(c4ccccc4Nc4ccccc42)c2cc(-c4ccccc4)ccc2O3)cc1] 70%
1l 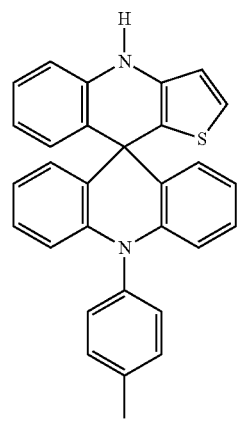 [SMILES: Cc1ccc(N2c3ccccc3C3(c4ccccc4Nc4ccsc43)c3ccccc32)cc1] 68%
1m 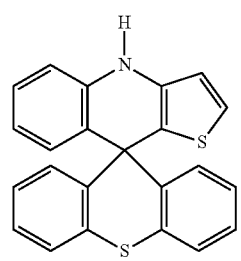 [SMILES: c1ccc2c(c1)Nc1ccsc1C21c2ccccc2Sc2ccccc21] 72%
1n 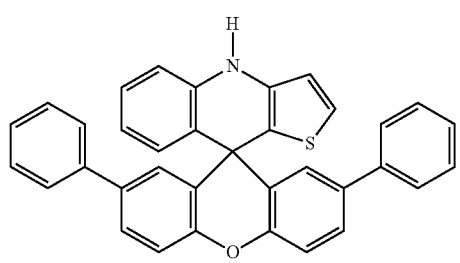 [SMILES: c1ccc(-c2ccc3c(c2)C2(c4ccccc4Nc4ccsc42)c2cc(-c4ccccc4)ccc2O3)cc1] 68%

-continued
| | | |
|---|---|---|
| 1o | 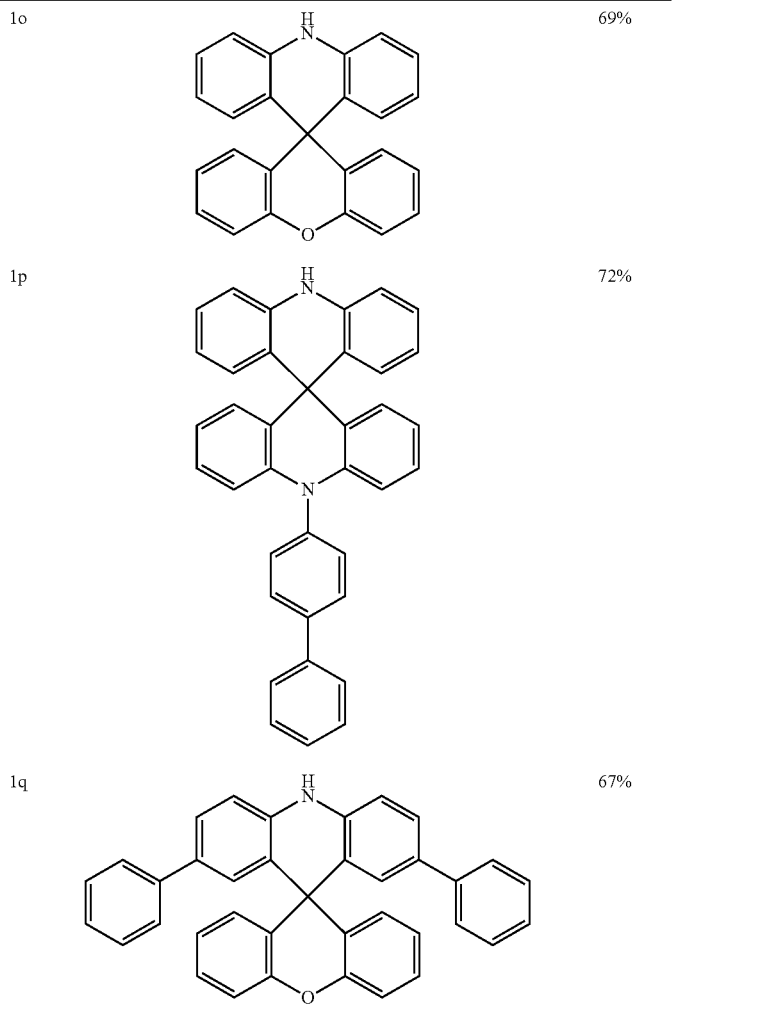 | 69% |
| 1p | | 72% |
| 1q | | 67% |
Example 2: Nucleophilic Substitution (Method 1)
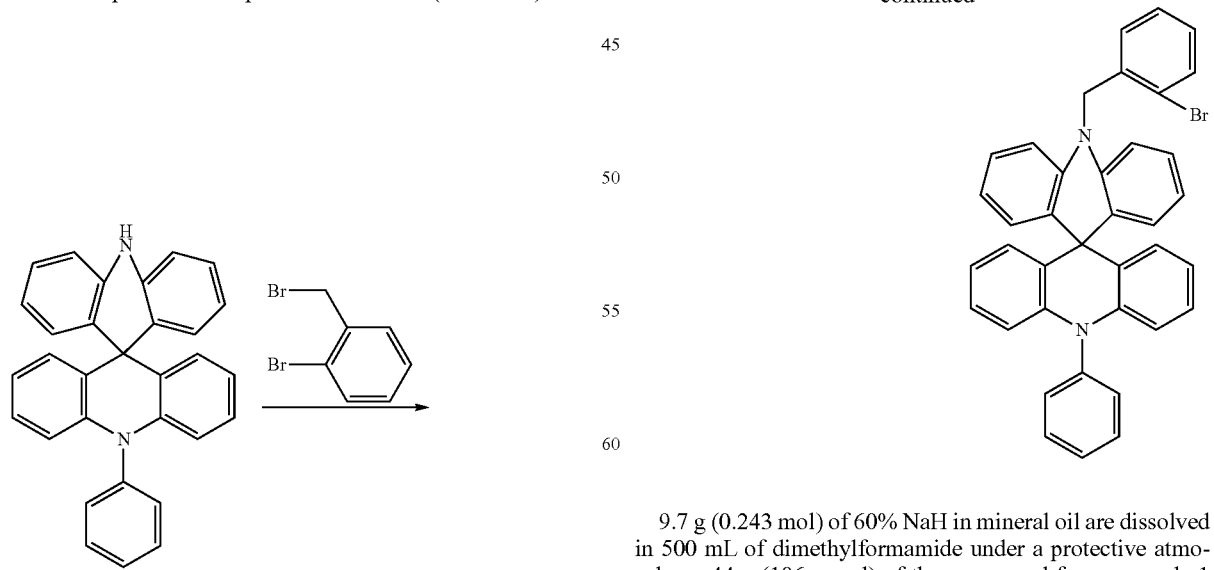
9.7 g (0.243 mol) of 60% NaH in mineral oil are dissolved in 500 mL of dimethylformamide under a protective atmosphere. 44 g (106 mmol) of the compound from example 1 are dissolved in 500 mL of DMF and added dropwise to the reaction mixture. After 1 h at room temperature, a solution of 60.6 g (242 mmol) of 2-bromobenzyl bromide in 500 mL of DMF is added dropwise. The reaction mixture is then stirred at room temperature for 1 h. After this time, the reaction mixture is poured onto ice and extracted three times with dichloromethane. The combined organic phases are dried over Na$_2$SO$_4$ and concentrated. The residue is subjected to hot extraction with toluene and recrystallized from toluene/n-heptane. Yield: 55 g (93 mmol), 90%.

In an analogous manner, it is possible to obtain the following compounds:

| Ex. | Reactant 1 | Reactant 2 | Product | Yield |
|---|---|---|---|---|
| 2a | 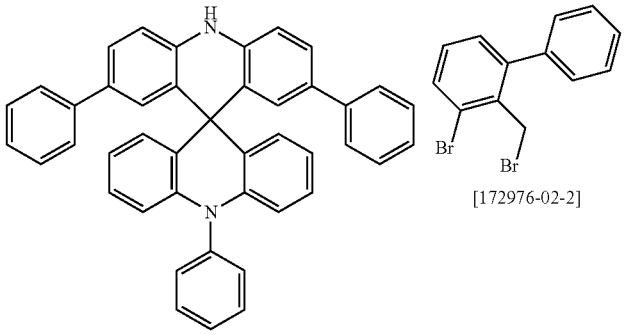 | 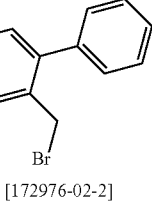[172976-02-2] | 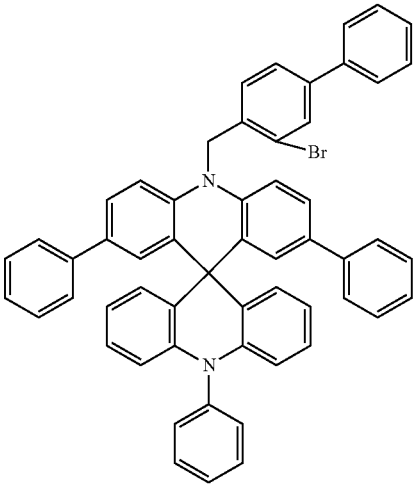 [SMILES: Brc1cc(-c2ccccc2)ccc1CN1c2ccc(-c3ccccc3)cc2C2(c3cc(-c4ccccc4)ccc31)c1ccccc1N(c1ccccc1)c1ccccc12] | 79% |
| 2b | 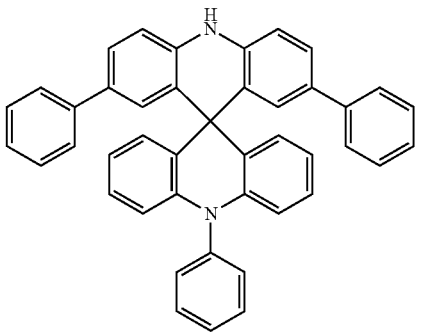 [SMILES: c1ccc(-c2ccc3c(c2)C2(c4cc(-c5ccccc5)ccc4N3)c3ccccc3N(c3ccccc3)c3ccccc32)cc1] | 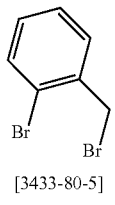[3433-80-5] | 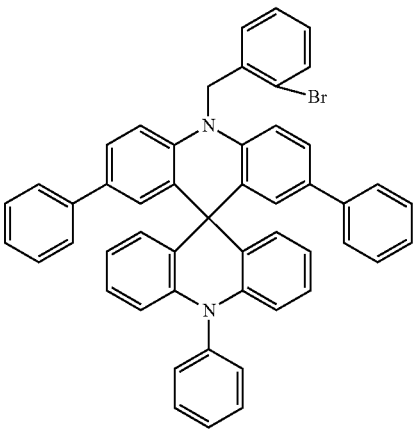 [SMILES: Brc1ccccc1CN1c2ccc(-c3ccccc3)cc2C2(c3cc(-c4ccccc4)ccc31)c1ccccc1N(c1ccccc1)c1ccccc12] | 87% |
| 2c | 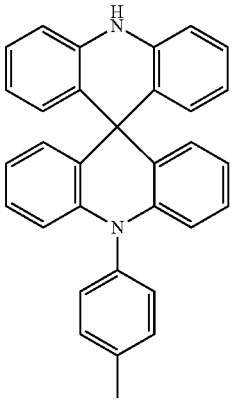 [SMILES: Cc1ccc(N2c3ccccc3C3(c4ccccc4Nc4ccccc43)c3ccccc32)cc1] | 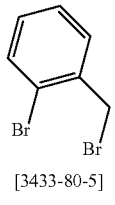[3433-80-5] | 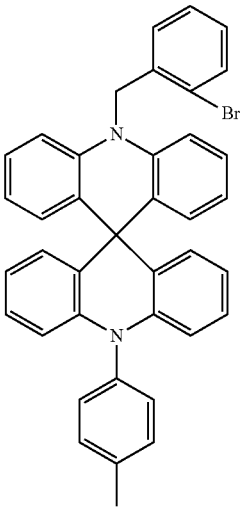 [SMILES: Cc1ccc(N2c3ccccc3C3(c4ccccc4N(Cc4ccccc4Br)c4ccccc43)c3ccccc32)cc1] | 92% |

-continued

| Ex. | Reactant 1 | Reactant 2 | Product | Yield |
|---|---|---|---|---|
| 2d | | [1214372-35-6] | | 90% |
| 2e | | [172976-02-2] | | 90% |
| 2f | | [202805-71-8] | | 82% |

-continued

| Ex. | Reactant 1 | Reactant 2 | Product | Yield |
|---|---|---|---|---|
| 2g | | [3433-80-5] | | 88% |
| 2h | | [3433-80-5] | | 79% |
| 2i | | [3433-80-5] | | 78% |

-continued

| Ex. | Reactant 1 | Reactant 2 | Product | Yield |
|---|---|---|---|---|
| 2j | | [3433-80-5] | | 89% |
| 2k | | [3433-80-5] | | 83% |
| 2l | | [3433-80-5] | | 86% |
| 2m | | [3433-80-5] | | 88% |

-continued

| Ex. | Reactant 1 | Reactant 2 | Product | Yield |
|---|---|---|---|---|
| 2n | | [3433-80-5] | | 87% |
| 2o | | [172976-02-2] | | 84% |
| 2p | | [3433-80-5] | | 80% |

| Ex. | Reactant 1 | Reactant 2 | Product | Yield |
|---|---|---|---|---|
| 2q | [structure] | [structure] [3433-80-5] | [structure] | 83% |
| 2r | [structure] | [structure] [3433-80-5] | [structure] | 82% |

Example 3: Cyclization 93 g (158 mmol) of the compound from example 2 are dissolved in 500 mL of dimethylformamide under a protective atmosphere. Added to this solution are 17.3 g (0.075 mol) of benzyltrimethylammonium bromide and 31.28 g (0.226 mol) of potassium carbonate. Subsequently, under protective gas, 5.08 g (0.022 mol) of Pd(OAc)$_2$ are added and the mixture is stirred at 120° C. for 9 h. After this time, the reaction mixture is cooled to room temperature and extracted with dichloromethane. The combined organic phases are dried over Na$_2$SO$_4$ and concentrated. The residue is recrystallized from n-heptane. Yield: 64 g (126 mmol), 80%.

In an analogous manner, it is possible to obtain the following compounds:

| Ex. | Reactant | Product | Yield |
|---|---|---|---|
| 3a | 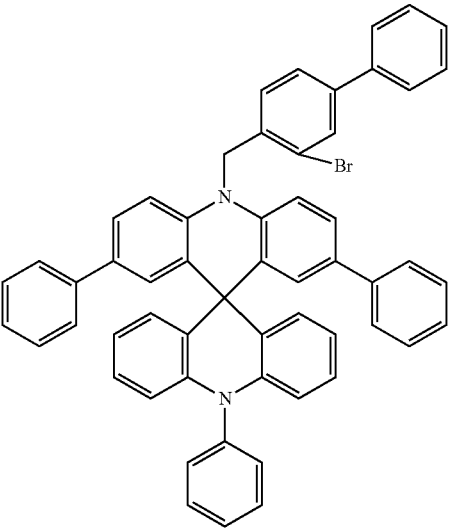 [SMILES: Brc1cc(-c2ccccc2)ccc1CN1c2ccc(-c3ccccc3)cc2C2(c3cc(-c4ccccc4)ccc31)c1ccccc1N(c1ccccc1)c1ccccc12] | 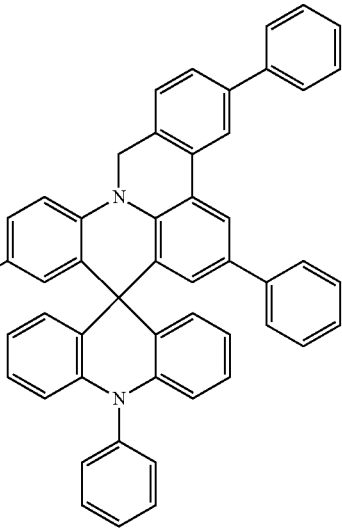 | 80% |
| 3b | 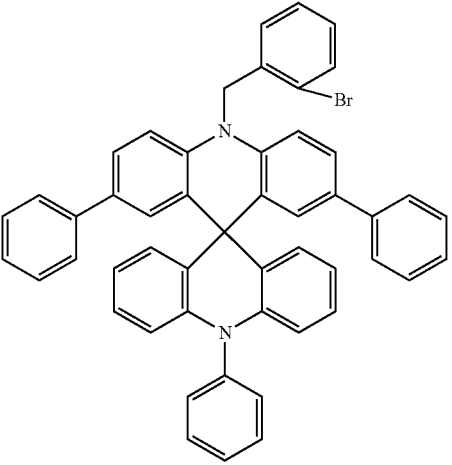 [SMILES: Brc1ccccc1CN1c2ccc(-c3ccccc3)cc2C2(c3cc(-c4ccccc4)ccc31)c1ccccc1N(c1ccccc1)c1ccccc12] | 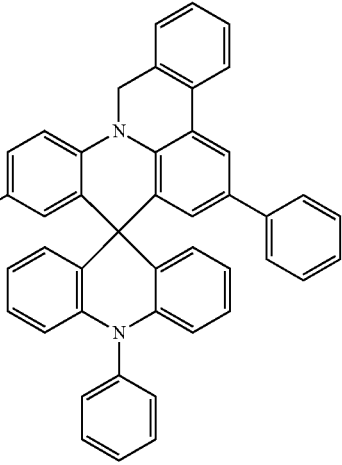 | 84% |
| 3c | 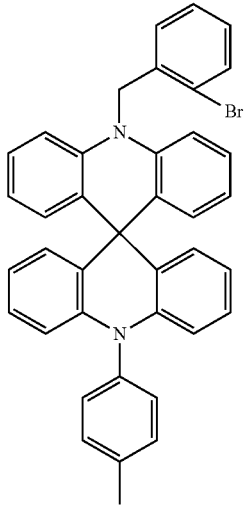 [SMILES: Cc1ccc(N2c3ccccc3C3(c4ccccc4N(Cc4ccccc4Br)c4ccccc43)c3ccccc32)cc1] | 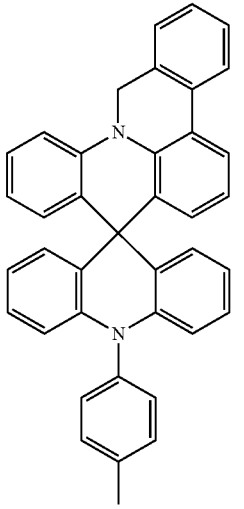 [SMILES: Cc1ccc(N2c3ccccc3C3(c4ccccc4N4Cc5ccccc5-c5cccc3c54)c3ccccc32)cc1] | 85% |

| Ex. | Reactant | Product | Yield |
|---|---|---|---|
| 3d | 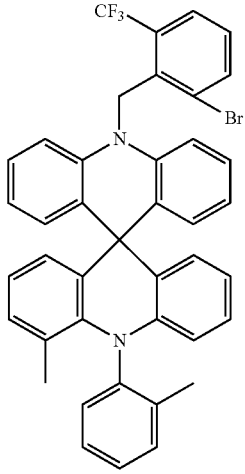 [SMILES: Cc1ccccc1N1c2ccccc2C2(c3ccccc3N(Cc3c(Br)cccc3C(F)(F)F)c3ccccc32)c2cccc(C)c21] | 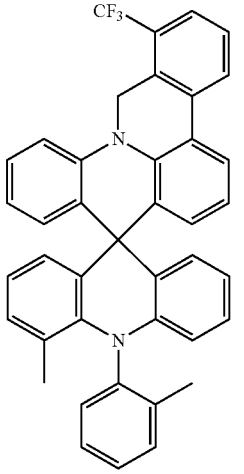 [SMILES: Cc1ccccc1N1c2ccccc2C2(c3ccccc3N3Cc4c(cccc4C(F)(F)F)-c4cccc2c43)c2cccc(C)c21] | 81% |
| 3e | 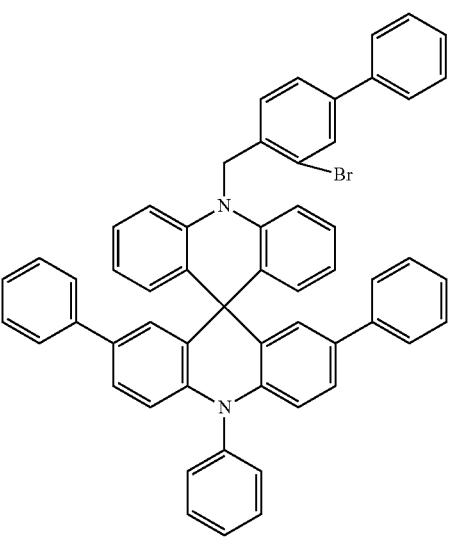 [SMILES: Brc1cc(-c2ccccc2)ccc1CN1c2ccccc2C2(c3ccccc31)c1cc(-c3ccccc3)ccc1N(c1ccccc1)c1ccc(-c3ccccc3)cc12] | 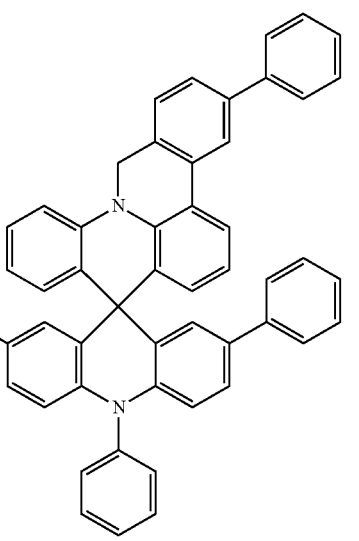 | 88% |

-continued
| Ex. | Reactant | Product | Yield |
|---|---|---|---|
| 3f | 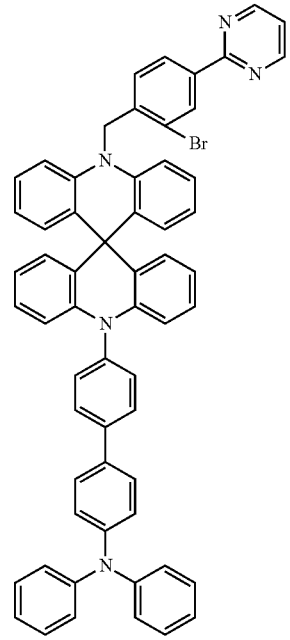 [SMILES: Brc1cc(-c2ncccn2)ccc1CN1c2ccccc2C2(c3ccccc31)c1ccccc1N(c1ccc(-c3ccc(N(c4ccccc4)c4ccccc4)cc3)cc1)c1ccccc12] | 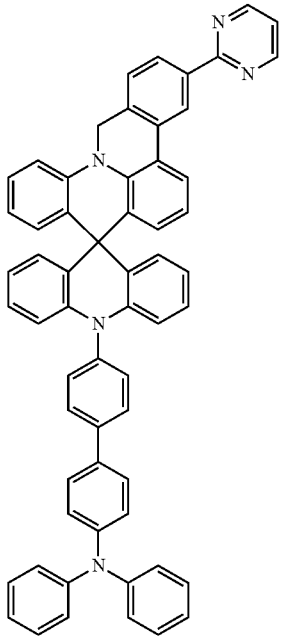 [SMILES: c1ccc(N(c2ccccc2)c2ccc(-c3ccc(N4c5ccccc5C5(c6ccccc6N6Cc7ccc(-c8ncccn8)cc7-c7cccc5c76)c5ccccc54)cc3)cc2)cc1] | 79% |
| 3g | 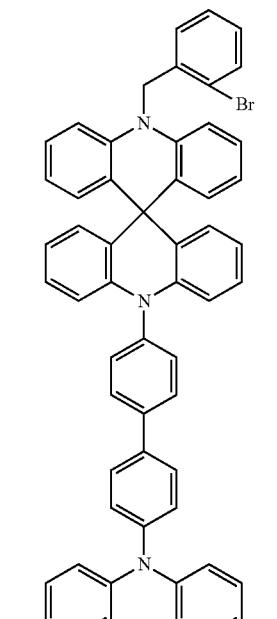 | 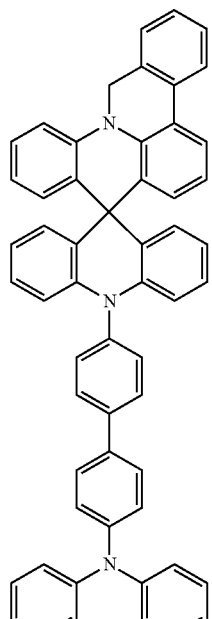 | 78% |

-continued

| Ex. | Reactant | Product | Yield |
|---|---|---|---|
| 3h | | | 76% |
| 3i | | | 81% |
| 3j | | | 69% |

-continued

| Ex. | Reactant | Product | Yield |
|---|---|---|---|
| 3k | | | 60% |
| 3l | | | 55% |
| 3m | | | 55% |

-continued

| Ex. | Reactant | Product | Yield |
|---|---|---|---|
| 3n | | | 54% |
| 3o | | | 56% |
| 3p | | | 53% |
| 3q | | | 55% |

| Ex. | Reactant | Product | Yield |
|---|---|---|---|
| 3r | | | 59% |
| 3s | | | 61% |

Example 4: Oxidation

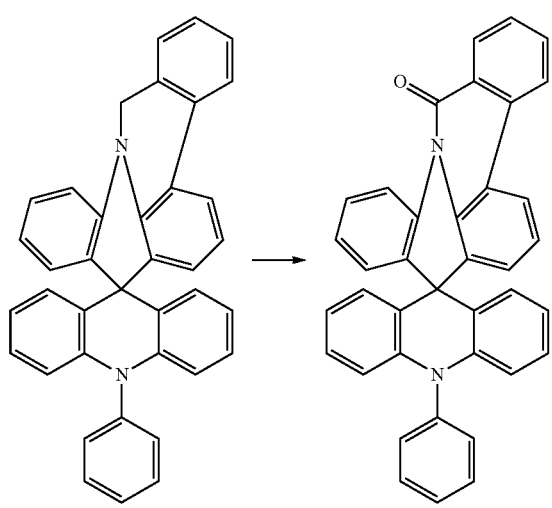 [SMILES: c1ccc(N2c3ccccc3C3(c4ccccc4N4Cc5ccccc5-c5cccc3c54)c3ccccc32)cc1 ; O=c1c2ccccc2c2cccc3c2n1-c1ccccc1C31c2ccccc2N(c2ccccc2)c2ccccc21]

19.9 g (39 mmol) of the compound from example 3 are dissolved in 300 mL of dichloromethane. Added to this solution in portions are 17.3 g (0.075 mol) of benzyltrimethylammonium bromide and 62.13 g (0.393 mol) of potassium permanganate, and the mixture is stirred at room temperature for two days. After this time, the rest of the potassium permanganate is filtered off, and the solution is concentrated and purified by chromatography (eluent: heptane/dichloromethane, 5:1). The residue is recrystallized from toluene and from dichloromethane and finally sublimed under high vacuum. Yield: 17 g (132 mmol), 86%, purity: 99.9%.

In an analogous manner, it is possible to obtain the following compounds:

| Ex. | Reactant | Product | Yield |
|---|---|---|---|
| 4a | | | 82% |
| 4b | | | 85% |
| 4c | | | 86% |

| Ex. | Reactant | Product | Yield |
|---|---|---|---|
| 4d | | | 81% |
| 4e | | | 79% |

-continued

| Ex. | Reactant | Product | Yield |
|---|---|---|---|
| 4f | | | 92% |
| 4g | | | 66% |

-continued

| Ex. | Reactant | Product | Yield |
|---|---|---|---|
| 4h | | | 69% |
| 4i | | | 71% |
| 4j | | | 78% |

-continued

| Ex. | Reactant | Product | Yield |
|---|---|---|---|
| 4k | | | 72% |
| 4l | | | 79% |
| 4m | | | 76% |

-continued

| Ex. | Reactant | Product | Yield |
|---|---|---|---|
| 4n | | | 72% |
| 4o | | | 80% |
| 4p | | | 76% |
| 4q | | | 75% |

-continued
| Ex. | Reactant | Product | Yield |
|---|---|---|---|
| 4r | | | 77% |
| 4s | | | 74% |
Example 5: Nucleophilic Substitution (Method 2)
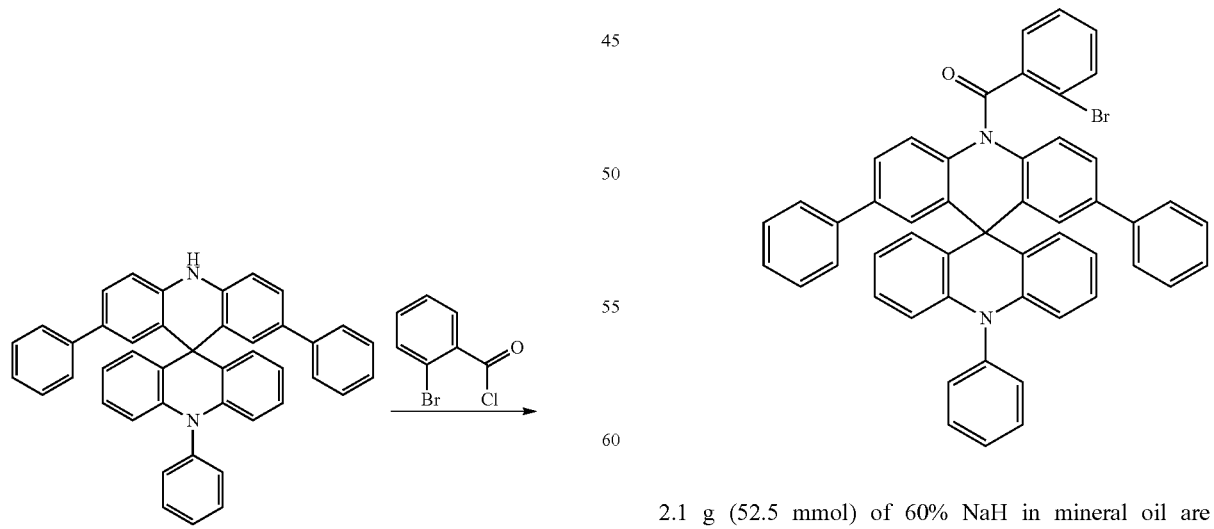
2.1 g (52.5 mmol) of 60% NaH in mineral oil are dissolved in 500 mL of THF under a protective atmosphere. 28 g (50 mmol) of the compound from example 1 and 11.5 g (52.5 mmol) of 15-crown-5 dissolved in 200 mL of THF are added. After 1 h at room temperature, a solution of 12 g (55 mmol) of 2-bromobenzoyl chloride in 250 mL of THF is added dropwise. The reaction mixture is then stirred at room temperature for 18 h.

After this time, the reaction mixture is poured onto ice and extracted three times with dichloromethane. The combined organic phases are dried over Na$_2$SO$_4$ and concentrated. The residue is subjected to hot extraction with toluene and recrystallized from toluene/n-heptane. Yield: 22 g (29 mmol), 60%; purity about 98% by $^1$H NMR.

In an analogous manner, it is possible to obtain the following compounds:

| Ex. | Reactant 1 | Reactant 2 | Product | Yield |
|---|---|---|---|---|
| 5a | | 7154-66-7 | | 68% |
| 5b | [92638-90-90] | 7154-66-7 | | 64% |
| 5c | | 72899-51-5 | | 63% |

-continued

| Ex. | Reactant 1 | Reactant 2 | Product | Yield |
|---|---|---|---|---|
| 5d | [92638-90-90] | 197370-13-1 | | 61% |
| 5e | | 25796-68-3 | | 57% |
| 5f | | 915707-69-6 | | 63% |

| Ex. | Reactant 1 | Reactant 2 | Product | Yield |
|---|---|---|---|---|
| 5g | | 58777-57-4 | | 61% |
| 5h | | 7154-66-7 | | 59% |

Example 6: Cyclization

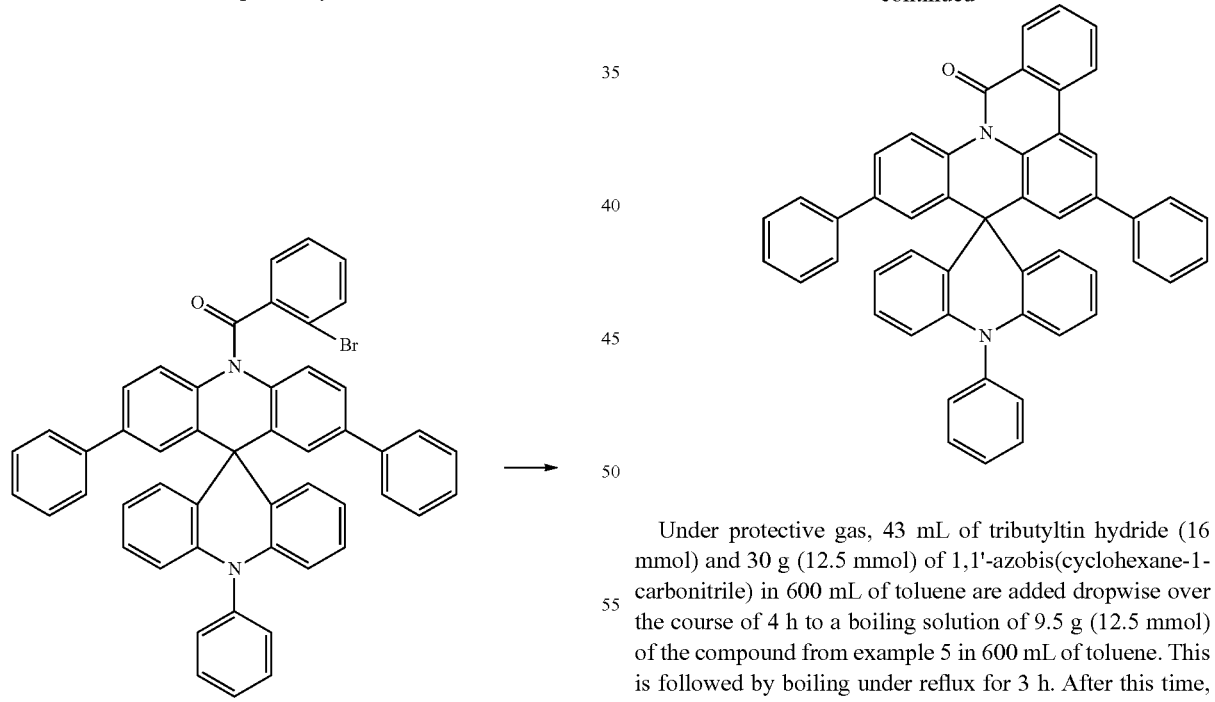

Under protective gas, 43 mL of tributyltin hydride (16 mmol) and 30 g (12.5 mmol) of 1,1'-azobis(cyclohexane-1-carbonitrile) in 600 mL of toluene are added dropwise over the course of 4 h to a boiling solution of 9.5 g (12.5 mmol) of the compound from example 5 in 600 mL of toluene. This is followed by boiling under reflux for 3 h. After this time, the reaction mixture is poured onto ice and extracted three times with dichloromethane. The combined organic phases are dried over $Na_2SO_4$ and concentrated. The residue is recrystallized from toluene and from dichloromethane/isopropanol and finally sublimed under high vacuum. Yield: 5.9 g (8.7 mmol), 70%. Purity 99.9%.

In an analogous manner, it is possible to obtain the following compounds:

| Ex. | Reactant | Product | Yield |
|---|---|---|---|
| 6a | 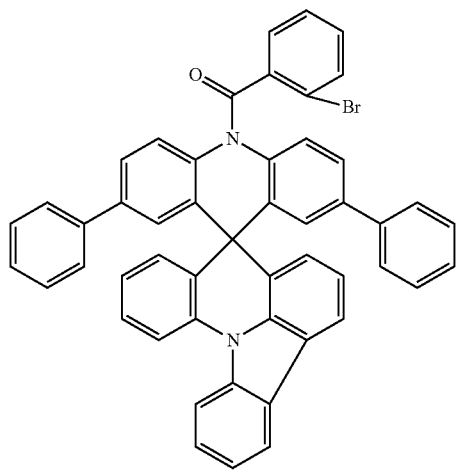 [SMILES: O=C(c1ccccc1Br)N1c2ccc(-c3ccccc3)cc2C2(c3cc(-c4ccccc4)ccc31)c1ccccc1-n1c3ccccc3c3cccc2c31] | 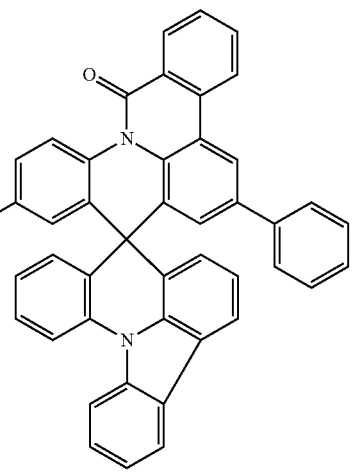 | 68% |
| 6b | 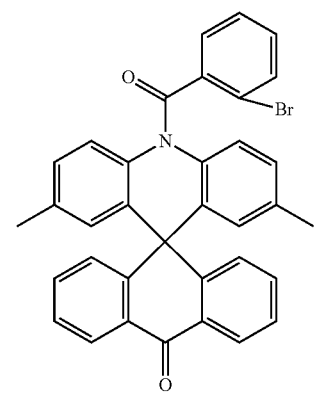 | 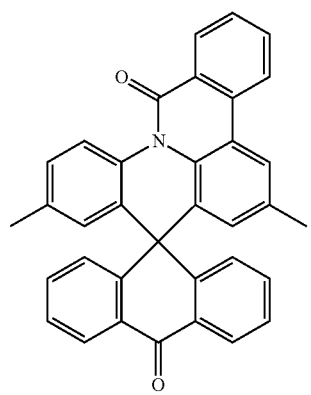 | 64% |
| 6c | 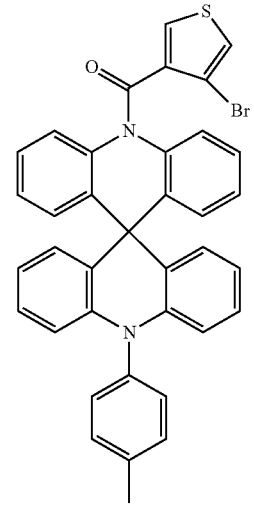 [SMILES: Cc1ccc(N2c3ccccc3C3(c4ccccc4N(C(=O)c4cscc4Br)c4ccccc43)c3ccccc32)cc1] | 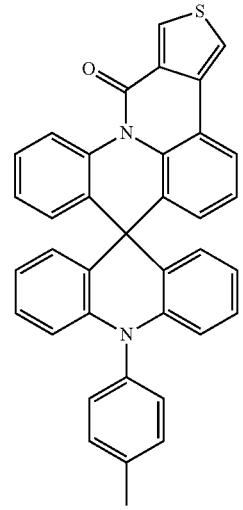 [SMILES: Cc1ccc(N2c3ccccc3C3(c4ccccc42)c2ccccc2-n2c(=O)c4cscc4c4cccc3c42)cc1] | 63% |

| Ex. | Reactant | Product | Yield |
|---|---|---|---|
| 6d | 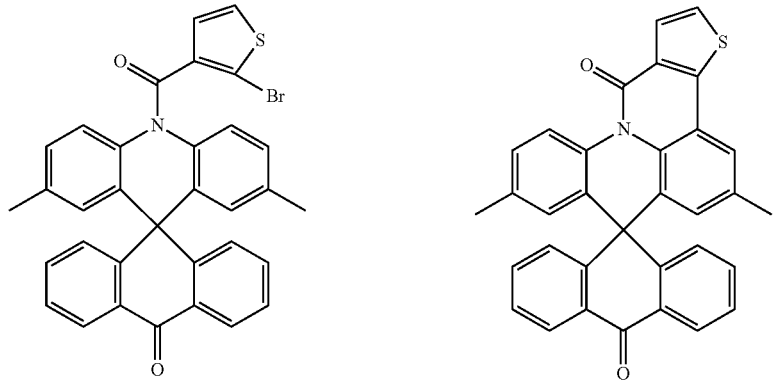 | 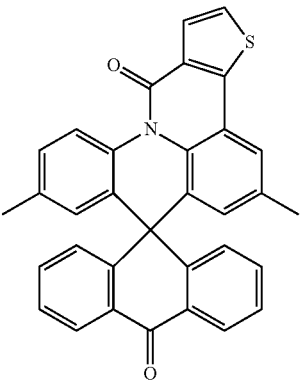 | 59% |
| 6e | 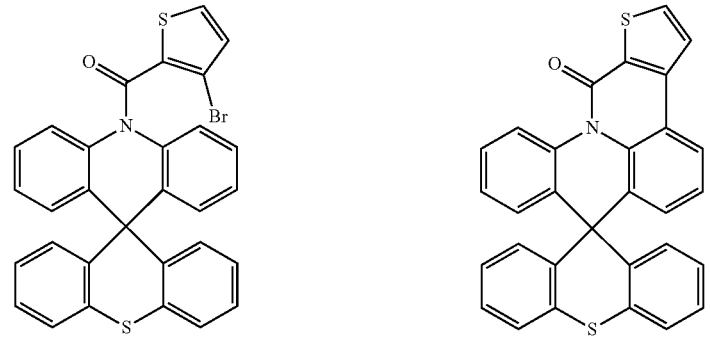 | 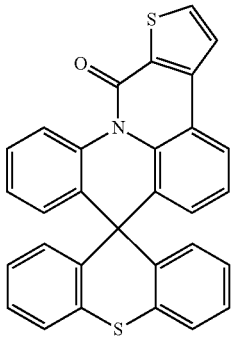 [SMILES: O=c1c2sccc2c2cccc3c2n1-c1ccccc1C31c2ccccc2Sc2ccccc21] | 64% |
| 6f | 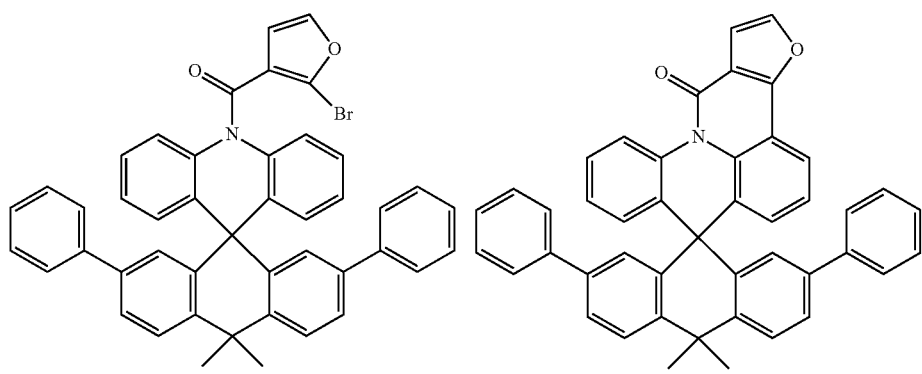 | 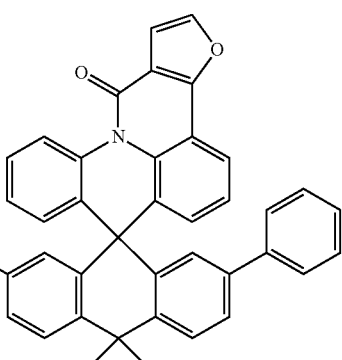 | 68% |

-continued

| Ex. | Reactant | Product | Yield |
|---|---|---|---|
| 6g | | | 62% |
| 6h | | | 63% |

Example 7: Production of the OLEDs

In examples C1 to I14 which follow (see tables 1 and 2), the data of various OLEDs are presented. Cleaned glass plaques (cleaning in laboratory glass washer, Merck Extran detergent) coated with structured ITO (indium tin oxide) of thickness 50 nm, for improved processing, are coated with 20 nm of PEDOT:PSS (poly(3,4-ethylenedioxythiophene) poly(styrenesulfonate), purchased as CLEVIOS™ P VP AI 4083 from Heraeus Precious Metals GmbH Deutschland, spun on from aqueous solution). These coated glass plaques form the substrates to which the OLEDs are applied. The OLEDs basically have the following layer structure: substrate/hole transport layer (HTL)/interlayer (IL)/electron blocker layer (EBL)/emission layer (EML)/optional hole blocker layer (HBL)/electron transport layer (ETL)/optional electron injection layer (EIL) and finally a cathode. The cathode is formed by an aluminum layer of thickness 100 nm. The exact structure of the OLEDs can be found in table 1. The materials required for production of the OLEDs are shown in table 3. A label such as "4a" relates here to the material synthesized in example 4a. The same applies to the other inventive materials.

All materials are applied by thermal vapor deposition in a vacuum chamber. In this case, the emission layer always consists of at least one matrix material (host material) and an emitting dopant (emitter) which is added to the matrix material(s) in a particular proportion by volume by co-evaporation. Details given in such a form as 6b:IC3:TEG1 (50%:40%:10%) mean here that the material 6b is present in the layer in a proportion by volume of 50%, IC3 in a proportion of 40% and TEG1 in a proportion of 10%. Analogously, the electron transport layer may also consist of a mixture of two materials.

The OLEDs are characterized in a standard manner. For this purpose, the electroluminescence spectra, the current efficiency (measured in cd/A), the power efficiency (measured in lm/W) and the external quantum efficiency (EQE, measured in percent) are determined as a function of luminance, calculated from current-voltage-luminance characteristics (IUL characteristics) assuming Lambertian radiation characteristics. The electroluminescence spectra are determined at a luminance of 1000 cd/m$^2$, and the CIE 1931 x and y color coordinates are calculated therefrom. The parameter U1000 in table 2 refers to the voltage which is required for a luminance of 1000 cd/m$^2$. CE1000 and PE1000 respectively refer to the current and power efficiencies which are achieved at 1000 cd/m$^2$. Finally, EQE1000 refers to the external quantum efficiency at an operating luminance of 1000 cd/m$^2$.

The data for the various OLEDs are collated in table 2. Examples C1-C2 are comparative examples according to the prior art; examples I1-I14 show data of OLEDs comprising inventive materials.

Some of the examples are elucidated in detail hereinafter, in order to illustrate the advantages of the inventive compounds. However, it should be pointed out that this is merely a selection of the data shown in table 2.

Use of Inventive Compounds as Matrix Materials in Phosphorescent OLEDs

By exchanging the 5-membered ring (prior art) in the spiro group of the lactam for a 6-membered ring (inventive), an improvement in the power efficiency by about 40% is obtained in the case of use as matrix material (examples C1, I2). In addition, the inventive compounds give a distinct improvement in operating lifetime. While the initial luminance in the case of an OLED comprising compound PA1 as matrix material in operation at 20 mA/cm$^2$ drops to 80% after 90 h (example C1) or 115 h (example C2), this is not the case for a corresponding OLED comprising compound 4s until after 160 h (example I1); in other words, more than a 40% increase in lifetime is obtained. With compound 4i, the initial luminance drops to 80% after 120 h (example I2).

TABLE 1

Structure of the OLEDs

| Ex. | HTL thickness | IL thickness | EBL thickness | EML thickness | HBL thickness | ETL thickness | EIL thickness |
|---|---|---|---|---|---|---|---|
| C1 | SpA1 70 nm | HATCN 5 nm | SpMA1 90 nm | PA1:TEG1 (90%:10%) 30 nm | IC1 10 nm | ST2:LiQ (50%:50%) 30 nm | — |
| C2 | SpA1 70 nm | HATCN 5 nm | SpMA1 90 nm | PA1:TEG1 (90%:10%) 30 nm | — | ST2:LiQ (50%:50%) 40 nm | — |
| I1 | SpA1 70 nm | HATCN 5 nm | SpMA1 90 nm | 4s:TEG1 (90%:10%) 30 nm | — | ST2:LiQ (50%:50%) 40 nm | — |
| I2 | SpA1 70 nm | HATCN 5 nm | SpMA1 90 nm | 4i:TEG1 (90%:10%) 30 nm | IC1 10 nm | ST2:LiQ (50%:50%) 30 nm | — |
| I3 | SpA1 70 nm | HATCN 5 nm | SpMA1 90 nm | 4j:TEG1 (90%:10%) 30 nm | IC1 10 nm | ST2:LiQ (50%:50%) 30 nm | — |
| I4 | SpA1 70 nm | HATCN 5 nm | SpMA1 90 nm | 4k:TEG1 (90%:10%) 30 nm | IC1 10 nm | ST2:LiQ (50%:50%) 30 nm | — |
| I5 | SpA1 70 nm | HATCN 5 nm | SpMA1 90 nm | 4r:IC2:TEG1 (45%:45%:10%) 30 nm | IC1 10 nm | ST2:LiQ (50%50%) 30 nm | — |
| I6 | SpA1 70 nm | HATCN 5 nm | SpMA1 90 nm | 4q:IC2:TEG1 (45%:45%:10%) 30 nm | IC1 10 nm | ST2:LiQ (50%:50%) 30 nm | — |
| I7 | SpA1 70 nm | HATCN 5 nm | SpMA1 90 nm | 4a:IC1:TEG1 (45%:45%:10%) 30 nm | IC1 10 nm | ST2:LiQ (50%:50%) 30 nm | — |
| I8 | SpA1 70 nm | HATCN 5 nm | SpMA1 90 nm | 4b:IC1:TEG1 (45%:45%:10%) 30 nm | IC1 10 nm | ST2:LiQ (50%:50%) 30 nm | — |
| I9 | SpA1 70 nm | HATCN 5 nm | SpMA1 9 0nm | 4e:IC1:TEG1 (45%:45%:10%) 30 nm | IC1 10 nm | ST2:LiQ (50%:50%) 30 nm | — |
| I10 | SpA1 90 nm | HATCN 5 nm | SpMA1 130 nm | 4p:IC2:TER1 (30%:62%:8%) 40 nm | — | ST2:LiQ (50%:50%) 40 nm | — |
| I11 | SpA1 70 nm | HATCN 5 nm | SpMA1 90 nm | 4g:IC2:TEG1 (45%:45%:10%) 30 nm | IC1 10 nm | ST2:LiQ (50%:50%) 30 nm | — |
| I12 | SpA1 70 nm | HATCN 5 nm | SpMA1 90 nm | 6b:IC3:TEG1 (50%:40%:10%) 30 nm | ST2 10 nm | ST2:LiQ (50%:50%) 30 nm | — |
| I13 | SpA1 70 nm | HATCN 5 nm | SpMA1 90 nm | IC2:TEG1 (90%:10%) 30 nm | — | 4l 40 nm | LiQ 3 nm |
| I14 | SpA1 70 nm | HATCN 5 nm | SpMA1 90 nm | IC1:TEG1 (90%:10%) 30 nm | 4s 10 nm | ST2:LiQ (50%:50%) 30 nm | — |

TABLE 2

Data of the OLEDs

| Ex. | U1000 (V) | CE1000 (cd/A) | PE1000 (lm/W) | EQE 1000 | CIE x/y at 1000 cd/m² |
|---|---|---|---|---|---|
| C1 | 4.1 | 49 | 38 | 13.7% | 0.33/0.63 |
| C2 | 3.8 | 52 | 43 | 14.0% | 0.33/0.63 |
| I1 | 3.6 | 51 | 45 | 14.3% | 0.33/0.62 |
| I2 | 3.5 | 61 | 54 | 16.6% | 0.35/0.62 |
| I3 | 3.8 | 55 | 45 | 15.5% | 0.33/0.62 |
| I4 | 4.6 | 51 | 33 | 14.3% | 0.33/0.62 |
| I5 | 3.3 | 60 | 57 | 16.1% | 0.34/0.62 |
| I6 | 3.3 | 64 | 62 | 17.3% | 0.34/0.62 |
| I7 | 3.2 | 56 | 56 | 15.8% | 0.33/0.62 |
| I8 | 3.4 | 57 | 52 | 15.9% | 0.33/0.63 |
| I9 | 3.4 | 58 | 54 | 16.2% | 0.33/0.62 |
| I10 | 4.4 | 11.0 | 7.9 | 11.9% | 0.67/0.33 |
| I11 | 3.1 | 57 | 57 | 15.8% | 0.33/0.62 |
| I12 | 4.2 | 40 | 29 | 11.1% | 0.33/0.62 |
| I13 | 4.6 | 43 | 36 | 14.9% | 0.33/0.62 |
| I14 | 4.7 | 51 | 34 | 14.3% | 0.33/0.62 |

TABLE 3

Structural formulae of the materials for the OLEDs

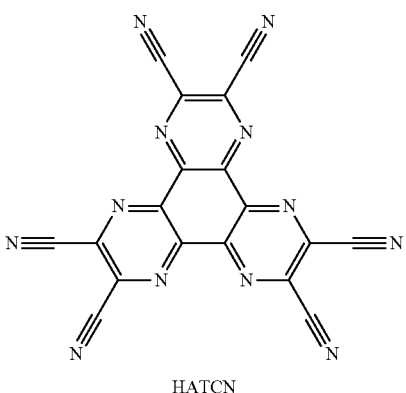 [SMILES: N#Cc1nc2c3nc(C#N)c(C#N)nc3c3nc(C#N)c(C#N)nc3c2nc1C#N]

HATCN

TABLE 3-continued
Structural formulae of the materials for the OLEDs
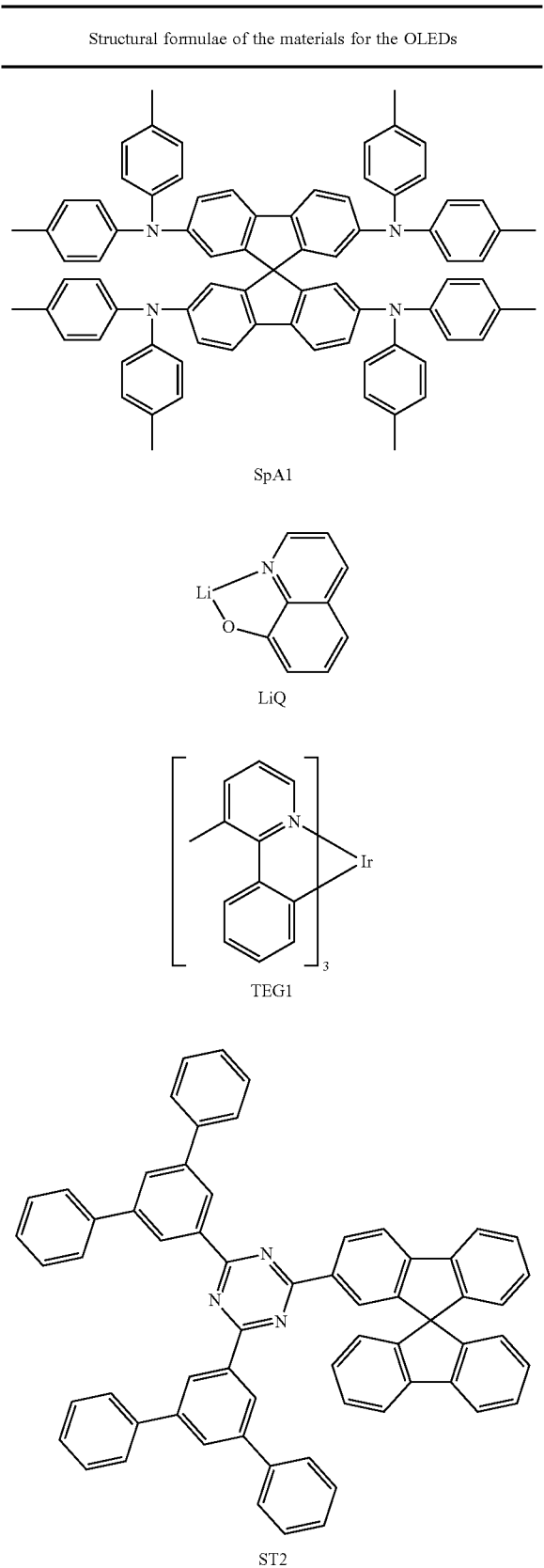
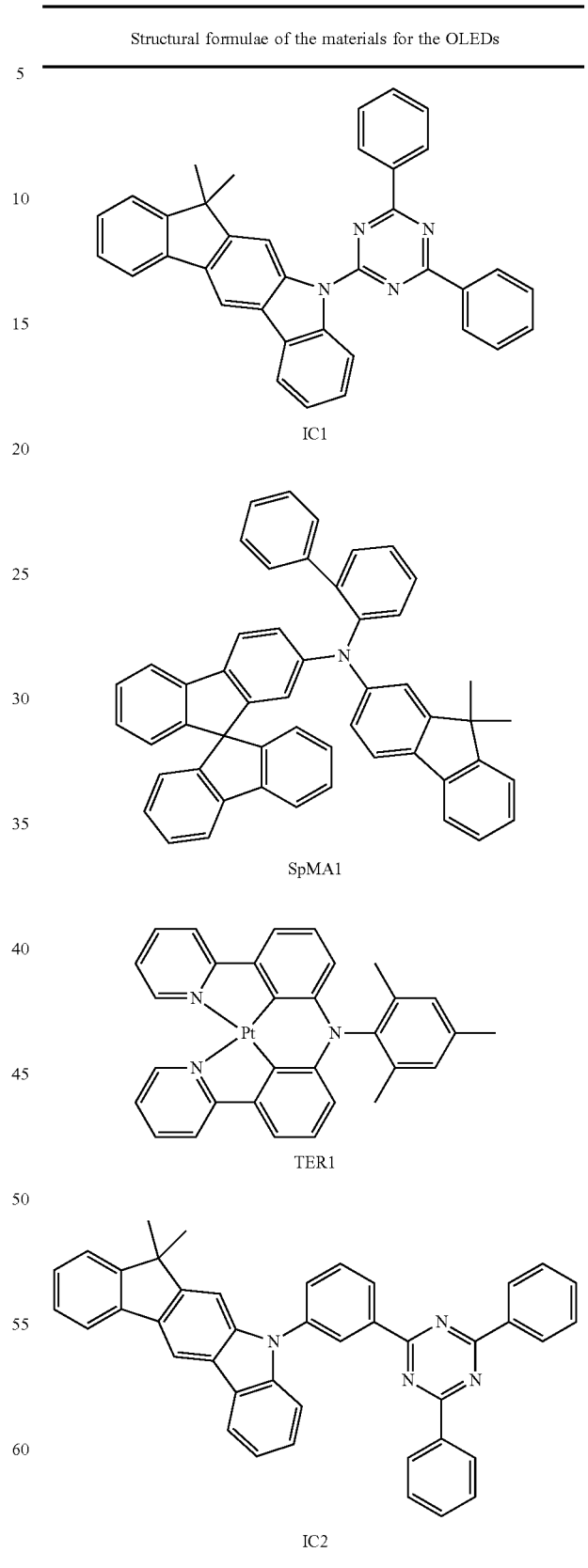

TABLE 3-continued

Structural formulae of the materials for the OLEDs

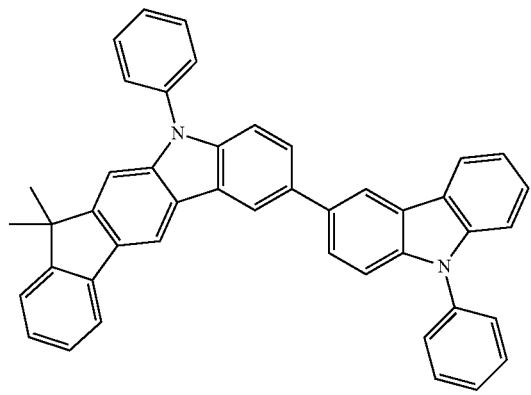

IC3

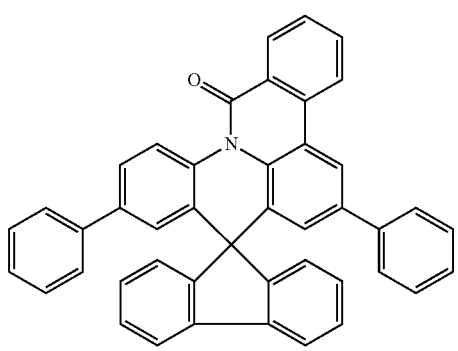

PA1

The invention claimed is:

1. An organic electroluminescent device comprising a light-emitting layer and a compound of formula (16a) as a matrix material for a phosphorescent emitter in the light-emitting layer

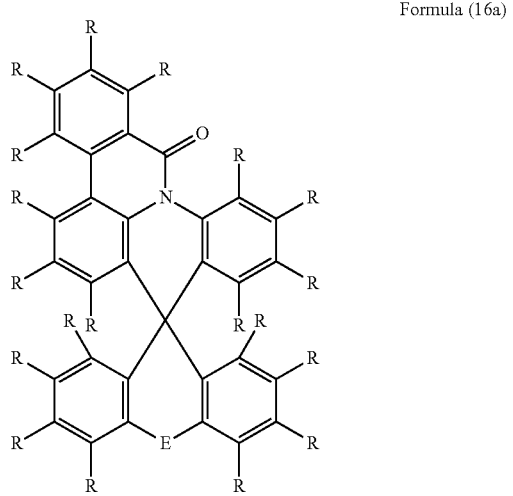

Formula (16a)

where the symbols and indices used are as follows:
E is O;
R is the same or different at each instance and is selected from the group consisting of H, D, F, Cl, Br, I, CN, $NO_2$, $N(Ar^4)_2$, $N(R^1)_2$, $C(=O)Ar^4$, $C(=O)R^1$, $P(=O)(Ar^4)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which is optionally substituted by one or more $R^1$ radicals, where one or more nonadjacent $CH_2$ groups is optionally replaced by $R^1C=CR^1$, $C\equiv C$, $Si(R^1)_2$, $Ge(R^1)_2$, $Sn(R^1)_2$, $C=O$, $C=S$, $C=Se$, $C=NR^1$, $P(=O)(R^1)$, SO, $SO_2$, $NR^1$, O, S or $CONR^1$ and where one or more hydrogen atoms is optionally replaced by D, F, Cl, Br, I, CN or $NO_2$, an aromatic or heteroaromatic ring system which has 5 to 80 aromatic ring atoms and is optionally substituted in each case by one or more $R^1$ radicals, an aryloxy or heteroaryloxy group which has 5 to 60 aromatic ring atoms and is optionally substituted by one or more $R^1$ radicals, or a combination of these systems, where it is optionally possible for two or more adjacent R substituents to form a monocyclic or polycyclic, aliphatic, aromatic or heteroaromatic ring system which is optionally substituted by one or more $R^1$ radicals;

$R^1$ is the same or different at each instance and is selected from the group consisting of H, D, F, Cl, Br, I, CN, $NO_2$, $N(Ar^4)_2$, $N(R^2)_2$, $C(=O)Ar^4$, $C(=O)R^2$, $P(=O)(Ar^4)_2$, a straight-chain alkyl, alkoxy or thioalkyl group having 1 to 40 carbon atoms or a branched or cyclic alkyl, alkoxy or thioalkyl group having 3 to 40 carbon atoms or an alkenyl or alkynyl group having 2 to 40 carbon atoms, each of which is optionally substituted by one or more $R^2$ radicals, where one or more non-adjacent $CH_2$ groups is optionally replaced by $R^2C=CR^2$, $C\equiv C$, $Si(R^2)_2$, $Ge(R^2)_2$, $Sn(R^2)_2$, $C=O$, $C=S$, $C=Se$, $C=NR^2$, $P(=O)(R^2)$, SO, $SO_2$, $NR^2$, O, S or $CONR^2$ and where one or more hydrogen atoms is optionally replaced by D, F, Cl, Br, I, CN or $NO_2$, an aromatic or heteroaromatic ring system which has 5 to 60 aromatic ring atoms and is optionally substituted in each case by one or more $R^2$ radicals, an aryloxy or heteroaryloxy group which has 5 to 60 aromatic ring atoms and is optionally substituted by one or more $R^2$ radicals, or a combination of these systems, where it is optionally possible for two or more adjacent R substituents to form a monocyclic or polycyclic, aliphatic, aromatic or heteroaromatic ring system which is optionally substituted by one or more $R^2$ radicals;

$Ar^4$ is the same or different at each instance and is an aromatic or heteroaromatic ring system which has 5-30 aromatic ring atoms and is optionally substituted by one or more nonaromatic $R^2$ radicals; at the same time, two $Ar^4$ radicals bonded to the same nitrogen atom or phosphorus atom may also be bridged to one another by a single bond or a bridge selected from $N(R^2)$, $C(R^2)_2$ and O;

$R^2$ is selected from the group consisting of H, D, F, CN, an aliphatic hydrocarbyl radical having 1 to 20 carbon atoms, an aromatic or heteroaromatic ring system having 5 to 30 aromatic ring atoms in which one or more hydrogen atoms is optionally replaced by D, F, Cl, Br, I or CN, where two or more adjacent $R^2$ substituents together may form a mono- or polycyclic, aliphatic, aromatic or heteroaromatic ring system.

2. The device as claimed in claim 1, wherein the compound of formula (16a) may be represented by a compound of the formulae (16b)

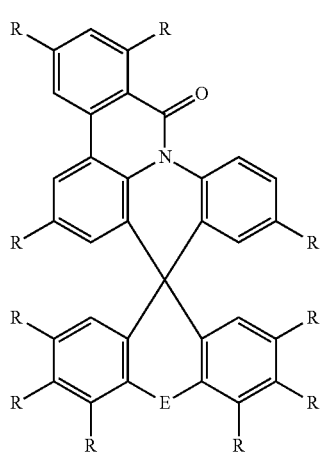

Formula (16b)

3. A process for preparing the compound as claimed in claim 1, comprising the reaction steps of:
   a) preparing a spiro compound proceeding from a xathone derivative; and
   b) substituting the nitrogen, followed by cyclizing to give the lactam.

4. The device of claim 1 comprising an oligomer, polymer or dendrimer containing one or more of the compound of (16a), wherein one or more bonds of the compound to the polymer, oligomer or dendrimer are present.

\* \* \* \* \*